US008999334B2

(12) United States Patent
Chahal et al.

(10) Patent No.: US 8,999,334 B2
(45) Date of Patent: Apr. 7, 2015

(54) ANTIBODY CONJUGATES AGAINST VARIANT NFKBIB AND USES THEREOF

(71) Applicant: Viventia Bio Inc., Winnipeg (CA)

(72) Inventors: Francina C. Chahal, Winnipeg (CA); Jeannick Cizeau, Winnipeg (CA)

(73) Assignee: Viventia Bio Inc. (CA)

( * ) Notice: Subject to any disclaimer, the term of this patent is extended or adjusted under 35 U.S.C. 154(b) by 0 days.

(21) Appl. No.: 13/850,899

(22) Filed: Mar. 26, 2013

(65) Prior Publication Data

US 2013/0344076 A1     Dec. 26, 2013

Related U.S. Application Data

(62) Division of application No. 12/744,523, filed as application No. PCT/CA2008/002076 on Nov. 27, 2008, now Pat. No. 8,426,561.

(60) Provisional application No. 60/990,494, filed on Nov. 27, 2007.

(51) Int. Cl.
| A61K 39/395 | (2006.01) |
| A61K 39/00 | (2006.01) |
| G01N 33/574 | (2006.01) |
| A61K 47/48 | (2006.01) |
| C07K 14/21 | (2006.01) |
| C07K 16/18 | (2006.01) |
| C07K 16/30 | (2006.01) |
| G01N 33/50 | (2006.01) |

(52) U.S. Cl.
CPC .......... *C07K 16/30* (2013.01); *A61K 47/48469* (2013.01); *A61K 47/48538* (2013.01); *A61K 47/48569* (2013.01); *A61K 2039/505* (2013.01); *C07K 14/21* (2013.01); *C07K 16/18* (2013.01); *C07K 2317/21* (2013.01); *C07K 2317/56* (2013.01); *C07K 2317/77* (2013.01); *G01N 33/5023* (2013.01); *G01N 33/57496* (2013.01)

(58) Field of Classification Search
None
See application file for complete search history.

(56) References Cited

U.S. PATENT DOCUMENTS

| 7,396,915 B2 * | 7/2008 | Hosokawa et al. ........ 530/387.7 |
| 7,566,772 B2 * | 7/2009 | Green et al. ............ 530/388.15 |
| 2007/0202593 A1 | 8/2007 | Liu et al. |

FOREIGN PATENT DOCUMENTS

| WO | WO 02/12497 | * | 2/2002 |
| WO | WO 02/12497 A2 | | 2/2002 |
| WO | WO2004/035783 A2 | | 4/2004 |
| WO | WO 2006/081139 A1 | | 8/2006 |

OTHER PUBLICATIONS

Rudikoff et al. (Proc Natl Acad Sci USA 1982 vol. 79 p. 1979).*
MacCallum et al. J. Mol. Biol. (1996) 262, 732-745.*
Wu et al (J Leukocyte Biology, 1999, 66:1049-1056).*
Database UniPot Accession No. Q15653, retrieved from internet Sep. 4, 2013.
Office Action issued Mar. 18, 2013 for corresponding Australian Application No. 2008329518.
Brauninger, et al., "*Homo sapiens* partial IGVL3r gene for immunoglobulin lambda chain variable region donor BJ, cell 103", Oct. 10, 2001 Genbank Accession No. AJ414907.
Brauninger et al., "Regulation of immunoglobulin light chain gene rearrangements during early B cell development in the human", *Eur J Immunol.* (Dec. 2001), 31(12):3631-3637.
Chen et al., "Amplification of immunoglobulin transcripts by the non-palindromic adaptor polymerase chain reaction (NPA-PCR). Nucleotide sequence analysis of two human monoclonal antibodies recognizing two cell surface antigens expressed in ovarian, cervix, breast, colon and other carcinomas", *Hum. Antibodies Hybridomas* (1994), 5(3-4):131-142 (Abstract only).
EBI Accession No. GSP:AJF57817, Database accession No. AJF57817, "Human inhibitor of NF-κB, IκB β isoform a protein", Abstract; sequence, 2007.
GenBank Accession No. AAB34387, Anti-carcinoma surface antigen monoclonal antibody CR4E8, partial (Sep. 26, 1995).
Hayden, et al., "Signaling to NF-κB", *Genes & Development* (Sep. 15, 2004), 18(18):2195-2224.
Kanzler, et al., "*Homo sapiens* hv3005 gene for immunoglobulin heavy chain variable region case 2", Sep. 2, 1999. Genbank Accession No. AJ242564.

* cited by examiner

*Primary Examiner* — Laura B Goddard
(74) *Attorney, Agent, or Firm* — Cooley LLP

(57) ABSTRACT

The present application provides the amino acid and nucleic acid sequences of heavy and light chain complementarity determining regions of a cancer specific antibody directed to an epitope of variant Nuclear Factor Kappa-B inhibitor beta (NFKBIB). In addition, the application provides cancer specific antibodies and immunoconjugates comprising the cancer specific antibody attached to a toxin or a label, and methods of uses thereof. The application also relates to diagnostic methods and kits using the cancer specific antibodies herein. Further, the application provides novel cancer-associated epitopes and antigens of variant NFKBIB, and uses thereof.

29 Claims, 17 Drawing Sheets

Figure 1A

A: VB1-204 Heavy Chain Nucleotide and Amino Acid Sequences (SEQ ID NO 1 and 2)

```
GAG GTG CAG CTG GTG GAG TCT GGG GGA GGC GTG GTC CAG CCT GGG AGG TCC CTG AGA
 E   V   Q   L   V   E   S   G   G   G   V   V   Q   P   G   R   S   L   R
|----------- V_H Start -----
CTC TCC TGT GCA GCC TCT GGA TTC ACC TTC AGT AGC TAT GCT ATG CAC TGG GTC CGC
 L   S   C   A   A   S   G   F   T   F   S   S   Y   A   M   H   W   V   R
                                             |—————— CDR 1 ——————|
CAG GCT CCA GGC AAG GGG CTG GAG TGG GTG GCA GTT ATA TCA TAT GAT GGA AGT AAT
 Q   A   P   G   K   G   L   E   W   V   A   V   I   S   Y   D   G   S   N
                                             |—————————————— CDR 2 ——
AAA TAC TAC GCA GAC TCC CTG AAG GGC CGA TTC ACC ATC TCC AGA GAC AAT TCC AAG
 K   Y   Y   A   D   S   V   K   G   R   F   T   I   S   R   D   N   S   K
————————————————————————————|
AAC ACG CTG TAT CTG CAA ATG AAC AGC CTG AGA GCT GAG GAC ACG GCT GTG TAT TAC
 N   T   L   Y   L   Q   M   N   S   L   R   A   E   D   T   A   V   Y   Y TGT GCG AGA GCA CAT TCC CGC TTA CTA TGG TTC GGG GAG TTA TTA CCC AGC GCT TTT
 C   A   R   A   H   S   R   L   L   W   F   G   E   L   L   P   S   A   F
            |————————————————— CDR 3 ————————————————————————————————

GAC TAC TGG GGC CAG GGA ACC CTG GTC ACC GTC TCC TCA    (SEQ ID NO:1)
 D   Y   W   G   Q   G   T   L   V   T   V   S   S    (SEQ ID NO:2)
————————|                V_H End ------------------|
```

Figure 1B

B: VB1-204 Light Chain Nucleotide and Amino Acid Sequences (SEQ ID NO: 3 and 4)

```
TCC TAT GAG CTG ACT CAG CCA CCC TCA GTG TCC GTG TCC CCA GGA CAG ACA GCC AGC
 S   Y   E   L   T   Q   P   P   S   V   S   V   S   P   G   Q   T   A   S
|---------- V_L Start -----
ATC ACC TGC TCT GGA GAT AAA TTG GGG GAT AAA TAT GCT TGC TGG TAT CAG CAG AAG
 I   T   C   S   G   D   K   L   G   D   K   Y   A   C   W   Y   Q   Q   K
             |————————————— CDR 1 ——————————————|
CCA GGC CAG TCC CCT GTG CTG GTC ATC TAT CAA GAT AGC AAG CGG CCC TCA GGG ATC
 P   G   Q   S   P   V   L   V   I   Y   Q   D   S   K   R   P   S   G   I
                                     |—————————— CDR 2 ——————————|
CCT GAG CGA TTC TCT GGC TCC AAC TCT GGG AAC ACA GCC ACT CTG ACC ATC AGC GGG
 P   E   R   F   S   G   S   N   S   G   N   T   A   T   L   T   I   S   G ACC CAG GCT ATG GAT GAG GCT GAC TAT TAC TGT CAG GCG TGG GAC AGC AGC ACT GTG
 T   Q   A   M   D   E   A   D   Y   Y   C   Q   A   W   D   S   S   T   V
                                             |———————— CDR 3 ———————————
GTA TTC GGC GGA GGG ACC AAG CTG ACC GTC CTA GGT (SEQ ID NO:3)
 V   F   G   G   G   T   K   L   T   V   L   G   (SEQ ID NO:4)
——|           V_L End ------------------|
```

Figure 4
A)
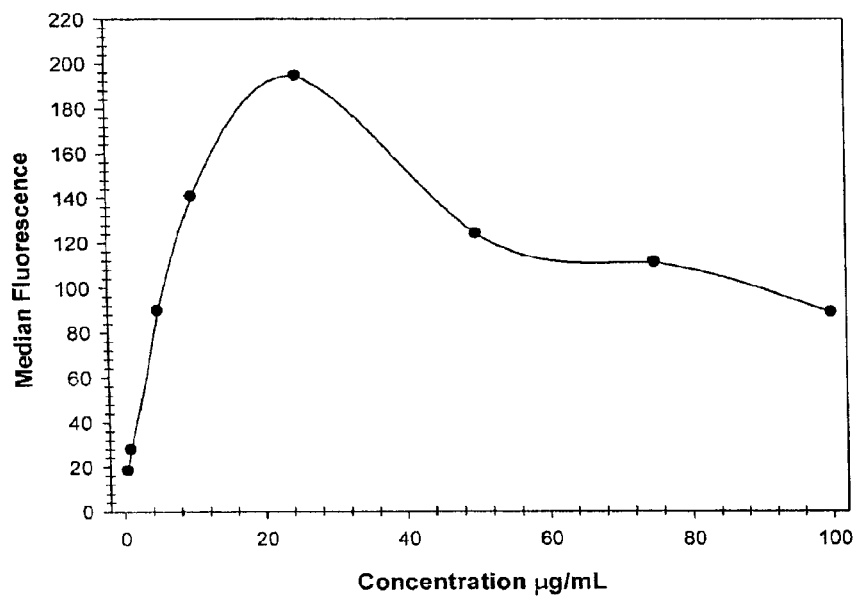
B)
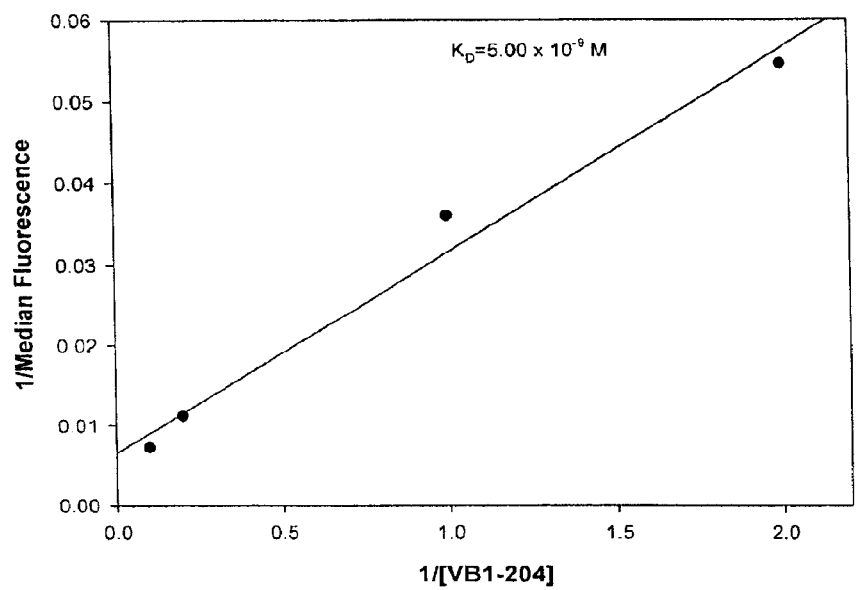

Figure 5
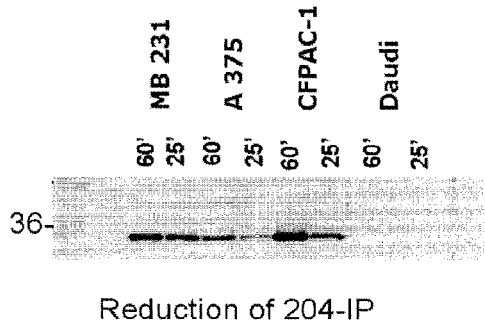
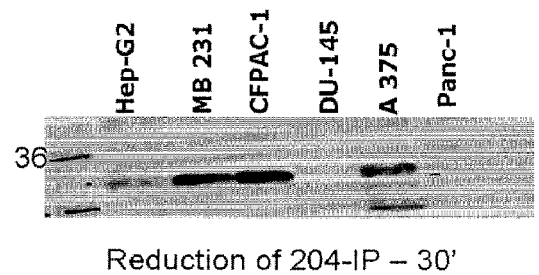
Reduction of 204-IP　　　　　　　Reduction of 204-IP – 30'

Figure 7A

Figure 7A: CFPAC-1

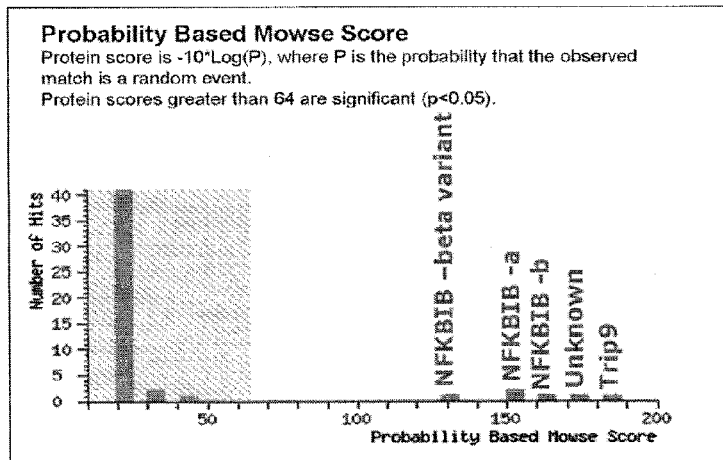

ACC 41742 Hum TRIP9 62% Coverage (SEQ ID NO.27) (Human IkBβ isoform 2)

```
1   MAGVACLGKA ADADEWCDTG LGSLGPDAAA PGGPGLGAEL GPGLSWAPLV
51  FGYVTEDGDT ALHLAVIHQH EPFLDFLLGF SAGTEYMDLQ NDLGQTALHL
101 AAILGETSTV EKLYAAGAGL CVAERRGHTA LHLACRVGAH ACARALLQPR
151 PRRPREAPDT YLAQGPDRTP DTNHTPVALY PDSDLEKEEE ESEEDWKLQL
201 EAENYEGHTP LHVAVIHKDV EMVRLLRDAG ADLDKPEPTC GRSPLHLAVE
251 AQAADVLELL LRAGANPAAR MYGGRTPLGS AMLRPNPILA RLLRAHGAPE
301 PEGEDEKSGP CSSSSDSDGG DEGVSQEERQ GSPAGGSG
```

Q15653 Hum IkBβ Isoform1 (NFkBIB-a) (SEQ ID NO. 28)

```
1   MAGVACLGKA ADADEWCDSG LGSLGPDAAA PGGPGLGAEL GPGLSWAPLV
51  FGYVTEDGDT ALHLAVIHQH EPFLDFLLGF SAGTEYMDLQ NDLGQTALHL
101 AAILGETSTV EKLYAAGAGL CVAERRGHTA LHLACRVGAH ACARALLQPR
151 PRRPREAPDT YLAQGPDRTP DTNHTPVALY PDSDLEKEEE ESEEDWKLQL
201 EAENYEGHTP LHVAVIHKDV EMVRLLRDAG ADLDKPEPTC GRSPLHLAVE
251 AQAADVLELL LRAGANPAAR MYGGRTPLGS AMLRPNPILA RLLRAHGAPE
301 PEGEDEKSGP CSSSSDSDSG DEGDEYDDIV VHSSRSQTRL PPTPASKPLP
351 DDPRP
```

BAD93021 NF-kappaB inhibitor (NFkBIB) beta variant (SEQ ID NO:29) (Human IkBβ2 beta variant)

```
1   LQNSRQSPAT GGRLRGAPEA AGAMAGVACL GKAADADEWC DSGLGSLGPD
51  AAAPGGPGLG AELGPGLSWA PLVFGYVTED GDTALHLAVI HQHEPFLDFL
101 LGFSAGTEYM DLQNDLGQTA LHLAAILGET STVEKLYAAG AGLCVAERRG
151 HTALHLACRV GAHACARALL QPRPRRPREA PDTYLAQGPD RTPDTNHTPV
201 ALYPDSDLEK EEEESEEDWK LQLEAENYEG HTPLHVAVIH KDVEMVRLLR
251 DAGADLDKPE PTCGRSPLHL AVEAQAADVL ELLLRAGANP AARMYGGRTP
301 LGSAMLRPNP ILARLLRAHG APEPEGEDEK SGPCSSSSDS DSGDEGVSQE
351 ERQGSPAGGSG
```

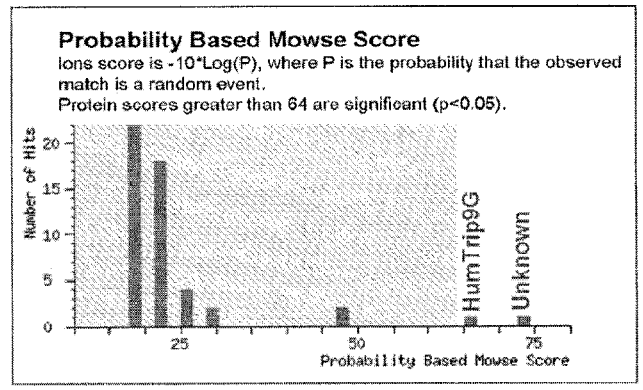

ACC 41742 Hum TRIP9 55% Coverage (SEQ ID NO. 27) (Human IkBβ isoform 2)

```
1   MAGVACLGKA ADADEWCDTG LGSLGPDAAA PGGPGLGAEL GPGLSWAPLV
51  FGYVTEDGDT ALHLAVIHQH EPFLDFLLGF SAGTEYMDLQ NDLGQTALHL
101 AAILGETSTV EKLYAAGAGL CVAERRGHTA LHLACRVGAH ACARALLQPR
151 PRRPREAPDT YLAQGPDRTP DTNHTPVALY PDSDLEKEEE ESEEDWKLQL
201 EAENYEGHTP LHVAVIHKDV EMVRLLRDAG ADLDKPEPTC GRSPLHLAVE
251 AQAADVLELL LRAGANPAAR MYGGRTPLGS AMLRPNPILA RLLRAHGAPE
301 PEGEDEKSGP CSSSSDSDGG DEGVSQEERQ GSPAGGSG
```

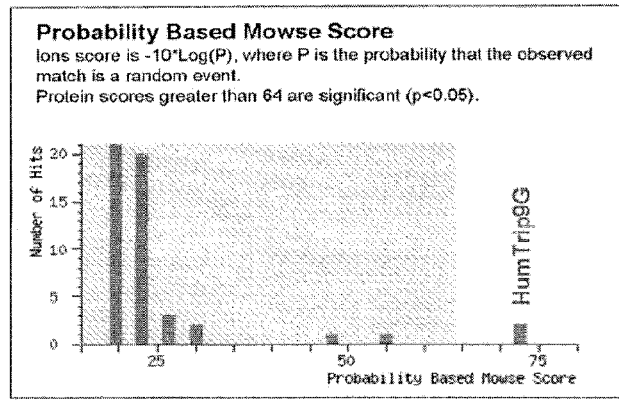

ACC 41742 Hum TRIP9 56% Coverage (SEQ ID NO. 55) (Human IkBβ isoform 2)

```
1   MAGVACLGKA ADADEWCDTG LGSLGPDAAA PGGPGLGAEL GPGLSWAPLV
51  FGYVTEDGDT ALHLAVIHQH EPFLDFLLGF SAGTEYMDLQ NDLGQTALHL
101 AAILGETSTV EKLYAAGAGL CVAERRGHTA LHLACRVGAH ACARALLQPR
151 PRRPREAPDT YLAQGPDRTP DTNHTPVALY PDSDLEKEEE ESEEDWKLQL
201 EAENYEGHTP LHVAVIHKDV EMVRLLRDAG ADLDKPEPTC GRSPLHLAVE
251 AQAADVLELL LRAGANPAAR MYGGRTPLGS AMLRPNPILA RLLRAHGAPE
301 PEGEDEKSGP CSSSSDSDGG DEGVSQEERQ GSPAGGSG
```

Figure 8

Variant IkBβ Human Isoform 2 (SEQ ID NO.30)

```
1   MAGVACLGKA ADADEWCDTG LGSLGVLAAA VGGVGLGAWL GPGLSWAPLV
51  FGYVTEDGDT ALHLAVIHQH EPFLDFLLGF SAGTEYMDLQ NDLGQTALHL
101 AAILGVTSTV VALYAAGAGL CVAERRGHTA LHLACRVGAH ACARALLQPR
151 PRRPREAPDT YLAQGPDRTP DTNHTPVALY PDSDLEKEEE ESEEDWKLQL
201 EAENYEGHTP LHVAVIHKDV EMVRLLRDAG ADLDKPEPTC GRSPLHLAVE
251 AQAADVLELL LRAGANPAAR MYGGRTPLGS AMLRPNPILA RLLRAHGAPE
301 PEGEDEKSGP CSSSSDSDGG DEGVSQEERQ GSPAGGSG
```

Figure 9
Figure 9A: LGVLAAAVGGVGLGAWL (SEQ ID NO: 34)
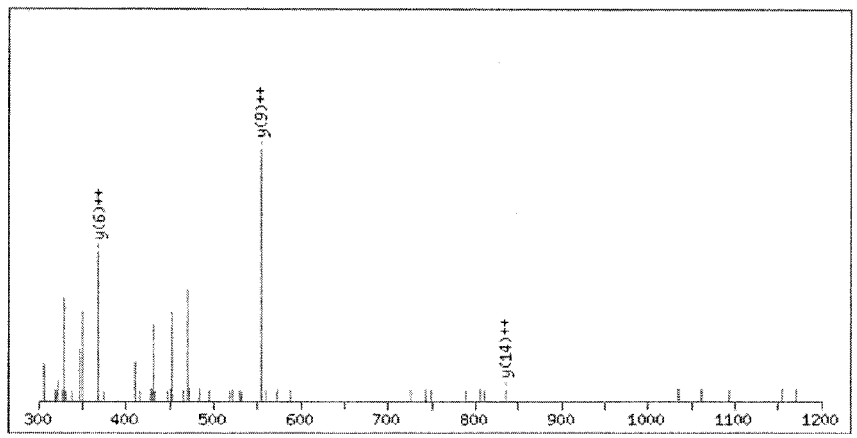
Figure 9B: ILGVTSTVVAL (SEQ ID NO: 37)
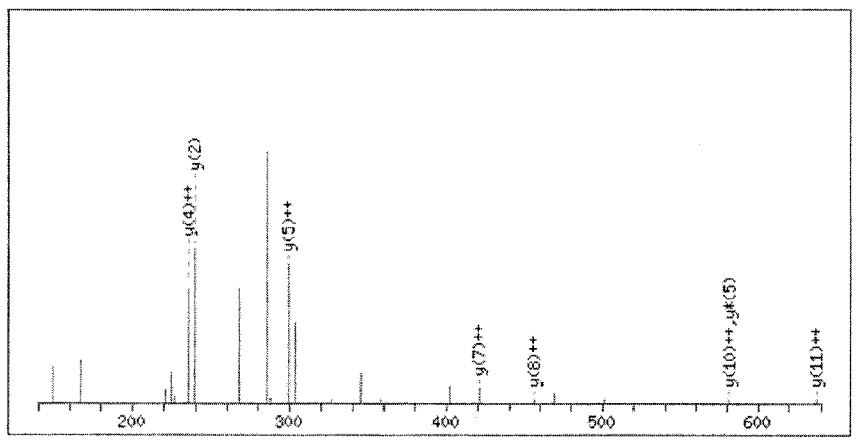
Figure 9C: FLLGFSAGTEY (SEQ ID NO: 35)
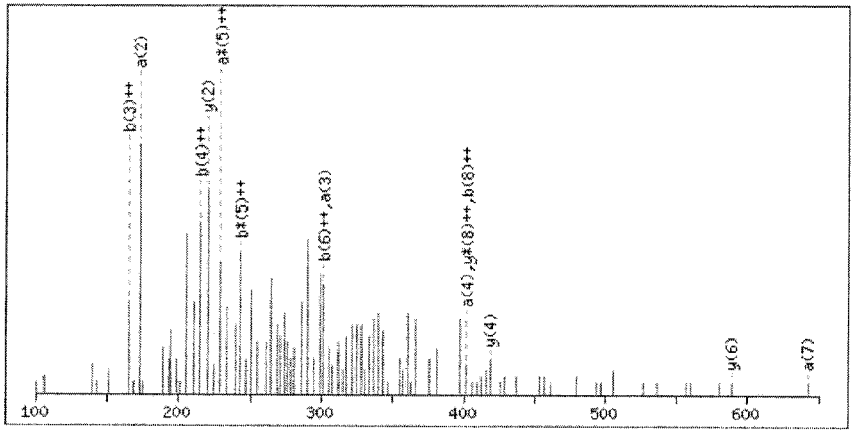

Blotted with    VB1-204    IkBβ antibody

Lane   1    2    3    4

Legend
| Lane # | Sample |
| --- | --- |
| 1 | Whole cell lysate IP with VB1-204 |
| 2 | CFPAC-1 membrane IP with VB1-204 |
| 3 | Whole cell lysate IP with VB1-204 |
| 4 | CFPAC-1 membrane IP with VB1-204 |

Figure 11

VB1-204 Nucleotide Sequences and Amino Acid (SEQ ID NO: 66 and 67)

```
GAA TTC CTG CAG GTC TAT GGA ACG ATA AAT GCC CAT GAA AAT TCT ATT TCA AGG

AGA CAG TCA TA ATG AAA TAC CTA TTG CCT ACG GCA GCC GCT GGA TTG TTA TTA
              M   K   Y   L   L   P   T   A   A   A   G   L   L   L
            |_____ PelB Leader Sequence CTC GCT GCC CAA CCA GCG ATG GCG GAG GTG CAG CTG GTG GAG TCT GGG GGA GGC
 L   A   A   Q   P   A   M   A   E   V   Q   L   V   E   S   G   G   G
                                     |  |-------- V_H Start GTG GTC CAG CCT GGG AGG TCC CTG AGA CTC TCC TGT GCA GCC TCT GGA TTC ACC
 V   V   Q   P   G   R   S   L   R   L   S   C   A   A   S   G   F   T TTC AGT AGC TAT GCT ATG CAC TGG GTC CGC CAG GCT CCA GGC AAG GGG CTG GAG
 F   S   S   Y   A   M   H   W   V   R   Q   A   P   G   K   G   L   E
         |—— CDR1 ——|

TGG GTG GCA GTT ATA TCA TAT GAT GGA AGT AAT AAA TAC TAC GCA GAC TCC GTG
 W   V   A   V   I   S   Y   D   G   S   N   K   Y   Y   A   D   S   V
             |————————————————— CDR2 —————————————————

AAG GGC CGA TTC ACC ATC TCC AGA GAC AAT TCC AAG AAC ACG CTG TAT CTG CAA
 K   G   R   F   T   I   S   R   D   N   S   K   N   T   L   Y   L   Q
—————|

ATG AAC AGC CTG AGA GCT GAG GAC ACG GCT GTG TAT TAC TGT GCG AGA GCA CAT
 M   N   S   L   R   A   E   D   T   A   V   Y   Y   C   A   R   A   H
                                                             |—

TCC CGC TTA CTA TGG TTC GGG GAG TTA TTA CCC AGC GCT TTT GAC TAC TGG GGC
 S   R   L   L   W   F   G   E   L   L   P   S   A   F   D   Y   W   G
—————————————————— CDR3 ——————————————————|

CAG GGA ACC CTG GTC ACC GTC TCC TCA GCT TCC ACC AAG GGC CCA TCG GTC TTC
 Q   G   T   L   V   T   V   S   S   A   S   T   K   G   P   S   V   F
                    V_H End --||----------- C_H Start CCC CTG GCA CCC TCC TCC AAG AGC ACC TCT GGG GGC ACA GCG GCC CTG GGC TGC
 P   L   A   P   S   S   K   S   T   S   G   G   T   A   A   L   G   C CTG GTC AAG GAC TAC TTC CCC GAA CCG GTG ACG GTG TCG TGG AAC TCA GGC GCC
 L   V   K   D   Y   F   P   E   P   V   T   V   S   W   N   S   G   A CTG ACC AGC GGC GTG CAC ACC TTC CCG GCT GTC CTA CAG TCC TCA GGA CTC TAC
 L   T   S   G   V   H   T   F   P   A   V   L   Q   S   S   G   L   Y TCC CTC AGC AGC GTG GTG ACC GTG CCC TCC AGC AGC TTG GGC ACC CAG ACC TAC
 S   L   S   S   V   V   T   V   P   S   S   S   L   G   T   Q   T   Y ATC TGC AAC GTG AAT CAC AAG CCC AGC AAC ACC AAG GTG GAC AAG AAA GTT GAG
 I   C   N   V   N   H   K   P   S   N   T   K   V   D   K   K   V   E CCC AAA TCT TGT ACC AGG CAC AGG CAG CCC ACA CCC TGG GAG CAG CTC TAC AAC
 P   K   S   C   T   R   H   R   Q   P   R   G   W   E   Q   L   Y   N
 C_H end --------||------------------ Furin linker --------------||-----
```

Continued Figure 11

```
ACC GTG TCA TTT AAC CTT GGA GAA GCT TAT GAG TAC CCC ACT TTT ATA CAA GAT
 T   V   S   F   N   L   G   E   A   Y   E   Y   P   T   F   I   Q   D
--de-bouganin Start TTG CGC AAT GAA TTG GCT AAG GGC ACA CCA GTA TGT CAA CTT CCA GTG ACA CTA
 L   R   N   E   L   A   K   G   T   P   V   C   Q   L   P   V   T   L CAA ACC ATA GCC GAT GAC AAG CGA TTT GTT CTA GTT GAT ATC ACT ACG ACC TCG
 Q   T   I   A   D   D   K   R   F   V   L   V   D   I   T   T   T   S AAG AAA ACA GTT AAG GTT GCT ATA GAT GTC ACA GAT GTC TAT GTT GTG GGT TAT
 K   K   T   V   K   V   A   I   D   V   T   D   V   Y   V   V   G   Y CAA GAC AAA TGG GAT GGC AAA GAT CGA GCT GTT TTC CTT GAC AAG GTT CCT ACT
 Q   D   K   W   D   G   K   D   R   A   V   F   L   D   K   V   P   T GTT GCA ACT AGT AAA CTT TTC CCA GGG GTG ACT AAT CGT GTA ACG TTA ACA TTT
 V   A   T   S   K   L   F   P   G   V   T   N   R   V   T   L   T   F GAT GGC AGC TAT CAG AAA CTT GTG AAT GCT GCC AAA GCT GAT AGA AAG GCT CTC
 D   G   S   Y   Q   K   L   V   N   A   A   K   A   D   R   K   A   L GAA CTG GGG GTT AAC AAA TTG GAA TTT TCC ATT GAA GCA ATC CAT GGT AAA ACG
 E   L   G   V   N   K   L   E   F   S   I   E   A   I   H   G   K   T ATA AAT GGT CAA GAG GCA GCC AAG TTC TTT CTT ATT GTC ATC CAA ATG GTT TCA
 I   N   G   Q   E   A   A   K   F   F   L   I   V   I   Q   M   V   S GAG GCA GCT CGG TTC AAA TAT ATT GAG ACT GAG GTG GTT GAT AGA GGA TTA TAT
 E   A   A   R   F   K   Y   I   E   T   E   V   V   D   R   G   L   Y GGA TCA TTC AAA CCT AAT TTT AAA GTA TTG AAC TTG GAG AAC AAT TGG GGC GAC
 G   S   F   K   P   N   F   K   V   L   N   L   E   N   N   W   G   D ATC TCT GAT GCC ATT CAC AAA TCA TCC CCA CAA TGT ACC ACT ATT AAT CCG GCA
 I   S   D   A   I   H   K   S   S   P   Q   C   T   T   I   N   P   A CTT CAG TTG ATA AGC CCC TCA AAT GAC CCA TGG GTT GTA AAT AAA GTG AGT CAA
 L   Q   L   I   S   P   S   N   D   P   W   V   V   N   K   V   S   Q ATT AGT CCC GAT ATG GGT ATC CTT AAG TTT AAA AGC TCC AAA TAG TGA CTC GAC
 I   S   P   D   M   G   I   L   K   F   K   S   S   K
                                               de-bouganin End ------------|

CTG CAG GTC TAT GGA ACG ATA AAT GCC CAT GAA AAT TCT ATT TCA AGG AGA CAG

TCA TA ATG AAA TAC CTA TTG CCT ACG GCA GCC GCT GGA TTG TTA TTA CTC GCT
          M   K   Y   L   L   P   T   A   A   A   G   L   L   L   L   A
       |_____PelB Leader Sequence_____

GCC CAA CCA GCG ATG GCG CAT CAC CAT CAC CAT CAC TCC TAT GAG CTG ACT CAG
 A   Q   P   A   M   A   H   H   H   H   H   H   S   Y   E   L   T   Q
_____| |-------- 6xHis ------| |----- V_L Start

CCA CCC TCA GTG TCC GTG TCC CCA GGA CAG ACA GCC AGC ATC ACC TGC TCT GGA
```

Continued Figure 11

```
    P   P   S   V   S   V   S   P   G   Q   T   A   S   I   T   C   S   G
                                                                   |—
GAT AAA TTG GGG GAT AAA TAT GCT TGC TGG TAT CAG CAG AAG CCA GGC CAG TCC
 D   K   L   G   D   K   Y   A   C   W   Y   Q   Q   K   P   G   Q   S
         |————————— CDR1 —————————|

CCT GTG CTG GTC ATC TAT CAA GAT AGC AAG CGG CCC TCA GGG ATC CCT GAG CGA
 P   V   L   V   I   Y   Q   D   S   K   R   P   S   G   I   P   E   R
                         |————————— CDR2 —————————|

TTC TCT GGC TCC AAC TCT GGG AAC ACA GCC ACT CTG ACC ATC AGC GGG ACC CAG
 F   S   G   S   N   S   G   N   T   A   T   L   T   I   S   G   T   Q

GCT ATG GAT GAG GCT GAC TAT TAC TGT CAG GCG TGG GAC AGC AGC ACT GTG GTA
 A   M   D   E   A   D   Y   Y   C   Q   A   W   D   S   S   T   V   V
                                     |————————— CDR3 —————————————————|

TTC GGC GGA GGG ACC AAG CTG ACC GTC CTA GGT CAG CCC AAG GCT GCC CCC TCG
 F   G   G   G   T   K   L   T   V   L   G   Q   P   K   A   A   P   S
                              V_L End ----||------ C_L Start GTC ACT CTG TTC CCG CCC TCC TCT GAG GAG CTC CAA GCC AAC AAG GCC ACA CTA
 V   T   L   F   P   P   S   S   E   E   L   Q   A   N   K   A   T   L GTG TGT CTG ATC AGT GAC TTC TAC CCG GGA GCT GTG ACA GTG GCC TGG AAG GCA
 V   C   L   I   S   D   F   Y   P   G   A   V   T   V   A   W   K   A GAT AGC AGC CCC GTC AAG GCG GGA GTG GAG ACC ACC ACA CCC TCC AAA CAG AGC
 D   S   S   P   V   K   A   G   V   E   T   T   T   P   S   K   Q   S AAC AAC AAG TAC GCG GCC AGC AGC TAC CTG AGC CTG ACG CCC GAG CAG TGG AAG
 N   N   K   Y   A   A   S   S   Y   L   S   L   T   P   E   Q   W   K TCC CAC ACA AGC TAC AGC TGC CAG GTC ACG CAT GAA GGG AGC ACC GTG GAG AAG
 S   H   R   S   Y   S   C   Q   V   T   H   E   G   S   T   V   E   K ACA GTG GCC CCT ACA GAA TGT TCA TAG TGA CTC GAG        (SEQ ID NO:66)
 T   V   A   P   T   E   C   S             (SEQ ID NO:67)
                         C_L End ---|
```

VB1-204 cytotoxic activity in CFPAC-1 cells

SEQUENCE LISTING

<160> NUMBER OF SEQ ID NOS: 72

<210> SEQ ID NO 1
<211> LENGTH: 381
<212> TYPE: DNA
<213> ORGANISM: Homo sapiens

<400> SEQUENCE: 1
gaggtgcagc tggtggagtc tgggggaggc gtggtccagc ctggggaggtc cctgagactc    60 tcctgtgcag cctctggatt caccttcagt agctatgcta tgcactgggt ccgccaggct   120
ccaggcaagg ggctggagtg ggtggcagtt atatcatatg atggaagtaa taatactac   180 gcagactccg tgaagggccg attcaccatc tccagagaca attccaagaa cacgctgtat   240
ctgcaaatga acagcctgag agctgaggac acggctgtgt attactgtgc gagagcacat   300

```
tcccgcttac tatggttcgg ggagttatta cccagcgctt ttgactactg gggccaggga    360
accctggtca ccgtctcctc a                                              381
```

<210> SEQ ID NO 2
<211> LENGTH: 127
<212> TYPE: PRT
<213> ORGANISM: Homo sapiens

<400> SEQUENCE: 2

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala His Ser Arg Leu Leu Trp Phe Gly Glu Leu Leu Pro Ser
            100                 105                 110

Ala Phe Asp Tyr Trp Gly Gln Gly Thr Leu Val Thr Val Ser Ser
        115                 120                 125
```

<210> SEQ ID NO 3
<211> LENGTH: 321
<212> TYPE: DNA
<213> ORGANISM: Homo sapiens

<400> SEQUENCE: 3

```
tcctatgagc tgactcagcc accctcagtg tccgtgtccc caggacagac agccagcatc     60
acctgctctg gagataaaatt gggggataaa tatgcttgct ggtatcagca gaagccaggc   120
cagtcccctg tgctggtcat ctatcaagat agcaagcggc cctcagggat ccctgagcga   180
ttctctggct ccaactctgg gaacacagcc actctgacca tcagcgggac ccaggctatg   240
gatgaggctg actattactg tcaggcgtgg gacagcagca ctgtggtatt cggcggaggg   300
accaagctga ccgtcctagg t                                              321
```

<210> SEQ ID NO 4
<211> LENGTH: 107
<212> TYPE: PRT
<213> ORGANISM: Homo sapiens

<400> SEQUENCE: 4

```
Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80
```

```
Asp Glu Ala Asp Tyr Tyr Cys Gln Ala Trp Asp Ser Ser Thr Val Val
            85                  90                  95

Phe Gly Gly Gly Thr Lys Leu Thr Val Leu Gly
            100                 105
```

<210> SEQ ID NO 5
<211> LENGTH: 5
<212> TYPE: PRT
<213> ORGANISM: Homo sapiens

<400> SEQUENCE: 5

```
Ser Tyr Ala Met His
1               5
```

<210> SEQ ID NO 6
<211> LENGTH: 17
<212> TYPE: PRT
<213> ORGANISM: Homo sapiens

<400> SEQUENCE: 6

```
Val Ile Ser Tyr Asp Gly Ser Asn Lys Tyr Tyr Ala Asp Ser Val Lys
1               5                   10                  15

Gly
```

<210> SEQ ID NO 7
<211> LENGTH: 18
<212> TYPE: PRT
<213> ORGANISM: Homo sapiens

<400> SEQUENCE: 7

```
Ala His Ser Arg Leu Leu Trp Phe Gly Glu Leu Leu Pro Ser Ala Phe
1               5                   10                  15

Asp Tyr
```

<210> SEQ ID NO 8
<211> LENGTH: 11
<212> TYPE: PRT
<213> ORGANISM: Homo sapiens

<400> SEQUENCE: 8

```
Ser Gly Asp Lys Leu Gly Asp Lys Tyr Ala Cys
1               5                   10
```

<210> SEQ ID NO 9
<211> LENGTH: 7
<212> TYPE: PRT
<213> ORGANISM: Homo sapiens

<400> SEQUENCE: 9

```
Gln Asp Ser Lys Arg Pro Ser
1               5
```

<210> SEQ ID NO 10
<211> LENGTH: 9
<212> TYPE: PRT
<213> ORGANISM: Homo sapiens

<400> SEQUENCE: 10

```
Gln Ala Trp Asp Ser Ser Thr Val Val
1               5
```

<210> SEQ ID NO 11
<211> LENGTH: 250

<212> TYPE: PRT
<213> ORGANISM: Bougainvillea spectabilis

<400> SEQUENCE: 11

```
Tyr Asn Thr Val Ser Phe Asn Leu Gly Glu Ala Tyr Glu Tyr Pro Thr
1               5                   10                  15

Phe Ile Gln Asp Leu Arg Asn Glu Leu Ala Lys Gly Thr Pro Val Cys
            20                  25                  30

Gln Leu Pro Val Thr Leu Gln Thr Ile Ala Asp Lys Arg Phe Val
        35                  40                  45

Leu Val Asp Ile Thr Thr Thr Ser Lys Lys Thr Val Lys Val Ala Ile
50                  55                  60

Asp Val Thr Asp Val Tyr Val Val Gly Tyr Gln Asp Lys Trp Asp Gly
65                  70                  75                  80

Lys Asp Arg Ala Val Phe Leu Asp Lys Val Pro Thr Val Ala Thr Ser
                85                  90                  95

Lys Leu Phe Pro Gly Val Thr Asn Arg Val Thr Leu Thr Phe Asp Gly
            100                 105                 110

Ser Tyr Gln Lys Leu Val Asn Ala Ala Lys Ala Asp Arg Lys Ala Leu
        115                 120                 125

Glu Leu Gly Val Asn Lys Leu Glu Phe Ser Ile Glu Ala Ile His Gly
130                 135                 140

Lys Thr Ile Asn Gly Gln Glu Ala Ala Lys Phe Phe Leu Ile Val Ile
145                 150                 155                 160

Gln Met Val Ser Glu Ala Ala Arg Phe Lys Tyr Ile Glu Thr Glu Val
                165                 170                 175

Val Asp Arg Gly Leu Tyr Gly Ser Phe Lys Pro Asn Phe Lys Val Leu
            180                 185                 190

Asn Leu Glu Asn Asn Trp Gly Asp Ile Ser Asp Ala Ile His Lys Ser
        195                 200                 205

Ser Pro Gln Cys Thr Thr Ile Asn Pro Ala Leu Gln Leu Ile Ser Pro
    210                 215                 220

Ser Asn Asp Pro Trp Val Val Asn Lys Val Ser Gln Ile Ser Pro Asp
225                 230                 235                 240

Met Gly Ile Leu Lys Phe Lys Ser Ser Lys
                245                 250
```

<210> SEQ ID NO 12
<211> LENGTH: 34
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (16)..(16)
<223> OTHER INFORMATION: r= a or g
<220> FEATURE:
<221> NAME/KEY: misc_feature
<222> LOCATION: (30)..(30)
<223> OTHER INFORMATION: r= a or g

<400> SEQUENCE: 12
ccagccatgg cgcagrtgca gctggtgcar tctg         34

<210> SEQ ID NO 13
<211> LENGTH: 35
<212> TYPE: DNA
<213> ORGANISM: Artificial Sequence
<220> FEATURE:

```
<223> OTHER INFORMATION: primer
<220> FEATURE:
<221> NAME/KEY: misc_feature
<222> LOCATION: (13)..(13)
<223> OTHER INFORMATION: s= c or g
<220> FEATURE:
<221> NAME/KEY: misc_feature
<222> LOCATION: (27)..(27)
<223> OTHER INFORMATION: r= a or g

<400> SEQUENCE: 13
ccagccatgg cgsaggtcca gctggtrcag tctgg                              35

<210> SEQ ID NO 14
<211> LENGTH: 35
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (16)..(16)
<223> OTHER INFORMATION: r= a or g

<400> SEQUENCE: 14
ccagccatgg cgcagrtcac cttgaaggag tctgg                              35

<210> SEQ ID NO 15
<211> LENGTH: 35
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (13)..(13)
<223> OTHER INFORMATION: s= c or g

<400> SEQUENCE: 15
ccagccatgg cgsaggtgca gctggtggag tctgg                              35

<210> SEQ ID NO 16
<211> LENGTH: 35
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (31)..(31)
<223> OTHER INFORMATION: w= a or t
<220> FEATURE:
<221> NAME/KEY: misc_feature
<222> LOCATION: (33)..(33)
<223> OTHER INFORMATION: y=  c or t

<400> SEQUENCE: 16
ccagccatgg cggaggtgca gctggtggag wcygg                              35

<210> SEQ ID NO 17
<211> LENGTH: 35
<212> TYPE: DNA
<213> ORGANISM: Artificial Sequence
<220> FEATURE:
<223> OTHER INFORMATION: primer

<400> SEQUENCE: 17
ccagccatgg cgcaggtgca gctacagcag tgggg                              35
```

```
<210> SEQ ID NO 18
<211> LENGTH: 35
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (16)..(16)
<223> OTHER INFORMATION: s= c or g
<220> FEATURE:
<221> NAME/KEY: misc_feature
<222> LOCATION: (33)..(33)
<223> OTHER INFORMATION: s= c or g

<400> SEQUENCE: 18
ccagccatgg cgcagstgca gctgcaggag tcsgg                              35

<210> SEQ ID NO 19
<211> LENGTH: 38
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (18)..(18)
<223> OTHER INFORMATION: r= a or g

<400> SEQUENCE: 19
ccagccatgg cgcaggargt gcagctggtg cagtctgg                           38

<210> SEQ ID NO 20
<211> LENGTH: 38
<212> TYPE: DNA
<213> ORGANISM: Artificial Sequence
<220> FEATURE:
<223> OTHER INFORMATION: primer

<400> SEQUENCE: 20
ccagccatgg cgcagcaggt acagctgcag cagtcagg                           38

<210> SEQ ID NO 21
<211> LENGTH: 42
<212> TYPE: DNA
<213> ORGANISM: Artificial Sequence
<220> FEATURE:
<223> OTHER INFORMATION: primer

<400> SEQUENCE: 21
ccaggagaaa gtgatggagt cgggaaggaa gtcctgtgcg ag                      42

<210> SEQ ID NO 22
<211> LENGTH: 42
<212> TYPE: DNA
<213> ORGANISM: Artificial Sequence
<220> FEATURE:
<223> OTHER INFORMATION: primer

<400> SEQUENCE: 22
cgacggggaa ttctcacagg agacgagggg gaaaagggtt gg                      42

<210> SEQ ID NO 23
<211> LENGTH: 27
<212> TYPE: DNA
<213> ORGANISM: Artificial Sequence
<220> FEATURE:
<223> OTHER INFORMATION: primer
<220> FEATURE:
```

```
<221> NAME/KEY: misc_feature
<222> LOCATION: (9)..(9)
<223> OTHER INFORMATION: s= c or g
<220> FEATURE:
<221> NAME/KEY: misc_feature
<222> LOCATION: (10)..(10)
<223> OTHER INFORMATION: w= a or t
<220> FEATURE:
<221> NAME/KEY: misc_feature
<222> LOCATION: (12)..(12)
<223> OTHER INFORMATION: y= c or t
<220> FEATURE:
<221> NAME/KEY: misc_feature
<222> LOCATION: (19)..(19)
<223> OTHER INFORMATION: y= c or t
<220> FEATURE:
<221> NAME/KEY: misc_feature
<222> LOCATION: (26)..(26)
<223> OTHER INFORMATION: y= c or t

<400> SEQUENCE: 23
atggcctgsw cycctctcyt cctcayc                                           27

<210> SEQ ID NO 24
<211> LENGTH: 27
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (15)..(15)
<223> OTHER INFORMATION: s= c or g
<220> FEATURE:
<221> NAME/KEY: misc_feature
<222> LOCATION: (16)..(16)
<223> OTHER INFORMATION: y= c or t
<220> FEATURE:
<221> NAME/KEY: misc_feature
<222> LOCATION: (18)..(18)
<223> OTHER INFORMATION: k= t or g
<220> FEATURE:
<221> NAME/KEY: misc_feature
<222> LOCATION: (19)..(19)
<223> OTHER INFORMATION: y= c or t
<220> FEATURE:
<221> NAME/KEY: misc_feature
<222> LOCATION: (21)..(21)
<223> OTHER INFORMATION: s= c or g
<220> FEATURE:
<221> NAME/KEY: misc_feature
<222> LOCATION: (22)..(22)
<223> OTHER INFORMATION: y= c or t
<220> FEATURE:
<221> NAME/KEY: misc_feature
<222> LOCATION: (26)..(26)
<223> OTHER INFORMATION: s= c or g

<400> SEQUENCE: 24
atggcctggg ctctsytkyt sytcasc                                           27

<210> SEQ ID NO 25
<211> LENGTH: 27
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (6)..(6)
<223> OTHER INFORMATION: m= a or c
<220> FEATURE:
<221> NAME/KEY: misc_feature
<222> LOCATION: (11)..(11)
<223> OTHER INFORMATION: y= c or t
```

```
<220> FEATURE:
<221> NAME/KEY: misc_feature
<222> LOCATION: (13)..(13)
<223> OTHER INFORMATION: s= c or g
<220> FEATURE:
<221> NAME/KEY: misc_feature
<222> LOCATION: (14)..(14)
<223> OTHER INFORMATION: y= c or t
<220> FEATURE:
<221> NAME/KEY: misc_feature
<222> LOCATION: (19)..(19)
<223> OTHER INFORMATION: y= c or t

<400> SEQUENCE: 25
atggcmtgga ycsytctcyt cctcggc                                          27

<210> SEQ ID NO 26
<211> LENGTH: 42
<212> TYPE: DNA
<213> ORGANISM: Artificial Sequence
<220> FEATURE:
<223> OTHER INFORMATION: primer

<400> SEQUENCE: 26
cactagtgtg gccttgttgg cttggacctc ctcagaggag gg                         42

<210> SEQ ID NO 27
<211> LENGTH: 338
<212> TYPE: PRT
<213> ORGANISM: Homo sapiens

<400> SEQUENCE: 27
```

Met Ala Gly Val Ala Cys Leu Gly Lys Ala Ala Asp Ala Asp Glu Trp
1               5                   10                  15

Cys Asp Thr Gly Leu Gly Ser Leu Gly Pro Asp Ala Ala Ala Pro Gly
            20                  25                  30

Gly Pro Gly Leu Gly Ala Glu Leu Gly Pro Gly Leu Ser Trp Ala Pro
        35                  40                  45

Leu Val Phe Gly Tyr Val Thr Glu Asp Gly Asp Thr Ala Leu His Leu
    50                  55                  60

Ala Val Ile His Gln His Glu Pro Phe Leu Asp Phe Leu Leu Gly Phe
65                  70                  75                  80

Ser Ala Gly Thr Glu Tyr Met Asp Leu Gln Asn Asp Leu Gly Gln Thr
                85                  90                  95

Ala Leu His Leu Ala Ala Ile Leu Gly Glu Thr Ser Thr Val Glu Lys
            100                 105                 110

Leu Tyr Ala Ala Gly Ala Gly Leu Cys Val Ala Glu Arg Arg Gly His
        115                 120                 125

Thr Ala Leu His Leu Ala Cys Arg Val Gly Ala His Ala Cys Ala Arg
    130                 135                 140

Ala Leu Leu Gln Pro Arg Pro Arg Arg Pro Arg Glu Ala Pro Asp Thr
145                 150                 155                 160

Tyr Leu Ala Gln Gly Pro Asp Arg Thr Pro Asp Thr Asn His Thr Pro
                165                 170                 175

Val Ala Leu Tyr Pro Asp Ser Asp Leu Glu Lys Glu Glu Glu Glu Ser
            180                 185                 190

Glu Glu Asp Trp Lys Leu Gln Leu Glu Ala Glu Asn Tyr Glu Gly His
        195                 200                 205

Thr Pro Leu His Val Ala Val Ile His Lys Asp Val Glu Met Val Arg
    210                 215                 220

```
Leu Leu Arg Asp Ala Gly Ala Asp Leu Asp Lys Pro Glu Pro Thr Cys
225                 230                 235                 240

Gly Arg Ser Pro Leu His Leu Ala Val Glu Ala Gln Ala Ala Asp Val
            245                 250                 255

Leu Glu Leu Leu Leu Arg Ala Gly Ala Asn Pro Ala Ala Arg Met Tyr
        260                 265                 270

Gly Gly Arg Thr Pro Leu Gly Ser Ala Met Leu Arg Pro Asn Pro Ile
        275                 280                 285

Leu Ala Arg Leu Leu Arg Ala His Gly Ala Pro Glu Pro Glu Gly Glu
        290                 295                 300

Asp Glu Lys Ser Gly Pro Cys Ser Ser Ser Asp Ser Asp Gly Gly
305                 310                 315                 320

Asp Glu Gly Val Ser Gln Glu Glu Arg Gln Gly Ser Pro Ala Gly Gly
                325                 330                 335

Ser Gly

<210> SEQ ID NO 28
<211> LENGTH: 355
<212> TYPE: PRT
<213> ORGANISM: Homo sapiens

<400> SEQUENCE: 28

Met Ala Gly Val Ala Cys Leu Gly Lys Ala Ala Asp Ala Asp Glu Trp
1               5                   10                  15

Cys Asp Ser Gly Leu Gly Ser Leu Gly Pro Asp Ala Ala Ala Pro Gly
            20                  25                  30

Gly Pro Gly Leu Gly Ala Glu Leu Gly Pro Gly Leu Ser Trp Ala Pro
        35                  40                  45

Leu Val Phe Gly Tyr Val Thr Glu Asp Gly Asp Thr Ala Leu His Leu
    50                  55                  60

Ala Val Ile His Gln His Glu Pro Phe Leu Asp Phe Leu Leu Gly Phe
65                  70                  75                  80

Ser Ala Gly Thr Glu Tyr Met Asp Leu Gln Asn Asp Leu Gly Gln Thr
                85                  90                  95

Ala Leu His Leu Ala Ala Ile Leu Gly Glu Thr Ser Thr Val Glu Lys
            100                 105                 110

Leu Tyr Ala Ala Gly Ala Gly Leu Cys Val Ala Glu Arg Arg Gly His
        115                 120                 125

Thr Ala Leu His Leu Ala Cys Arg Val Gly Ala His Ala Cys Ala Arg
    130                 135                 140

Ala Leu Leu Gln Pro Arg Pro Arg Arg Pro Arg Glu Ala Pro Asp Thr
145                 150                 155                 160

Tyr Leu Ala Gln Gly Pro Asp Arg Thr Pro Asp Thr Asn His Thr Pro
                165                 170                 175

Val Ala Leu Tyr Pro Asp Ser Asp Leu Glu Lys Glu Glu Glu Glu Ser
            180                 185                 190

Glu Glu Asp Trp Lys Leu Gln Leu Glu Ala Glu Asn Tyr Glu Gly His
        195                 200                 205

Thr Pro Leu His Val Ala Val Ile His Lys Asp Val Glu Met Val Arg
    210                 215                 220

Leu Leu Arg Asp Ala Gly Ala Asp Leu Asp Lys Pro Glu Pro Thr Cys
225                 230                 235                 240

Gly Arg Ser Pro Leu His Leu Ala Val Glu Ala Gln Ala Ala Asp Val
                245                 250                 255
```

```
Leu Glu Leu Leu Leu Arg Ala Gly Ala Asn Pro Ala Ala Arg Met Tyr
            260                 265                 270

Gly Gly Arg Thr Pro Leu Gly Ser Ala Met Leu Arg Pro Asn Pro Ile
            275                 280                 285

Leu Ala Arg Leu Leu Arg Ala His Gly Ala Pro Glu Pro Glu Gly Glu
            290                 295                 300

Asp Glu Lys Ser Gly Pro Cys Ser Ser Ser Asp Ser Asp Ser Gly
305                 310                 315                 320

Asp Glu Gly Asp Glu Tyr Asp Asp Ile Val Val His Ser Ser Arg Ser
                325                 330                 335

Gln Thr Arg Leu Pro Pro Thr Pro Ala Ser Lys Pro Leu Pro Asp Asp
            340                 345                 350

Pro Arg Pro
       355

<210> SEQ ID NO 29
<211> LENGTH: 361
<212> TYPE: PRT
<213> ORGANISM: Homo sapiens

<400> SEQUENCE: 29

Leu Gln Asn Ser Arg Gln Ser Pro Ala Thr Gly Gly Arg Leu Arg Gly
1               5                   10                  15

Ala Pro Glu Ala Ala Gly Ala Met Ala Gly Val Ala Cys Leu Gly Lys
            20                  25                  30

Ala Ala Asp Ala Asp Glu Trp Cys Asp Ser Gly Leu Gly Ser Leu Gly
        35                  40                  45

Pro Asp Ala Ala Ala Pro Gly Gly Pro Gly Leu Gly Ala Glu Leu Gly
50                  55                  60

Pro Gly Leu Ser Trp Ala Pro Leu Val Phe Gly Tyr Val Thr Glu Asp
65                  70                  75                  80

Gly Asp Thr Ala Leu His Leu Ala Val Ile His Gln His Glu Pro Phe
                85                  90                  95

Leu Asp Phe Leu Leu Gly Phe Ser Ala Gly Thr Glu Tyr Met Asp Leu
            100                 105                 110

Gln Asn Asp Leu Gly Gln Thr Ala Leu His Leu Ala Ala Ile Leu Gly
        115                 120                 125

Glu Thr Ser Thr Val Glu Lys Leu Tyr Ala Ala Gly Ala Gly Leu Cys
130                 135                 140

Val Ala Glu Arg Arg Gly His Thr Ala Leu His Leu Ala Cys Arg Val
145                 150                 155                 160

Gly Ala His Ala Cys Ala Arg Ala Leu Leu Gln Pro Arg Pro Arg Arg
                165                 170                 175

Pro Arg Glu Ala Pro Asp Thr Tyr Leu Ala Gln Gly Pro Asp Arg Thr
            180                 185                 190

Pro Asp Thr Asn His Thr Pro Val Ala Leu Tyr Pro Asp Ser Asp Leu
        195                 200                 205

Glu Lys Glu Glu Glu Ser Glu Glu Asp Trp Lys Leu Gln Leu Glu
210                 215                 220

Ala Glu Asn Tyr Glu Gly His Thr Pro Leu His Val Ala Val Ile His
225                 230                 235                 240

Lys Asp Val Glu Met Val Arg Leu Leu Arg Asp Ala Gly Ala Asp Leu
                245                 250                 255

Asp Lys Pro Glu Pro Thr Cys Gly Arg Ser Pro Leu His Leu Ala Val
            260                 265                 270
```

```
Glu Ala Gln Ala Ala Asp Val Leu Glu Leu Leu Arg Ala Gly Ala
        275                 280                 285

Asn Pro Ala Ala Arg Met Tyr Gly Gly Arg Thr Pro Leu Gly Ser Ala
290                 295                 300

Met Leu Arg Pro Asn Pro Ile Leu Ala Arg Leu Leu Arg Ala His Gly
305                 310                 315                 320

Ala Pro Glu Pro Glu Gly Glu Asp Glu Lys Ser Gly Pro Cys Ser Ser
                325                 330                 335

Ser Ser Asp Ser Asp Ser Gly Asp Glu Gly Val Ser Gln Glu Glu Arg
            340                 345                 350

Gln Gly Ser Pro Ala Gly Gly Ser Gly
            355                 360

<210> SEQ ID NO 30
<211> LENGTH: 338
<212> TYPE: PRT
<213> ORGANISM: Homo sapiens

<400> SEQUENCE: 30

Met Ala Gly Val Ala Cys Leu Gly Lys Ala Ala Asp Ala Asp Glu Trp
1               5                   10                  15

Cys Asp Thr Gly Leu Gly Ser Leu Gly Val Leu Ala Ala Ala Val Gly
            20                  25                  30

Gly Val Gly Leu Gly Ala Trp Leu Gly Pro Gly Leu Ser Trp Ala Pro
        35                  40                  45

Leu Val Phe Gly Tyr Val Thr Glu Asp Gly Asp Thr Ala Leu His Leu
    50                  55                  60

Ala Val Ile His Gln His Glu Pro Phe Leu Asp Phe Leu Leu Gly Phe
65                  70                  75                  80

Ser Ala Gly Thr Glu Tyr Met Asp Leu Gln Asn Asp Leu Gly Gln Thr
                85                  90                  95

Ala Leu His Leu Ala Ala Ile Leu Gly Val Thr Ser Thr Val Val Ala
            100                 105                 110

Leu Tyr Ala Ala Gly Ala Gly Leu Cys Val Ala Glu Arg Arg Gly His
        115                 120                 125

Thr Ala Leu His Leu Ala Cys Arg Val Gly Ala His Ala Cys Ala Arg
    130                 135                 140

Ala Leu Leu Gln Pro Arg Pro Arg Arg Pro Arg Glu Ala Pro Asp Thr
145                 150                 155                 160

Tyr Leu Ala Gln Gly Pro Asp Arg Thr Pro Asp Thr Asn His Thr Pro
                165                 170                 175

Val Ala Leu Tyr Pro Asp Ser Asp Leu Glu Lys Glu Glu Glu Glu Ser
            180                 185                 190

Glu Glu Asp Trp Lys Leu Gln Leu Glu Ala Glu Asn Tyr Glu Gly His
        195                 200                 205

Thr Pro Leu His Val Ala Val Ile His Lys Asp Val Glu Met Val Arg
    210                 215                 220

Leu Leu Arg Asp Ala Gly Ala Asp Leu Asp Lys Pro Glu Pro Thr Cys
225                 230                 235                 240

Gly Arg Ser Pro Leu His Leu Ala Val Glu Ala Gln Ala Ala Asp Val
                245                 250                 255

Leu Glu Leu Leu Leu Arg Ala Gly Ala Asn Pro Ala Ala Arg Met Tyr
            260                 265                 270

Gly Gly Arg Thr Pro Leu Gly Ser Ala Met Leu Arg Pro Asn Pro Ile
```

```
                 275                 280                 285
Leu Ala Arg Leu Leu Arg Ala His Gly Ala Pro Glu Pro Glu Gly Glu
             290                 295                 300

Asp Glu Lys Ser Gly Pro Cys Ser Ser Ser Asp Ser Asp Gly Gly
305                 310                 315                 320

Asp Glu Gly Val Ser Gln Glu Leu Arg Gln Gly Ser Pro Ala Gly Gly
                325                 330                 335

Ser Gly

<210> SEQ ID NO 31
<211> LENGTH: 9
<212> TYPE: PRT
<213> ORGANISM: Homo sapiens

<400> SEQUENCE: 31

Met Ala Gly Val Ala Cys Leu Gly Lys
1               5

<210> SEQ ID NO 32
<211> LENGTH: 30
<212> TYPE: PRT
<213> ORGANISM: Homo sapiens

<400> SEQUENCE: 32

Ala Asp Glu Trp Cys Asp Thr Gly Leu Gly Ser Leu Gly Val Leu Ala
1               5                   10                  15

Ala Ala Val Gly Gly Val Gly Leu Gly Ala Trp Leu Gly Pro
            20                  25                  30

<210> SEQ ID NO 33
<211> LENGTH: 34
<212> TYPE: PRT
<213> ORGANISM: Homo sapiens

<400> SEQUENCE: 33

Glu Trp Cys Asp Thr Gly Leu Gly Ser Leu Gly Val Leu Ala Ala Ala
1               5                   10                  15

Val Gly Gly Val Gly Leu Gly Ala Trp Leu Gly Pro Gly Leu Ser Trp
            20                  25                  30

Ala Pro

<210> SEQ ID NO 34
<211> LENGTH: 17
<212> TYPE: PRT
<213> ORGANISM: Homo sapiens

<400> SEQUENCE: 34

Leu Gly Val Leu Ala Ala Ala Val Gly Gly Val Gly Leu Gly Ala Trp
1               5                   10                  15

Leu

<210> SEQ ID NO 35
<211> LENGTH: 11
<212> TYPE: PRT
<213> ORGANISM: Homo sapiens

<400> SEQUENCE: 35

Phe Leu Leu Gly Phe Ser Ala Gly Thr Glu Tyr
1               5                   10
```

```
<210> SEQ ID NO 36
<211> LENGTH: 62
<212> TYPE: PRT
<213> ORGANISM: Homo sapiens

<400> SEQUENCE: 36

Leu Gly Gln Thr Ala Leu His Leu Ala Ala Ile Leu Gly Val Thr Ser
 1               5                  10                  15

Thr Val Val Ala Leu Tyr Ala Ala Gly Ala Gly Leu Cys Val Ala Glu
            20                  25                  30

Arg Arg Gly His Thr Ala Leu His Leu Ala Cys Arg Val Gly Ala His
        35                  40                  45

Ala Cys Ala Arg Ala Leu Leu Gln Pro Arg Pro Arg Arg Pro
    50                  55                  60

<210> SEQ ID NO 37
<211> LENGTH: 11
<212> TYPE: PRT
<213> ORGANISM: Homo sapiens

<400> SEQUENCE: 37

Ile Leu Gly Val Thr Ser Thr Val Val Ala Leu
 1               5                  10

<210> SEQ ID NO 38
<211> LENGTH: 13
<212> TYPE: PRT
<213> ORGANISM: Homo sapiens

<400> SEQUENCE: 38

Leu Tyr Ala Ala Gly Ala Gly Leu Cys Val Ala Glu Arg
 1               5                  10

<210> SEQ ID NO 39
<211> LENGTH: 8
<212> TYPE: PRT
<213> ORGANISM: Homo sapiens

<400> SEQUENCE: 39

Val Gly Ala His Ala Cys Ala Arg
 1               5

<210> SEQ ID NO 40
<211> LENGTH: 8
<212> TYPE: PRT
<213> ORGANISM: Homo sapiens

<400> SEQUENCE: 40

Ala Leu Leu Gln Pro Arg Pro Arg
 1               5

<210> SEQ ID NO 41
<211> LENGTH: 13
<212> TYPE: PRT
<213> ORGANISM: Homo sapiens

<400> SEQUENCE: 41

Glu Ala Pro Asp Thr Tyr Leu Ala Gln Gly Pro Asp Arg
 1               5                  10

<210> SEQ ID NO 42
<211> LENGTH: 19
<212> TYPE: PRT
<213> ORGANISM: Homo sapiens
```

```
<400> SEQUENCE: 42

Thr Pro Asp Thr Asn His Thr Pro Val Ala Leu Tyr Pro Asp Ser Asp
1               5                   10                  15

Leu Glu Lys

<210> SEQ ID NO 43
<211> LENGTH: 10
<212> TYPE: PRT
<213> ORGANISM: Homo sapiens

<400> SEQUENCE: 43

Glu Glu Glu Glu Ser Glu Glu Asp Trp Lys
1               5                   10

<210> SEQ ID NO 44
<211> LENGTH: 21
<212> TYPE: PRT
<213> ORGANISM: Homo sapiens

<400> SEQUENCE: 44

Leu Gln Leu Glu Ala Glu Asn Tyr Glu Gly His Thr Pro Leu His Val
1               5                   10                  15

Ala Val Ile His Lys
            20

<210> SEQ ID NO 45
<211> LENGTH: 6
<212> TYPE: PRT
<213> ORGANISM: Homo sapiens

<400> SEQUENCE: 45

Asp Val Glu Met Val Arg
1               5

<210> SEQ ID NO 46
<211> LENGTH: 15
<212> TYPE: PRT
<213> ORGANISM: Homo sapiens

<400> SEQUENCE: 46

Asp Ala Gly Ala Asp Leu Asp Lys Pro Glu Pro Thr Cys Gly Arg
1               5                   10                  15

<210> SEQ ID NO 47
<211> LENGTH: 20
<212> TYPE: PRT
<213> ORGANISM: Homo sapiens

<400> SEQUENCE: 47

Ser Pro Leu His Leu Ala Val Glu Ala Gln Ala Ala Asp Val Leu Glu
1               5                   10                  15

Leu Leu Leu Arg
            20

<210> SEQ ID NO 48
<211> LENGTH: 8
<212> TYPE: PRT
<213> ORGANISM: Homo sapiens

<400> SEQUENCE: 48

Ala Gly Ala Asn Pro Ala Ala Arg
1               5
```

<210> SEQ ID NO 49
<211> LENGTH: 16
<212> TYPE: PRT
<213> ORGANISM: Homo sapiens

<400> SEQUENCE: 49

Thr Pro Leu Gly Ser Ala Met Leu Arg Pro Asn Pro Ile Leu Ala Arg
1               5                   10                  15

<210> SEQ ID NO 50
<211> LENGTH: 13
<212> TYPE: PRT
<213> ORGANISM: Homo sapiens

<400> SEQUENCE: 50

Ala His Gly Ala Pro Glu Pro Glu Gly Glu Asp Glu Lys
1               5                   10

<210> SEQ ID NO 51
<211> LENGTH: 22
<212> TYPE: PRT
<213> ORGANISM: Homo sapiens

<400> SEQUENCE: 51

Ser Gly Pro Cys Ser Ser Ser Asp Ser Asp Gly Gly Asp Glu Gly
1               5                   10                  15

Val Ser Gln Glu Glu Arg
            20

<210> SEQ ID NO 52
<211> LENGTH: 9
<212> TYPE: PRT
<213> ORGANISM: Homo sapiens

<400> SEQUENCE: 52

Gln Gly Ser Pro Ala Gly Gly Ser Gly
1               5

<210> SEQ ID NO 53
<211> LENGTH: 23
<212> TYPE: PRT
<213> ORGANISM: Homo sapiens

<400> SEQUENCE: 53

Leu Gly Ser Leu Gly Val Leu Ala Ala Val Gly Gly Val Gly Leu
1               5                   10                  15

Gly Ala Trp Leu Gly Pro Gly
            20

<210> SEQ ID NO 54
<211> LENGTH: 23
<212> TYPE: PRT
<213> ORGANISM: Homo sapiens

<400> SEQUENCE: 54

Leu Ala Ala Ile Leu Gly Val Thr Ser Thr Val Val Ala Leu Tyr Ala
1               5                   10                  15

Ala Gly Ala Gly Leu Cys Val
            20

<210> SEQ ID NO 55
<211> LENGTH: 338

<212> TYPE: PRT
<213> ORGANISM: Homo sapiens

<400> SEQUENCE: 55

Met Ala Gly Val Ala Cys Leu Gly Lys Ala Ala Asp Ala Asp Glu Trp
1               5                   10                  15

Cys Asp Thr Gly Leu Gly Ser Leu Gly Pro Asp Ala Ala Pro Gly
            20                  25                  30

Gly Pro Gly Leu Gly Ala Glu Leu Gly Pro Gly Leu Ser Trp Ala Pro
        35                  40                  45

Leu Val Phe Gly Tyr Val Thr Glu Asp Gly Asp Thr Ala Leu His Leu
    50                  55                  60

Ala Val Ile His Gln His Glu Pro Phe Leu Asp Phe Leu Leu Gly Phe
65                  70                  75                  80

Ser Ala Gly Thr Glu Tyr Met Asp Leu Gln Asn Asp Leu Gly Gln Thr
                85                  90                  95

Ala Leu His Leu Ala Ala Ile Leu Gly Glu Thr Ser Thr Val Glu Lys
            100                 105                 110

Leu Tyr Ala Ala Gly Ala Gly Leu Cys Val Ala Glu Arg Arg Gly His
        115                 120                 125

Thr Ala Leu His Leu Ala Cys Arg Val Gly Ala His Ala Cys Ala Arg
    130                 135                 140

Ala Leu Leu Gln Pro Arg Pro Arg Arg Pro Arg Glu Ala Pro Asp Thr
145                 150                 155                 160

Tyr Leu Ala Gln Gly Pro Asp Arg Thr Pro Thr Asn His Thr Pro
                165                 170                 175

Val Ala Leu Tyr Pro Asp Ser Asp Leu Glu Lys Glu Glu Glu Ser
            180                 185                 190

Glu Glu Asp Trp Lys Leu Gln Leu Glu Ala Glu Asn Tyr Glu Gly His
        195                 200                 205

Thr Pro Leu His Val Ala Val Ile His Lys Asp Val Glu Met Val Arg
    210                 215                 220

Leu Leu Arg Asp Ala Gly Ala Asp Leu Asp Lys Pro Glu Pro Thr Cys
225                 230                 235                 240

Gly Arg Ser Pro Leu His Leu Ala Val Glu Ala Gln Ala Ala Asp Val
                245                 250                 255

Leu Glu Leu Leu Leu Arg Ala Gly Ala Asn Pro Ala Ala Arg Met Tyr
            260                 265                 270

Gly Gly Arg Thr Pro Leu Gly Ser Ala Met Leu Arg Pro Asn Pro Ile
        275                 280                 285

Leu Ala Arg Leu Leu Arg Ala His Gly Ala Pro Glu Pro Glu Gly Glu
    290                 295                 300

Asp Glu Lys Ser Gly Pro Cys Ser Ser Ser Asp Ser Asp Gly Gly
305                 310                 315                 320

Asp Glu Gly Val Ser Gln Glu Glu Arg Gln Gly Ser Pro Ala Gly Gly
                325                 330                 335

Ser Gly

<210> SEQ ID NO 56
<211> LENGTH: 33
<212> TYPE: DNA
<213> ORGANISM: Artificial Sequence
<220> FEATURE:
<223> OTHER INFORMATION: primer

<400> SEQUENCE: 56
gaattccctg caggtctatg aacgataaa tgc        33

<210> SEQ ID NO 57
<211> LENGTH: 36
<212> TYPE: DNA
<213> ORGANISM: Artificial Sequence
<220> FEATURE:
<223> OTHER INFORMATION: primer

<400> SEQUENCE: 57
cgccatcgct ggttgggcag cgagtaataa caatcc        36

<210> SEQ ID NO 58
<211> LENGTH: 45
<212> TYPE: DNA
<213> ORGANISM: Artificial Sequence
<220> FEATURE:
<223> OTHER INFORMATION: primer

<400> SEQUENCE: 58
gctgcccaac cagcgatggc ggaggtgcag ctggtggagt ctggg        45

<210> SEQ ID NO 59
<211> LENGTH: 45
<212> TYPE: DNA
<213> ORGANISM: Artificial Sequence
<220> FEATURE:
<223> OTHER INFORMATION: primer

<400> SEQUENCE: 59
gaccgatggg cccttggtgg aggctgagga gacggtgacc agggt        45

<210> SEQ ID NO 60
<211> LENGTH: 42
<212> TYPE: DNA
<213> ORGANISM: Artificial Sequence
<220> FEATURE:
<223> OTHER INFORMATION: primer

<400> SEQUENCE: 60
atccttaagt ttaaaagctc caaatagtga tctagagtcg ac        42

<210> SEQ ID NO 61
<211> LENGTH: 30
<212> TYPE: DNA
<213> ORGANISM: Artificial Sequence
<220> FEATURE:
<223> OTHER INFORMATION: primer

<400> SEQUENCE: 61
gtgatggtga tggtgatgcg ccatcgctgg        30

<210> SEQ ID NO 62
<211> LENGTH: 48
<212> TYPE: DNA
<213> ORGANISM: Artificial Sequence
<220> FEATURE:
<223> OTHER INFORMATION: primer

<400> SEQUENCE: 62
atggcgcatc accatcacca tcactcctat gagctgactc agccaccc        48

<210> SEQ ID NO 63
<211> LENGTH: 48
<212> TYPE: DNA

<210> SEQ ID NO 63
<211> LENGTH: 48 (implied)
<213> ORGANISM: Artificial Sequence
<220> FEATURE:
<223> OTHER INFORMATION: primer

<400> SEQUENCE: 63
gaccgagggg gcagccttgg gctgacctag gacggtcagc ttggtccc                48

<210> SEQ ID NO 64
<211> LENGTH: 33
<212> TYPE: DNA
<213> ORGANISM: Artificial Sequence
<220> FEATURE:
<223> OTHER INFORMATION: primer

<400> SEQUENCE: 64
cagcccaagg ctgcccctc ggtcactctg ttc                                 33

<210> SEQ ID NO 65
<211> LENGTH: 36
<212> TYPE: DNA
<213> ORGANISM: Artificial Sequence
<220> FEATURE:
<223> OTHER INFORMATION: primer

<400> SEQUENCE: 65
ctcgagtcac tatgaacatt ctgtaggggc cactgt                             36

<210> SEQ ID NO 66
<211> LENGTH: 2410
<212> TYPE: DNA
<213> ORGANISM: Homo sapiens

<400> SEQUENCE: 66
gaattcctgc aggtctatgg aacgataaat gcccatgaaa attctatttc aaggagacag    60
tcataatgaa atacctattg cctacggcag ccgctggatt gttattactc gctgcccaac   120
cagcgatggc ggaggtgcag ctggtggagt ctggggagg cgtggtccag cctgggaggt   180
ccctgagact ctcctgtgca gcctctggat tcaccttcag tagctatgct atgcactggg   240
tccgccaggc tccaggcaag gggctggagt gggtggcagt tatatcatat gatggaagta   300
ataaatacta cgcagactcc gtgaagggcc gattcaccat ctccagagac aattccaaga   360
acacgctgta tctgcaaatg aacagcctga gagctgagga cacggctgtg tattactgtg   420
cgagagcaca ttcccgctta ctatggttcg gggagttatt acccagcgct tttgactact   480
ggggccaggg aaccctggtc accgtctcct cagcttccac caagggccca tcggtcttcc   540
ccctggcacc ctcctccaag agcacctctg ggggcacagc ggccctgggc tgcctggtca   600
aggactactt ccccgaaccg gtgacggtgt cgtggaactc aggcgccctg accagcggcg   660
tgcacacctt cccggctgtc ctacagtcct caggactcta ctccctcagc agcgtggtga   720
ccgtgccctc cagcagcttg ggcacccaga cctacatctg caacgtgaat cacaagccca   780
gcaacaccaa ggtggacaag aaagttgagc ccaaatcttg taccaggcac aggcagccca   840
gaggctggga gcagctctac aacaccgtgt catttaacct tggagaagct tatgagtacc   900
ccacttttat acaagatttg cgcaatgaat tggctaaggg cacaccagta tgtcaacttc   960
cagtgacact acaaaccata gccgatgaca agcgatttgt tctagttgat atcactacga  1020
cctcgaagaa aacagttaag gttgctatag atgtgacaga tgtgtatgtt gtgggttatc  1080
aagacaaatg ggatgcaaa gatcgagctg ttttccttga caaggttcct actgttgcaa  1140
ctagtaaact tttcccaggg gtgactaatc gtgtaacgtt aacatttgat ggcagctatc  1200

```
agaaacttgt gaatgctgcc aaagctgata gaaaggctct cgaactgggg gttaacaaat   1260
tggaattttc cattgaagca atccatggta aaacgataaa tggtcaagag gcagccaagt   1320
tctttcttat tgtcatccaa atggtttcag aggcagctcg gttcaaatat attgagactg   1380
aggtggttga tagaggatta tatggatcat tcaaacctaa ttttaaagta ttgaacttgg   1440
agaacaattg gggcgacatc tctgatgcca ttcacaaatc atccccacaa tgtaccacta   1500
ttaatccggc acttcagttg ataagcccct caaatgaccc atgggttgta aataaagtga   1560
gtcaaattag tcccgatatg ggtatcctta agtttaaaag ctccaaatag tgactcgacc   1620
tgcaggtcta tggaacgata aatgcccatg aaaattctat ttcaaggaga cagtcataat   1680 gaaatacccta ttgcctacgg cagccgctgg attgttatta ctcgctgccc aaccagcgat   1740
ggcgcatcac catcaccatc actcctatga gctgactcag ccacccctcag tgtccgtgtc   1800 cccaggacag acagccagca tcacctgctc tggagataaa ttgggggata aatatgcttg   1860
ctggtatcag cagaagccag gccagtcccc tgtgctggtc atctatcaag atagcaagcg   1920
gccctcaggg atccctgagc gattctctgg ctccaactct gggaacacag ccactctgac   1980
catcagcggg acccaggcta tgatgaggc tgactattac tgtcaggcgt gggacagcag   2040
cactgtggta ttcggcggag ggaccaagct gaccgtccta ggtcagccca aggctgcccc   2100
ctcggtcact ctgttcccgc cctcctctga ggagctccaa gccaacaagg ccacactagt   2160
gtgtctgatc agtgacttct acccgggagc tgtgacagtg gcctggaagg cagatagcag   2220
ccccgtcaag gcgggagtgg agaccaccac accctccaaa cagagcaaca acaagtacgc   2280
ggccagcagc tacctgagcc tgacgcccga gcagtggaag tcccacagaa gctacagctg   2340
ccaggtcacg catgaaggga gcaccgtgga agacagtg ccccctacag aatgttcata   2400
gtgactcgag                                                          2410
```

<210> SEQ ID NO 67
<211> LENGTH: 754
<212> TYPE: PRT
<213> ORGANISM: Homo sapiens

<400> SEQUENCE: 67

```
Met Lys Tyr Leu Leu Pro Thr Ala Ala Ala Gly Leu Leu Leu Leu Ala
1               5                   10                  15

Ala Gln Pro Ala Met Ala Glu Val Gln Leu Val Glu Ser Gly Gly Gly
                20                  25                  30

Val Val Gln Pro Gly Arg Ser Leu Arg Leu Ser Cys Ala Ala Ser Gly
            35                  40                  45

Phe Thr Phe Ser Ser Tyr Ala Met His Trp Val Arg Gln Ala Pro Gly
        50                  55                  60

Lys Gly Leu Glu Trp Val Ala Val Ile Ser Tyr Asp Gly Ser Asn Lys
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Arg Ala His Ser Arg Leu Leu Trp Phe
        115                 120                 125

Gly Glu Leu Leu Pro Ser Ala Phe Asp Tyr Trp Gly Gln Gly Thr Leu
    130                 135                 140

Val Thr Val Ser Ser Ala Ser Thr Lys Gly Pro Ser Val Phe Pro Leu
```

-continued

```
            145                 150                 155                 160
        Ala Pro Ser Ser Lys Ser Thr Ser Gly Gly Thr Ala Ala Leu Gly Cys
                        165                 170                 175
        Leu Val Lys Asp Tyr Phe Pro Glu Pro Val Thr Val Ser Trp Asn Ser
                        180                 185                 190
        Gly Ala Leu Thr Ser Gly Val His Thr Phe Pro Ala Val Leu Gln Ser
                        195                 200                 205
        Ser Gly Leu Tyr Ser Leu Ser Ser Val Val Thr Val Pro Ser Ser Ser
                        210                 215                 220
        Leu Gly Thr Gln Thr Tyr Ile Cys Asn Val Asn His Lys Pro Ser Asn
        225                 230                 235                 240
        Thr Lys Val Asp Lys Lys Val Glu Pro Lys Ser Cys Thr Arg His Arg
                        245                 250                 255
        Gln Pro Arg Gly Trp Glu Gln Leu Tyr Asn Thr Val Ser Phe Asn Leu
                        260                 265                 270
        Gly Glu Ala Tyr Glu Tyr Pro Thr Phe Ile Gln Asp Leu Arg Asn Glu
                        275                 280                 285
        Leu Ala Lys Gly Thr Pro Val Cys Gln Leu Pro Val Thr Leu Gln Thr
        290                 295                 300
        Ile Ala Asp Asp Lys Arg Phe Val Leu Val Asp Ile Thr Thr Thr Ser
        305                 310                 315                 320
        Lys Lys Thr Val Lys Val Ala Ile Asp Val Thr Asp Val Tyr Val Val
                        325                 330                 335
        Gly Tyr Gln Asp Lys Trp Asp Gly Lys Asp Arg Ala Val Phe Leu Asp
                        340                 345                 350
        Lys Val Pro Thr Val Ala Thr Ser Lys Leu Phe Pro Gly Val Thr Asn
                        355                 360                 365
        Arg Val Thr Leu Thr Phe Asp Gly Ser Tyr Gln Lys Leu Val Asn Ala
                        370                 375                 380
        Ala Lys Ala Asp Arg Lys Ala Leu Glu Leu Gly Val Asn Lys Leu Glu
        385                 390                 395                 400
        Phe Ser Ile Glu Ala Ile His Gly Lys Thr Ile Asn Gly Gln Glu Ala
                        405                 410                 415
        Ala Lys Phe Phe Leu Ile Val Ile Gln Met Val Ser Glu Ala Ala Arg
                        420                 425                 430
        Phe Lys Tyr Ile Glu Thr Glu Val Val Asp Arg Gly Leu Tyr Gly Ser
                        435                 440                 445
        Phe Lys Pro Asn Phe Lys Val Leu Asn Leu Glu Asn Asn Trp Gly Asp
                        450                 455                 460
        Ile Ser Asp Ala Ile His Lys Ser Ser Pro Gln Cys Thr Thr Ile Asn
        465                 470                 475                 480
        Pro Ala Leu Gln Leu Ile Ser Pro Ser Asn Asp Pro Trp Val Val Asn
                        485                 490                 495
        Lys Val Ser Gln Ile Ser Pro Asp Met Gly Ile Leu Lys Phe Lys Ser
                        500                 505                 510
        Ser Lys Met Lys Tyr Leu Leu Pro Thr Ala Ala Gly Leu Leu Leu
                        515                 520                 525
        Leu Ala Ala Gln Pro Ala Met Ala His His His His His Ser Tyr
        530                 535                 540
        Glu Leu Thr Gln Pro Pro Ser Val Ser Val Ser Pro Gly Gln Thr Ala
        545                 550                 555                 560
        Ser Ile Thr Cys Ser Gly Asp Lys Leu Gly Asp Lys Tyr Ala Cys Trp
                        565                 570                 575
```

```
Tyr Gln Gln Lys Pro Gly Gln Ser Pro Val Leu Val Ile Tyr Gln Asp
                580                 585                 590

Ser Lys Arg Pro Ser Gly Ile Pro Glu Arg Phe Ser Gly Ser Asn Ser
            595                 600                 605

Gly Asn Thr Ala Thr Leu Thr Ile Ser Gly Thr Gln Ala Met Asp Glu
        610                 615                 620

Ala Asp Tyr Tyr Cys Gln Ala Trp Asp Ser Ser Thr Val Val Phe Gly
625                 630                 635                 640

Gly Gly Thr Lys Leu Thr Val Leu Gly Gln Pro Lys Ala Ala Pro Ser
                645                 650                 655

Val Thr Leu Phe Pro Pro Ser Ser Glu Glu Leu Gln Ala Asn Lys Ala
            660                 665                 670

Thr Leu Val Cys Leu Ile Ser Asp Phe Tyr Pro Gly Ala Val Thr Val
        675                 680                 685

Ala Trp Lys Ala Asp Ser Ser Pro Val Lys Ala Gly Val Glu Thr Thr
690                 695                 700

Thr Pro Ser Lys Gln Ser Asn Asn Lys Tyr Ala Ala Ser Ser Tyr Leu
            705                 710                 715                 720

Ser Leu Thr Pro Glu Gln Trp Lys Ser His Arg Ser Tyr Ser Cys Gln
            725                 730                 735

Val Thr His Glu Gly Ser Thr Val Glu Lys Thr Val Ala Pro Thr Glu
                740                 745                 750

Cys Ser

<210> SEQ ID NO 68
<211> LENGTH: 45
<212> TYPE: PRT
<213> ORGANISM: Homo sapiens

<400> SEQUENCE: 68

Gly Tyr Val Thr Glu Asp Gly Asp Thr Ala Leu His Leu Ala Val Ile
1               5                   10                  15

His Gln His Glu Pro Phe Leu Phe Leu Leu Gly Phe Ser Ala Gly Thr
                20                  25                  30

Glu Tyr Met Asp Leu Gln Asn Asp Leu Gly Gln Thr Ala
            35                  40                  45

<210> SEQ ID NO 69
<211> LENGTH: 60
<212> TYPE: PRT
<213> ORGANISM: Homo sapiens

<400> SEQUENCE: 69

Ala Glu Leu Gly Pro Gly Leu Ser Trp Ala Pro Leu Val Phe Gly Tyr
1               5                   10                  15

Val Thr Glu Asp Gly Asp Thr Ala Leu His Leu Ala Val Ile Gln His
                20                  25                  30

Glu Pro Phe Leu Asp Phe Leu Leu Gly Phe Ser Ala Gly Thr Glu Tyr
            35                  40                  45

Met Asp Leu Gln Asn Asp Leu Gly Gln Thr Ala Leu
        50                  55                  60

<210> SEQ ID NO 70
<211> LENGTH: 60
<212> TYPE: PRT
<213> ORGANISM: Homo sapiens
```

```
<400> SEQUENCE: 70

Ala Trp Leu Gly Pro Gly Leu Ser Trp Ala Pro Leu Val Phe Gly Tyr
1               5                   10                  15

Val Thr Glu Asp Gly Asp Thr Ala Leu His Leu Ala Val Ile Gln His
            20                  25                  30

Glu Pro Phe Leu Asp Phe Leu Leu Gly Phe Ser Ala Gly Thr Glu Tyr
            35                  40                  45

Met Asp Leu Gln Asn Asp Leu Gly Gln Thr Ala Leu
    50                  55                  60

<210> SEQ ID NO 71
<211> LENGTH: 64
<212> TYPE: PRT
<213> ORGANISM: Homo sapiens

<400> SEQUENCE: 71

Ala Glu Leu Gly Pro Gly Leu Ser Trp Ala Pro Leu Val Phe Gly Tyr
1               5                   10                  15

Val Thr Glu Asp Gly Asp Thr Ala Leu His Leu Ala Val Ile Gln His
            20                  25                  30

Glu Pro Phe Leu Asp Phe Leu Leu Gly Phe Ser Ala Gly Thr Glu Tyr
            35                  40                  45

Met Asp Leu Gln Asn Asp Leu Gly Gln Thr Ala Leu His Leu Ala Ala
    50                  55                  60

<210> SEQ ID NO 72
<211> LENGTH: 64
<212> TYPE: PRT
<213> ORGANISM: Homo sapiens

<400> SEQUENCE: 72

Ala Trp Leu Gly Pro Gly Leu Ser Trp Ala Pro Leu Val Phe Gly Tyr
1               5                   10                  15

Val Thr Glu Asp Gly Asp Thr Ala Leu His Leu Ala Val Ile Gln His
            20                  25                  30

Glu Pro Phe Leu Asp Phe Leu Leu Gly Phe Ser Ala Gly Thr Glu Tyr
            35                  40                  45

Met Asp Leu Gln Asn Asp Leu Gly Gln Thr Ala Leu His Leu Ala Ala
    50                  55                  60
```

ANTIBODY CONJUGATES AGAINST VARIANT NFKBIB AND USES THEREOF

CROSS-REFERENCE TO RELATED APPLICATIONS

This application is a divisional of U.S. patent application Ser. No. 12/744,523, filed Aug. 31, 2010, which is a U.S. national stage filing under 35 U.S.C. §371 of International Application No. PCT/CA2008/002076, filed on Nov. 27, 2008, which claims priority to U.S. Provisional Application No. 60/990,494, filed Nov. 27, 2007, which are incorporated herein by reference in their entirety.

GOVERNMENT INTERESTS

Not applicable

PARTIES TO A JOINT RESEARCH AGREEMENT

Not applicable

INCORPORATION BY REFERENCE OF MATERIAL SUBMITTED ON A COMPACT DISC

Not applicable

BACKGROUND

The present application relates to a novel antibody and antigen, and methods and compositions for treating and detecting cancer.

In the year 2000, an estimated 22 million people were suffering from cancer worldwide and 6.2 million deaths were attributed to this class of diseases. Every year, there are over 10 million new cases and this estimate is expected to grow by 50% over the next 15 years (WHO, World Cancer Report. Bernard W. Stewart and Paul Kleihues, eds. IARC Press, Lyon, 2003). Current cancer treatments are limited to invasive surgery, radiation therapy and chemotherapy, all of which cause either potentially severe side-effects, non-specific toxicity and/or traumatizing changes to ones body image and/or quality of life. Cancer can become refractory to chemotherapy reducing further treatment options and likelihood of success. The prognosis for some cancer is worse than for others and some are almost always fatal. In addition, some cancers with a relatively high treatment success rate remain major killers due to their high incidence rates.

One of the causes for the inadequacy of current cancer treatments is their lack of selectivity for affected tissues and cells. Surgical resection always involves the removal of apparently normal tissue as a "safety margin" which can increase morbidity and risk of complications. It also always removes some of the healthy tissue that may be interspersed with tumor cells and that could potentially maintain or restore the function of the affected organ or tissue. Radiation and chemotherapy will kill or damage many normal cells due to their non-specific mode of action. This can result in serious side-effects such as severe nausea, weight loss and reduced stamina, loss of hair etc., as well as increasing the risk of developing secondary cancer later in life. Treatment with greater selectivity for cancer cells would leave normal cells unharmed thus improving outcome, side-effect profile and quality of life.

The selectivity of cancer treatment can be improved by targeting molecules that are specific to cancer cells and not found on normal cells. These molecules can then be used as a target to antibody-based diagnostic or therapeutics or for drugs capable of altering their function.

The IkB proteins are a family of structurally related, intracellular proteins that bind to NF-kB and regulate its activity through a complex system of site-, and enzyme-specific phosphorylation, feedback gene regulation and trans-location between the cytoplasmic and nuclear compartments. Several members of this family have been identified and include IkBα, β, ε, γ and BCL-3 (see Hayden & Ghosh, Genes Dev 18:2195-2224, 2004 for review of the NF-kB pathway). The sequence variability between the IkB proteins results in important differences in functionality.

IkBβ was initially identified as TRIP-9 and is also named NF-kappa-B inhibitor beta, NF-kappa-BIB, I-kappa-B-beta, IkappaBbeta, IkB-beta, IkB-B, thyroid receptor interacting protein 9 and TR-interacting protein 9. Two major splice variants, namely IkBβ1 and IkBβ2, have been reported. These isoforms differ in their C-terminal sequences with significant consequence on their degradation and effect on NF-kB. As a result, the β2 isoform appears more restricted to the cytoplasm and more slowly degraded than the β1 isoform (Hirano et al., Mol Cell Biol 18(5):2596-2607, 1998). The β2 isoforms was reported as the dominant form of IkBβ in cytoplasmic extract from the HT-29 human colon cancer cell line (km et al., Mol Carcinogenesis 29:25-36, 2000). Human IkBβ1 proteins have been proposed for the treatment of inflammatory and autoimmune diseases (U.S. Pat. No. 5,952,483) and a rabbit IkBβ protein analogous to human IkBβ1, for the treatment of disorders associated with NF-kB-induced gene activation (U.S. Pat. No. 5,597,898).

The NF-kB-IkBβ complex is generally retained in the cytoplasm of quiescent cells thus blocking the transcriptional activity of NF-kB. Upon site-specific and signal-induced phosphorylation of IkBβ, the complex dissociates and IkBβ is tagged for degradation through the ubiquitin-proteasome pathway. Free NF-kB translocate to the nucleus where it binds to DNA and regulate the expression of various genes (Malek et al, JBC 276(48):45225-235, 2001). The ability of IkBβ to retain NF-kB in the cytoplasm appears linked in part to the phosphorylation of the C-terminal PEST domain and the association of a further molecule with the complex (Chen, Wu and Ghosh, JBC 278(25):23101-106, 2003; Chu et al., Mol Cell Biol 16(11):5974-84, 1996) and thus varies between β1 and β2 isoforms. Newly synthesized or under-phosphorylated IkBβ may be able to translocate to the nucleus and retains the ability to bind NF-kB but without preventing or interrupting its gene transcriptional activity (Tran et al, Mol Cell Biol 17(9): 5386-99, 1998). In contrast, NF-kB is not strictly retained in the cytoplasm when bound to IkBα but moves back and forth between the nucleus and the cytoplasm through a complex import-export mechanism with an equilibrium that favors its localization in the cytoplasm of quiescent cells. The difference in the ability of IkBα and IkBβ to control the localization and activity of NF-kB is thought to be due in part to a protein insert found the IkBβ molecules but not the α form (Chen, Wu and Ghosh, JBC 278(25):23101-106, 2003). The role and specific regulation of the IkB proteins are far from being fully understood but it is generally accepted that these proteins are cytoplasmic, that some are able to translocate between the nucleus and the cytoplasm and that all are likely to have a significant role in the regulation of cell growth, apoptosis, response to inflammation and probably cancer.

Mutations of the IkBα gene in cancer cells have been reported (Cabannes et al., Oncogene 18:3063-70, 1999) but to date, not for the Ikβ isoforms. Under- and over-expression of IkBα and IkBβ have also been implicated in disregulation of the NF-kB pathway in cancer cells (JBC 274(26): 18827-835, 1999).

SUMMARY OF THE INVENTION

The present inventors have identified a novel antibody and antigen. Specifically, the inventors have identified a novel cancer-specific antibody, which binds to several types of cancer cells including, colon cancer, pancreatic cancer, kidney cancer, liver cancer, breast cancer, skin cancer, ovarian cancer, head and neck cancer, prostate cancer and lung cancer. Importantly, the antibody does not significantly bind to normal tissue making it a suitable candidate for cancer therapy and diagnosis. The inventors have also identified the antigen to which the novel antibody specifically binds.

In addition, the inventors identified a novel cancer-associated antigen. Specifically, the inventors have identified a variant of IkBβ which is expressed on the surface of cancer cells. In a specific embodiment, the novel cancer-associated antigen is a variant of IkBβ isoform 2 (IkBβ2) which is expressed on the surface of cancer cells.

The inventors have cloned and sequenced the antibody and determined the sequence of the antibody light and heavy chain variable regions and complementarity determining regions 1, 2 and 3.

Accordingly, the present application discloses isolated light chain complementarity determining region 1 (CDR1) comprising the amino acid sequence SGDKLGDKYAC (SEQ ID NO:8); isolated light chain complementarity determining region 2 (CDR2) comprising the amino acid sequence QDSKRPS (SEQ ID NO: 9); and isolated light chain complementarity determining region 3 (CDR3) comprising the amino acid sequence QAWDSSTVV (SEQ ID NO: 10); and isolated heavy chain CDR1 comprising the amino acid sequence SYAMH (SEQ ID NO: 5); isolated heavy chain CDR2 comprising the amino acid sequence VISYDGSNKYYADSVKG (SEQ ID NO: 6); and isolated heavy chain CDR3 comprising the amino acid sequence AHSRLLWFGELLPSAFDY (SEQ ID NO: 7).

The present application also provides isolated nucleic acid sequences encoding the light chain CDR1 comprising the amino acid sequence SGDKLGDKYAC (SEQ ID NO: 8); the light chain CDR2 comprising the amino acid sequence QDSKRPS (SEQ ID NO: 9); the light chain CDR3 comprising the amino acid sequence QAWDSSVV (SEQ ID NO: 10); the heavy chain CDR1 comprising the amino acid sequence SYAMH (SEQ ID NO: 5); the heavy chain CDR2 comprising the amino acid sequence VISYDGSNKYYADSVKG (SEQ ID NO: 6); and the heavy chain CDR3 comprising the amino acid sequence AHSRLLWFGELL PSAFDY (SEQ ID NO: 7).

Additional aspects disclosed in the present application are isolated light chain variable regions comprising light chain CDR1, CDR2 and/or CDR3 of the present application (SEQ ID NOS: 8-10), and isolated heavy chain variable regions comprising heavy chain CDR1, CDR2 and/or CDR3 of the present application (SEQ ID NOS: 5-7). In one embodiment, the light chain variable region comprises the amino acid sequence shown in FIG. 1B (SEQ ID NO: 4). In another embodiment, the heavy chain variable region comprises the amino acid sequence shown in FIG. 1A (SEQ ID NO: 2).

The present application also includes the isolated nucleic acid sequence encoding the light chain variable region disclosed herein and the isolated nucleic acid sequence encoding the heavy chain variable region disclosed herein. In one embodiment, the nucleic acid sequence encoding the light chain variable region comprises the nucleic acid sequence shown in FIG. 1B (SEQ ID NO: 3). In another embodiment, the nucleic acid sequence encoding the heavy chain variable region comprises the nucleic acid sequence shown in FIG. 1A (SEQ ID NO: 1).

Another aspect of the present application is a binding protein, preferably an antibody or antibody fragment, that comprises at least one light chain complementarity determining region disclosed in the present application (i.e. one or more of SEQ ID NOS: 8-10) and/or at least one heavy chain complementarity determining region of the present application (i.e. one or more of SEQ ID NOS: 5-7). The present application also provides a binding protein, preferably an antibody or antibody fragment, that comprises the light chain variable regions disclosed herein and/or the heavy chain variable regions disclosed herein.

As mentioned above, the inventors have also identified the antigen to which the binding protein of the present application bind. Accordingly, the present application provides binding proteins that bind to IkBβ proteins, including IkBβ isoform 1 (IkBβ1), IkBβ isoform 2 (IkBβ2) and a cancer-associated variant of IkBβ. In one embodiment, the cancer-associated variant is a variant of IkBβ2.

In addition, the present application provides compositions comprising the binding proteins of the present application, such as antibodies and antibody fragments, and a pharmaceutically acceptable excipient, carrier, buffer or stabilizer.

Further, the present application provides for isolated nucleic acid sequences that encode the binding proteins of the present application.

Another aspect of the present application is an immunoconjugate comprising (1) binding protein of the present application, preferably an antibody or antibody fragment that binds to an antigen or molecule on a cancer cell, attached to (2) an effector molecule. A further aspect of the present application is an immunoconjugate comprising (1) binding protein of the present application, preferably an antibody or antibody fragment that binds to an antigen or molecule that is internalized by a cancer cell, attached to (2) an effector molecule. In a preferred embodiment, the effector molecule is (i) a label, which can generate a detectable signal, directly or indirectly, or (ii) a cancer therapeutic agent, which is either cytotoxic, cytostatic or otherwise prevents or reduces the ability of the cancer cells to divide and/or metastasize. Preferably, the cancer therapeutic agent is a toxin or cytotoxin. In one embodiment, the immunoconjugate comprises the amino acid sequence defined by SEQ ID NO: 67.

The present application also provides isolated nucleic acid sequences that encode the immunoconjugates of the present application. In one embodiment, the isolated nucleic acid sequence encodes a protein comprising the amino acid sequence defined by SEQ ID NO: 67. In another embodiment, the isolated nucleic acid sequence comprises SEQ ID NO: 66.

The present application also provides compositions comprising the immunoconjugates disclosed herein and uses of the immunoconjugate for the manufacture of a medicament for treating or preventing cancer, and diagnostic purposes. In addition, the present application provides methods of treating or preventing cancer by administering the immunoconjugates disclosed herein and related kits.

A further aspect of the present application is a method of detecting or monitoring cancer in a subject comprising the steps of:

(1) contacting a test sample taken from said subject with a binding protein or immunoconjugate of the present application and that binds specifically to an antigen on the cancer cell to produce a binding protein-antigen complex;

(2) measuring the amount of binding protein-antigen complex in the test sample; and (3) comparing the amount of binding protein-antigen complex in the test sample to a control.

Another aspect is a diagnostic agent comprising the immunoconjugate of the present application, wherein the effector molecule is a label, which can generate a detectable signal, directly or indirectly.

The present application also includes an isolated protein that can specifically bind with one of the binding proteins of the present application, nucleic acid sequences and uses thereof.

As mentioned above, the inventors have identified the antigen to which the binding protein of the present application binds. Thus, the present application includes an isolated protein comprising a cancer-associated variant of IkBβ. The present application also includes isolated nucleic acid sequences encoding the cancer-associated variant of IkBβ.

The present application also includes binding proteins that bind to the cancer-associated variant of IkBβ.

The present application includes the use of the antigen of the present application in the treatment and diagnosis of cancer.

Accordingly, the present application includes a method of detecting or monitoring cancer in a subject, comprising detecting the antigen of the present application on a cell in the sample, wherein cancer is indicated, if the antigen is detected on the cell. The application also includes a method of detecting or monitoring cancer in a subject, comprising detecting RNA expression of the cancer-associated variant of IkBβ of the present application by a cell in the sample, wherein cancer is indicated, if RNA expression of the cancer-associated variant of IkBβ is detected.

The present application also includes pharmaceutical compositions comprising an effective amount of the antigen of the present application, the isolated nucleic acid sequences encoding the antigen of the present application or the recombinant expression vectors comprising nucleic acid sequences that encode the antigen of the present application, with a pharmaceutically acceptable excipient, carrier, buffer or stabilizer.

A further aspect of the present application is the use of the antigen of the present application, the isolated nucleic acid sequences encoding the antigen of the present application or the recombinant expression vectors comprising nucleic acid sequences that encode the antigen of the present application to elicit an immune response in a subject.

A further aspect of the present application is the use of the antigen of the present application, the isolated nucleic acid sequences encoding the antigen of the present application or the recombinant expression vectors comprising nucleic acid sequences that encode the antigen of the present application to treat or prevent cancer.

In addition, the present application includes methods for treating or preventing cancer in a subject comprising administering to the subject or a cell from the subject an effective amount of the antigen of the present application, the isolated nucleic acid sequences encoding the antigen of the present application or the recombinant expression vectors comprising nucleic acid sequences that encode the antigen of the present application.

The present application also includes methods for inducing an immune response in a subject against the antigen of the present application comprising administering to the subject or a cell from the subject an effective amount of the antigen of the present application, the isolated nucleic acid sequences encoding the antigen of the present application or the recombinant expression vectors comprising nucleic acid sequences that encode the antigen of the present application.

Other features and advantages of the present application will become apparent from the following detailed description. It should be understood, however, that the detailed description and the specific examples while indicating preferred embodiments of the present application are given by way of illustration only, since various changes and modifications within the spirit and scope of the present application will become apparent to those skilled in the art from this detailed description.

DESCRIPTION OF DRAWINGS

The present application will now be described in relation to the drawings in which:

FIG. 1 shows the nucleotide and amino acid sequences of (A) the mu, VH3 (SEQ ID NOS: 1 and 2, respectively) and (B) the lambda, VL3 (SEQ ID NOS: 3 and 4, respectively) chains of VB1-204.

FIG. 4A shows a saturation curve of VB1-204, which was determined by measuring the reactivity of increased concentrations of VB1-204 to the A-375 carcinoma cells by flow cytometry. FIG. 4B: Lineweaver-Burk Method, the binding constant was determined by Lineweaver-Burk method.

FIG. 5 shows Western blots of proteins from purified membrane fraction immunoprecipitated and probed with VB1-204.

FIG. 7A-C shows the identification of peptides from MS Analysis of tumor cell lines A: CFPAC-1, B: A-375 and C: MB-231. Peptides recovered from each cell type mapping to IkBβ2 are underlined and bolded.

FIG. 8 shows peptides recovered by de-novo sequencing and their mapped positions corresponding to IkBβ2. Recovered sequences are bolded. Variant amino acids from the recovered peptides are underlined.

FIG. 9A shows the monoisotopic mass of neutral peptide Mr(calc): 1986.9720, Fixed modifications: Carbamidomethyl (C) ions Score: 47 Expect: 1e+002 Matches (Bold Red): 3/176 fragment ions using 8 most intense peak. FIG. 9B shows the monoisotopic mass of neutral peptide Mr(calc): 1070.5542 Fixed modifications: Carbamidomethyl (C) Variable modifications: M1: Oxidation (M) Ions Score: 52

Expect: 7.7e+002 Matches (Bold Red): 10/80 fragment ions using 25 most intense peaks. FIG. 9C shows the monoisotopic mass of neutral peptide Mr(calc): 1203.5811 Ions Score: 98 Expect: 7.2e-06 Matches (Bold Red): 4/68 fragment ions using 6 most intense peaks.

FIG. 11 shows the VB1-204 nucleotide sequences (SEQ ID NO:66) and amino acid (SEQ ID NO:67).

DETAILED DESCRIPTION (A) Definitions

Figure 2:
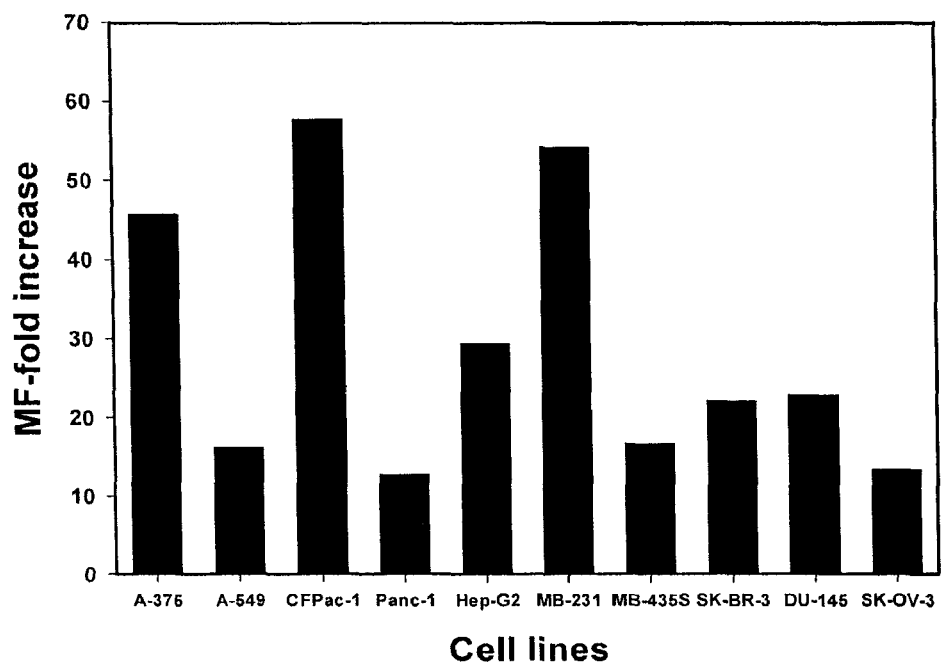
FIG. 2 shows the tumor profiling of VB1-204. Melanoma (A-375), lung (A-549), pancreas (CFPac-1 and Panc-1), liver (Hep-G2), breast (MB-231, MB-435S and SK-BR-3), prostate. (DU-145) and ovary (SK-OV-3) tumor cell lines were incubated with VB 1-204 at 100 (µg/mL and bound material was detected with a goat anti-human H&L antibody coupled to FITC by flow cytometry. The mean of the median fluorescence (MF) over the control antibody from two independent experiments is represented.

The term "a cell" includes a single cell as well as a plurality or population of cells. Administering an agent to a cell includes both in vitro and in vivo administrations.

The term "administered systemically" as used herein means that the immunoconjugate and/or other cancer therapeutic may be administered systemically in a convenient manner such as by injection (subcutaneous, intravenous, intramuscular, etc.), oral administration, inhalation, transdermal administration or topical application (such as topical cream or ointment, etc.), suppository applications, or means of an implant. An implant can be of a porous, non-porous, or gelatinous material, including membranes, such as sialastic membranes, or fibers. Suppositories generally contain active ingredients in the range of 0.5% to 10% by weight.

The term "amino acid" includes all of the naturally occurring amino acids as well as modified amino acids.

The term "antibody" as used herein is intended to include monoclonal antibodies, polyclonal antibodies, and chimeric antibodies. The antibody may be from recombinant sources and/or produced in transgenic animals. The term "antibody fragment" as used herein is intended to include without limitations Fab, Fab', F(ab')$_2$, scFv, dsFv, ds-scFv, dimers, minibodies, diabodies, and multimers thereof, multi-specific antibody fragments and Domain Antibodies. Antibodies can be fragmented using conventional techniques. For example, F(ab')$_2$ fragments can be generated by treating the antibody with pepsin. The resulting F(ab')$_2$ fragment can be treated to reduce disulfide bridges to produce Fab' fragments. Papain digestion can lead to the formation of Fab fragments. Fab, Fab' and F(ab')$_2$, scFv, dsFv, ds-scFv, dimers, minibodies, diabodies, bispecific antibody fragments and other fragments can also be synthesized by recombinant techniques.

The term "antibody or antibody fragment of the present application" as used herein comprises at least one light chain complementarity determining region of the present application (i.e. one or more of SEQ ID NOS: 8-10) and/or at least one heavy chain complementarity determining region of the present application (i.e. one or more of SEQ ID NOS: 5-7). In one embodiment, the antibody or antibody fragment comprises the light chain CDR sequences (i.e. all of SEQ ID NOS: 8-10) and/or the heavy chain CDR sequences (i.e. all of SEQ ID NOS: 5-7). In another embodiment, the antibody or antibody fragment comprises the amino acid sequence of SEQ ID NO: 4 (light chain variable region) and/or the amino acid sequence of SEQ ID NO: 2 (heavy chain variable region). Antibodies or antibody fragments of the present application also include antibodies or antibody fragments that bind to the antigen of the present application. The antibody or antibody fragments of the present application also include functional variants of the sequences so that the antibody or antibody fragment can bind to the cancer cell without substantially binding to normal cells.

The term "antigen of the present application" as used herein refers to antigens that the binding proteins of the application are able to bind, and include IkBβ proteins, including IkBβ isoform 1 (IkBβ1), IkBβ isoform 2 (IkBβ2) and/or cancer-associated variant of IKBβ, and fragments or parts thereof (e.g. the extracellular domain of the cancer associated variant of IkBβ). The term "IkBβ isoform 1 or IkBβ1" as used herein refers to a protein defined by SEQ ID NO:28. The term "IkBβ isoform 2 or IkBβ2" as used herein refers to a protein defined by SEQ ID NO: 27. The term "cancer-associated variant of IkBβ" or "variant IkBβ" as used herein refers to a novel variant of IkBβ that is expressed on the surface of cancer cells and not significantly on non-cancerous cells. In one embodiment of the present application, the cancer-associated variant of IkBβ has the same function as IkBβ, as an inhibitory regulator of NFk-B, but a different localization in the cell (i.e. on the cell membrane). In another embodiment, the cancer-associated variant of IkBβ comprises the amino acid sequence defined by SEQ ID NO: 32 and/or 36. In a further embodiment, the cancer-associated variant of IkBβ comprises the amino acid sequence defined by SEQ ID NO: 30. In an additional embodiment, cancer-associated variant of IkBβ consists of the amino acid sequence defined by SEQ ID NO: 30. In a further embodiment, the cancer-associated variant of IkBβ comprises the sequence of SEQ ID NO: 27 in which one or more amino acids selected from positions 26, 27, 31, 34, 39, 106, 111, and 112 is substituted with another amino acid or is chemically modified. In a further embodiment, the substitution or chemical modification results in an increase in the hydrophobicity of the region where the change was made relative to the non-modified protein (i.e. SEQ ID NO: 27). In an additional embodiment, the substitution is one or more of the following: P026V, D027L, P031V, P034V, E039W, E106V, E111V and/or K112A. In another embodiment of the present application, the cancer-associated variant of IkBβ, comprises IkBβ with one or more transmembrane domains not normally present in IkBβ. In one embodiment, the transmembrane domain comprises the amino acid sequence of SEQ ID NO: 53 or 54. In one embodiment, the cancer-associated variant of IkBβ is a variant of IkBβ2.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6(Log 10[Na+)+0.41(% (G+C)-600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm−5° C. based on the above equation, followed by a wash of 0.2×SSC/0.1% SDS at 60° C. Moderately stringent hybridization conditions include a washing step in 3×SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 2002, and in: Sambrook et al., Molecular Cloning: a Laboratory Manual, Cold Spring Harbor Laboratory Press, 2001.

The term "binding protein" as used herein refers to proteins that specifically bind to another substance such as a cancer-associated antigen of the present application. In an embodiment, binding proteins are antibodies or antibody fragments.

By "biologically compatible form suitable for administration in vivo" is meant a form of the substance to be administered in which any toxic effects are outweighed by the therapeutic effects.

The term "cancer" as used herein includes any cancer that can be bound by a binding protein of the present application, preferably an antibody or antibody fragment of the present application.

The term "cancer cell" includes cancer or tumor-forming cells, transformed cells or a cell that is susceptible to becoming a cancer or tumor-forming cell.

The term "complementary" refers to nucleic acid sequences capable of base-pairing according to the standard Watson-Crick complementary rules, or being capable of hybridizing to a particular nucleic acid segment under stringent conditions.

A "conservative amino acid substitution", as used herein, is one in which one amino acid residue is replaced with another amino acid residue without abolishing the protein's desired properties.

The term "control" as used herein refers to a sample from a subject or a group of subjects who are either known as having cancer or not having cancer.

The term "controlled release system" as used means the immunoconjugate and/or other cancer therapeutic of the present application can be administered in a controlled fashion. For example, a micropump may deliver controlled doses directly into the area of the tumor, thereby finely regulating the timing and concentration of the pharmaceutical composition (see, e.g., Goodson, 1984, in Medical Applications of Controlled Release, vol. 2, pp. 115-138).

The term "derivative of a peptide" refers to a peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine.

The phrase "detecting or monitoring cancer" refers to a method or process of determining if a subject has or does not have cancer, the extent of cancer, the severity of cancer and/or grade of cancer.

The term "direct administration" as used herein means the cancer therapeutic may be administered, without limitation, intratumorally, intravascularly, and peritumorally. For example, the cancer therapeutic may be administered by one or more direct injections into the tumor, by continuous or discontinuous perfusion into the tumor, by introduction of a reservoir of the cancer therapeutic, by introduction of a slow-release apparatus into the tumor, by introduction of a slow-release formulation into the tumor, and/or by direct application onto the tumor. By the mode of administration "into the tumor," introduction of the cancer therapeutic to the area of the tumor, or into a blood vessel or lymphatic vessel that substantially directly flows into the area of the tumor, is included.

As used herein, the phrase "effective amount" means an amount effective, at dosages and for periods of time necessary to achieve the desired result. Effective amounts of therapeutic may vary according to factors such as the disease state, age, sex, weight of the animal. Dosage regime may be adjusted to provide the optimum therapeutic response. For example, several divided doses may be administered daily or the dose may be proportionally reduced as indicated by the exigencies of the therapeutic situation.

The term "eliciting an immune response" or "inducing an immune response" as used herein means initiating, triggering, causing, enhancing, improving or augmenting any response of the immune system, for example, of either a humoral or cell-mediate nature. The initiation or enhancement of an immune response can be assessed using assays known to those skilled in the art including, but not limited to, antibody assays (for example ELISA assays), antigen specific cytotoxicity assays and the production of cytokines (for example ELISPOT assays). Preferably, the isolated proteins, nucleic acid sequences or recombinant expression vectors of the present application, and the method of the present application, trigger or enhance a cellular immune response, more preferably a T cell response.

The term "heavy chain complementarity determining region" as used herein refers to regions of hypervariability within the heavy chain variable region of an antibody molecule. The heavy chain variable region has three complementarity determining regions termed heavy chain complementarity determining region 1, heavy chain complementarity determining region 2 and heavy chain complementarity determining region 3 from the amino terminus to carboxy terminus.

The term "heavy chain variable region" as used herein refers to the variable region of a heavy chain.

The term "immunoconjugate of the present application" is used herein comprises (1) a binding protein, preferably an antibody or antibody fragment, of the present application attached to (2) an effector molecule. The effector molecule can be any molecule that one wishes to deliver to the cancer cell, including, but not limited to (i) a label, which can generate a detectable signal, directly or indirectly, or (ii) a cancer therapeutic agent, such as a toxin that is either cytotoxic, cytostatic or otherwise prevents or reduces the ability of the cancer cells to divide and/or metastasize. The term "immunotoxin of the present application" refers to an immunoconjugate, wherein the effector molecule is a cancer therapeutic agent, such as a toxin that is either cytotoxic, cytostatic or otherwise prevents or reduces the ability of the cancer cells to divide and/or metastasize.

The term "isolated nucleic acid sequences" as used herein refers to a nucleic acid substantially free of cellular material or culture medium when produced by recombinant DNA techniques, or chemical precursors, or other chemicals when chemically synthesized. An isolated nucleic acid is also substantially free of sequences which naturally flank the nucleic acid (i.e. sequences located at the 5' and 3' ends of the nucleic acid) from which the nucleic acid is derived. The term "nucleic acid" is intended to include DNA and RNA and can be either double stranded or single stranded, and represents the sense or antisense strand. Further, the term "nucleic acid" includes the complementary nucleic acid sequences.

The term "isolated proteins" refers to a protein substantially free of cellular material and/or culture medium when produced by recombinant DNA techniques, or obtained from cultured cells or tissue samples, or of chemical precursors or other chemicals when chemically synthesized.

The term "light chain complementarity determining region" as used herein refers to regions of hypervariability within the light chain variable region of an antibody molecule. Light chain variable regions have three complementarity determining regions termed light chain complementarity determining region 1, light chain complementarity determining region 2 and light chain complementarity determining region 3 from the amino terminus to the carboxy terminus.

The term "light chain variable region" as used herein refers to the variable region of a light chain.

The term "modified bouganin" as used here means a modified bouganin that has a reduced propensity to activate an immune response as described in PCT/CA2005/000410 and U.S. patent application Ser. No. 11/084,080, which published as US2005-0238642 A1. In one example, the modified bouganin has the amino acid sequence (SEQ ID NO: 11):

YNTVSFNLGEAYEYPTFIQDLRNELAKGTPVCQLPVTLQTIADDKRFVLV

DITTTSKKTVKVAIDVTDVYVVGYQDKWDGKDRAVFLDKVPTVATSKLFP

GVTNRVTLTFDGSYQKLVNAAKADRKALELGVNKLEFSIEAIHGKTINGQ

EAAKFFLIVIQMVSEAARFKYIETEWDRGLYGSFKPNFKVLNLENNWGDI

SDAIHKSSPQCTTINPALQLISPSNDPWVVNKVSQISPDMGILKFKSSK.

The term "nucleic acid sequence" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present application may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine.

The term "sample" as used herein refers to any fluid, cell or tissue sample from a subject which can be assayed for cancer.

The term "sequence identity" as used herein refers to the percentage of sequence identity between two polypeptide sequences. In order to determine the percentage of identity between two polypeptide sequences, the amino acid sequences of such two sequences are aligned, preferably using the Clustal W algorithm (Thompson, J D, Higgins D G, Gibson T J, 1994, Nucleic Acids Res. 22 (22): 4673-4680), together with BLOSUM 62 scoring matrix (Henikoff S, and Henikoff J. G., 1992, Proc. Natl. Acad. Sci. USA 89: 10915-10919) and a gap opening penalty of 10 and gap extension penalty of 0.1, so that the highest order match is obtained between two sequences wherein at least 50% of the total length of one of the sequences is involved in the alignment. Other methods that may be used to align sequences are the alignment method of Needleman and Wunsch (J. Mol. Biol., 1970, 48: 443), as revised by Smith and Waterman (Adv. Appl. Math., 1981, 2: 482) so that the highest order match is obtained between the two sequences and the number of identical amino acids is determined between the two sequences. Other methods to calculate the percentage identity between two amino acid sequences are generally art recognized and include, for example, those described by Carillo and Lipton (SIAM J. Applied Math., 1988, 48:1073) and those described in Computational Molecular Biology, Lesk, e.d. Oxford University Press, New York, 1988, Biocomputing: Informatics and Genomics Projects. Generally, computer programs will be employed for such calculations. Computer programs that may be used in this regard include, but are not limited to, GCG (Devereux et al., Nucleic Acids Res., 1984, 12: 387) BLASTP, BLASTN and FASTA (Altschul et al., J. Molec. Biol., 1990:215:403).

The term "subject" as used herein refers to any member of the animal kingdom, preferably a mammal, more preferably a human being. In a preferred embodiment, the subject is suspected of having or has cancer.

As used herein, the phrase "treating or preventing cancer" refers to inhibiting of cancer cell replication, preventing transformation of a cell to a cancer-forming cell, inhibiting of cancer spread (metastasis), inhibiting of tumor growth, reducing cancer cell number or tumor growth, decreasing in the malignant grade of a cancer (e.g., increased differentiation), or improving cancer-related symptoms.

The term "variant" as used herein includes modifications or chemical equivalents of the amino acid and nucleotide sequences of the present application that perform substantially the same function as the proteins or nucleic acid molecules of the present application in substantially the same way. For example, variants of proteins of the present application include, without limitation, conservative amino acid substitutions. Variants of proteins of the present application also include additions and deletions to the proteins of the present application. In addition, variant peptides and variant nucleotide sequences include analogs and derivatives thereof. A variant of the cancer-associated antigen of the present application means a protein sequence that is expressed on cancer cells but not normal cells. include additions and deletions to the proteins of the present application. In addition, variant peptides and variant nucleotide sequences include analogs and derivatives thereof. A variant of the cancer-associated antigen of the present application means a protein sequence that is expressed on cancer cells but not normal cells.

(B) Complementarity Determining Regions and Binding Proteins (i) Light and Heavy Chain Complementarity Determining Regions and Light and Heavy Chain Variable Regions The present application provides isolated light chain complementarity determining region 1 (CDR1) comprising the amino acid sequence SGDKLGDKYAC (SEQ ID NO: 8); isolated light chain complementarity determining region 2 (CDR2) comprising the amino acid sequence QDSKRPS (SEQ ID NO: 9); and isolated light chain complementarity determining region 3 (CDR3) comprising the amino acid sequence QAWDSSTW (SEQ ID NO: 10); and isolated heavy chain CDR1 comprising the amino acid sequence SYAMH (SEQ ID NO: 5); isolated heavy chain CDR2 comprising the amino acid sequence VISYDGSNKYYADSVKG (SEQ ID NO: 6); and isolated heavy chain CDR3 comprising the amino acid sequence AHSRLLWFGELLPSAFDY (SEQ ID NO: 7).

The present application also includes variants of the CDR sequences that can bind to the same antigen recognized by the CDR sequences disclosed above.

Additional aspects of the present application are isolated light chain variable regions comprising light chain CDR1, CDR2 and/or CDR3 of the present application (SEQ ID NOS: 8-10), and isolated heavy chain variable regions comprising heavy chain CDR1, CDR2 and/or CDR3 of the present application (SEQ ID NOS: 5-7). In one embodiment, the light chain variable region comprises the amino acid sequence shown in FIG. 1B (SEQ ID NO: 4). In another embodiment, the heavy chain variable region comprises the amino acid sequence shown in FIG. 1A (SEQ ID NO: 2).

The present application also includes variants of the isolated light chain variable regions and heavy chain variable regions that can bind to the same antigen recognized by the isolated light chain variable regions and isolated heavy chain variable regions disclosed above.

A person skilled in the art will appreciate that the present application includes variants to the amino acid sequences of SEQ ID NOS: 5-10, 2 and 4, including chemical equivalents to the sequences disclosed by the present application. Such equivalents include proteins that perform substantially the same function as the specific proteins disclosed herein in substantially the same way. For example, a functional variant of a CDR sequence will be able to bind to the antigen recognized by the native CDR sequence. For example, equivalents include, without limitation, conservative amino acid substitutions.

In one embodiment, the variant amino acid sequences of the light chain CDR1, CDR2 and CDR3, and the heavy chain CDR1, CDR2 and CDR3 have at least 50%, preferably at least 60%, more preferably at least 70%, most preferably at least 80%, even more preferably at least 90%, and even most preferably 95% sequence identity to SEQ ID NOS: 5-10, respectively.

In another embodiment, the variant amino acid sequences of the light chain variable region and the heavy chain variable region have at least 50%, preferably at least 60%, more preferably at least 70%, most preferably at least 80%, even more preferably at least 90% and even most preferably 95% sequence identity to SEQ ID NOS: 2 and 4, respectively.

The present application also provides an isolated nucleic acid sequence encoding the light chain variable region of the present application and an isolated nucleic acid sequence encoding the heavy chain variable region of the present application. In one embodiment, the isolated nucleic acid sequence encodes the light chain variable region comprising the amino acid sequence shown in FIG. 1B (SEQ ID NO: 4). In another embodiment, isolated nucleic acid sequence encodes the heavy chain variable region comprising the amino acid sequence shown in FIG. 1A (SEQ ID NO: 2). In a further embodiment, the nucleic acid sequence encoding the light chain variable region comprises the nucleic acid sequence shown in FIG. 1B (SEQ ID NO: 3). In an additional embodiment, the nucleic acid sequence encoding the heavy chain variable region comprises the nucleic acid sequence shown in FIG. 1A (SEQ ID NO: 1). The present application also includes variants to the nucleic acid sequences that encode for the light chain variable region and heavy chain variable region of the present application. For example, the variants include nucleotide sequences that hybridize to the nucleic acid sequences encoding the light chain variable region and heavy chain variable region of the present application under at least moderately stringent hybridization conditions.

The present application also provides isolated nucleic acid sequences encoding the light chain CDR1 comprising the amino acid sequence SGDKLGDKYAC (SEQ ID NO: 8); the light chain CDR2 comprising the amino acid sequence QDSKRPS (SEQ ID NO: 9); the light chain CDR3 comprising the amino acid sequence QAWDSSTW (SEQ ID NO: 10); the heavy chain CDR1 comprising the amino acid sequence SYAMH (SEQ ID NO: 5); the heavy chain CDR2 comprising the amino acid sequence VISYDGSNKYYADSVKG (SEQ ID NO: 6); and the heavy chain CDR3 comprising the amino acid sequence AHSRLLWFGELLPSA FDY (SEQ ID NO: 7).

The present application also includes isolated nucleic acid sequences encoding variants of the CDR sequences and variable region sequences discussed above.

Variant nucleic acid sequences include nucleic acid sequences that hybridize to the nucleic acid sequences encoding the amino acid sequences shown in SEQ ID NOS: 5-10, 2 and 4 and variants thereof under at least moderately stringent hybridization conditions.

(ii) Binding Proteins

Another aspect of the present application is a binding protein, preferably an antibody or antibody fragment, that comprises at least one light chain complementarity determining region of the present application (i.e. one or more of SEQ ID NOS: 8-10) and/or at least one heavy chain complementarity determining region of the present application (i.e. one or more of SEQ ID NO: 5-7). Such a binding protein can be generally referred to herein as "a binding protein of the present application", or preferably "an antibody or antibody fragment of the present application".

In one embodiment, the binding protein comprises the light chain complementarity determining regions 1, 2 and 3 comprising the amino acid sequences SGDKLGDKYAC (SEQ ID NO: 8); QDSKRPS (SEQ ID NO: 9); and QAWDSSTW (SEQ ID NO: 10), respectively; and heavy chain complementarity determining regions 1, 2 and 3 comprising the amino acid sequences SYAMH (SEQ ID NO: 5); VISYDGSNKYYADSVKG (SEQ ID NO: 6); and AHSRLLWFGELLPSAFDY (SEQ ID NO: 7), respectively. The present application also provides a binding protein, preferably an antibody or antibody fragment, that comprises the light chain variable region shown in FIG. 1B (SEQ ID NO: 4) and/or the heavy chain variable region shown in FIG. 1A (SEQ ID NO: 2).

A person skilled in the art will appreciate that the present application includes variants to the specific binding proteins disclosed above, including chemical equivalents to the sequences disclosed above that perform substantially the same function as the binding proteins disclosed above in substantially the same way. A functional variant of a binding protein will be able to bind to the same antigen as the binding proteins disclosed above. In one embodiment, the binding protein binds to IkBβ proteins, including IkBβ isoform 1 (IkBβ1), IkBβ isoform 2 (IkBβ2) and/or a cancer-associated variant of IkBβ.

The inventors have identified the antigen to which the binding proteins of the present application bind. Accordingly, the present application provides binding proteins that bind to IkBβ proteins, including IkBβ isoform 1 (IkBβ1), IkBβ isoform 2 (IkBβ2) and/or a cancer-associated variant of IkBβ.

As mentioned above, the binding protein of the present application binds to the surface of cancer cells and not significantly to the surface of non-cancerous cells. Accordingly, the present application includes binding proteins that bind to the extracellular domain of the cancer-associated variant of IkBβ. The structure of the cancer-associated variant of IkBβ can be predicted by a person skilled in the art using computer modeling. For example, commercially available software or services can be used (See Protein Explorer by Martz, Eric. Submitted on Nov. 30, 2000. Last revised on Apr. 30, 2003. http://molvis.sdsc.edu/visres/molvisfw/titles.jsp). In one embodiment, computer modeling of the protein defined by SEQ ID NO: 30.

In one embodiment, the extracellular domain is comprised in or comprises the amino acids 52 to 97 of SEQ ID NO: 27 or 30.

In another embodiment, the extracellular domain is comprised in or comprises sequence:

```
                                            (SEQ ID NO: 68)
GYVTEDGDTALHLAVIHQHEPFLFLLGFSAGTEYMDLQNDLGQTA.
```

In another embodiment, the extracellular domain comprises amino acids 38 to 98 of SEQ ID NO:27 or 30:

```
                                            (SEQ ID NO: 69)
AELGPGLSWAPLVFGYVTEDGDTALHLAVIQHEPFLDFLLGFSAGTEYMD

LQNDLGQTAL;
or
                                            (SEQ ID NO. 70)
AWLGPGLSWAPLVFGYVTEDGDTALHLAVIQHEPFLDFLLGFSAGTEYMD

LQNDLGQTAL.
```

In another embodiment, the binding protein of the application binds to a peptide comprising amino acids 38 to 102 of SEQ ID NO:27 or 30:

```
                                            (SEQ ID NO: 71)
AELGPGLSWAPLVFGYVTEDGDTALHLAVIQHEPFLDFLLGFSAGTEYMD

LQNDLGQTALHLAA;
or
                                            (SEQ ID NO: 72)
AWLGPGLSWAPLVFGYVTEDGDTALHLAVIQHEPFLDFLLGFSAGTEYMD

LQNDLGQTALHLAA.
```

In certain embodiments, the antibody or antibody fragment comprises all or a portion of a heavy chain constant region, such as an IgG1, IgG2, IgG3, IgG4, IgA1, IgA2, IgE, IgM or IgD constant region. Preferably, the heavy chain constant region is an IgM heavy chain constant region. Furthermore, the antibody or antibody fragment can comprise all or a portion of a kappa light chain constant region or a lambda light chain constant region. Preferably, the light chain constant region is a lambda light chain constant region.

To produce human monoclonal antibodies, antibody producing cells (lymphocytes) can be harvested from a human having cancer and fused with myeloma cells by standard somatic cell fusion procedures thus immortalizing these cells and yielding hybridoma cells. Such techniques are well known in the art, (e.g. the hybridoma technique originally developed by Kohler and Milstein (Nature 256:495-497 (1975)) as well as other techniques such as the human B-cell hybridoma technique (Kozbor et al., Immunol. Today 4:72 (1983)), the EBV-hybridoma technique to produce human monoclonal antibodies (Roder et al., Methods Enzymol, 121: 140-67 (1986)), and screening of combinatorial antibody libraries (Huse et al., Science 246:1275 (1989)). Hybridoma cells can be screened immunochemically for production of antibodies specifically reactive with cancer cells and the monoclonal antibodies can be isolated.

Specific antibodies, or antibody fragments, reactive against particular antigens or molecules, such as antigens or molecules on a cancer cell, may also be generated by screening expression libraries encoding immunoglobulin genes, or portions thereof, expressed in bacteria with cell surface components. For example, complete Fab fragments, VH regions and FV regions can be expressed in bacteria using phage expression libraries (See for example Ward et al., Nature 341:544-546 (1989); Huse et al., Science 246:1275-1281 (1989); and McCafferty et al., Nature 348:552-554 (1990)).

The present application includes all antibodies and antibody fragments that bind to the same antigen as the antibodies or antibody fragments of the present application. A person skilled in the art will appreciate that binding assays can be used to find other antibodies and antibody fragments with the same binding specificities as the antibodies and antibody fragments of the present application. As exemplified, below, a competition binding assay can be used to find such other antibodies.

Before a competition assay is performed using flow cytometry, the minimal concentration of antibody of the present application (Ab1) that gives maximal binding against a fixed number of cancer cells is determined. A total of 106 cells are harvested from exponentially growing cultures and incubated with various antibody concentrations for 1 hr at 4° C. The cells are washed and incubated with a suitable detection antibody for an additional hour at 4° C. After washing, the cells are analyzed by flow cytometry. For each test antibody, a saturation curve is generated from the data by plotting median fluorescence against the antibody concentration.

For the competition assay, cancer cells are prepared as above and treated in duplicate with a fixed concentration of antibody (Ab1). The fixed concentration is the minimal concentration of antibody that generates maximal binding against a fixed number of cancer cells as determined above. Immediately following the addition of the Ab1, varying concentrations of the potential inhibitory antibody (Ab2) is added to each tube and the mixture incubated for 1 hr at 4° C. Both the percent inhibition and change over maximum median fluorescence are calculated by subtracting the background fluorescence (PBS-5% FCS) from the median fluorescence reading for each test sample (Ab1+Ab2). The result is then divided by the median fluorescence of Ab1 alone (maximal binding) minus the background (see below). The percent of inhibition result is obtained by multiplying by 100. The mean of the replicates along with their respective standard error is plotted against antibody concentration. The following formula is used to calculate the percent inhibition:

$$PI=[(MF_{(Ab1+Ab2)}-MF_{Bgd})/(MF_{Ab1}-MF_{Bgd})]\times 100$$

where PI=percent inhibition; MF(Ab1+Ab2)=median fluorescence measured for Ab1+Ab2 mixture; and MFBgd=background median fluorescence with PBS-5% FCS.

Accordingly, the present application provides a binding protein capable of binding an antigen on a cancer cell wherein the binding protein can be identified by a method comprising:

(1) incubating a fixed number of cancer cells with a minimal concentration of a binding protein of the present application, preferably an antibody or antibody fragment (Ab1) that generates maximal binding against the fixed number of cancer cells and measuring median fluorescence of Ab1 ($MF_{Ab1}$);

(2) testing two or more concentrations of a test binding protein (Ab2) by adding Ab2 to the Ab1 and cancer cells, and measuring median fluorescence ($MF_{(Ab1+Ab2)}$);

(3) measuring background median fluorescence ($MF_{bgd}$);

(4) calculating PI, wherein $$PI=[(MF_{(Ab1+Ab2)}-MF_{Bgd})/(MF_{Ab1}-MF_{Bgd})]\times 100;$$

and (5) comparing the PI to a control PI value;

wherein, a PI that has a statistically significant difference from the control PI indicates that the test binding protein is capable of binding the antigen of the present application on the cancer cell.

A person skilled in the art will appreciate that affinity maturation techniques could be used modify the binding proteins or immunoconjugates of the present application by increasing its affinity for its antigen.

Two strategies are routinely used to enhance the binding affinity of an antibody. One approach utilizes the resolution of the crystal structure of the Ab-Ag complex to identify the key residues involved in the antigen binding (Davies D. R., Cohen G. H. 1996. Interactions of protein antigens with antibodies. Proc Natl. Acad. Sci. U.S.A. 93, 7-12). Subsequently, those residues can be mutated to enhance the interaction. The other approach mimics an in vivo antigen stimulation that drives the affinity maturation of immunoglobulin produced by B cells. During the maturation of the immune response, the variable regions of the immunoglobulins are subjected to somatic mutations (Me Heyzer-Williams M. 2003. B-cell signaling mechanism and activation. Fundamental Immunology, Fifth edition, 195-225). This process, highly specific for the immune system, is characterized by the introduction of point mutations at a very high rate. It occurs only within the DNA fragments encoding the variable regions and excludes the conserved domains. The B cells expressing the somatically mutated variant antibody are then subjected to an antigen-mediated selection resulting in the selection of higher affinity immunoglobulin. In order to replicate this phenomenon in vitro, several approaches have been used to introduce mutations either by random or targeted processes. The random mutations can be introduced using error-prone PCR, chain shuffling or mutator E. coli strains (Clackson T. Hoogenboom N. R., Griffiths A. D. and Winter G. 1991 Making antibody fragments using phage display libraries. Nature 352, 624-628, Hawkins R. E., Russell S. J. and Winter G. 1992. Selection of phage antibodies by binding affinity. Mimicking affinity maturation. J. Mol. Biol. 226, 889-896, Low N., Holliger P. and Winter G. 1996. Mimicking somatic hypermutation: affinity maturation of antibodies displayed on bacteriophage using a bacterial mutator strain. J. Mol. Biol. 260, 359-368). This strategy leads to the creation of large libraries in which reactive clones are selected with a display technology such as ribosome, phage or yeast (Min L. (2000). Applications of display technology in protein analysis. Nat. Biotechnol. 18, 1251-1256).

The targeted mutations of the CDRs, especially CDR3 of the light and heavy chains, have been shown to be an effective technique for increasing antibody affinity. Blocks of 3 to 4 amino acids of the CDR3 or specific regions called "hot-spots" are targeted for mutagenesis. Yang et al reported an increase of 420 fold of an anti-HIV gp120 Fab fragment by mutating four CDR residues (Yang W. P., Green K., Pinz-Sweeney S., Briones A. T., Burton D. R. and Barbas C. F. III. 1995. CDR walking mutagenesis for the affinity maturation of a potent human anti-HIV-1 antibody into picomolar range. J. Mol. Biol., 254, 392-403). One mutation in the VL CDR3 combined with three mutations in the VH CDR3 of the C6.5 scFv yielded a 1230 fold increased affinity (Schier R., McCall A., Adams G. P., Marshall K. W., Merrit H., Yin M., Crawford R. S. Weiner L. M., Marks C. and Marks J. D. 1996. Isolation of picomolar affinity anti-c-erbB-2 single-chain Fv by molecular evolution of the complementary determining regions in the center of the antibody binding site. J. Mol. Biol., 263, 551-567).

"Hot spots" are the sequences where somatic hypermutation takes place in vivo (Neuberger M. S and Milstein C. 1995. Somatic hypermutation. Curr. Opin. Immunol. 7, 248-254). The hotspot sequences can be defined as consensus nucleotide sequences in certain codons. The consensus sequence is the tetranucleotide, RGYW, in which R can be either A or G, Y can be C or T and W can be either A or T (Neuberger M. S and Milstein C. 1995. Somatic hypermutation. Curr. Opin. Immunol. 7, 248-254). In addition, the serine residues encoded by the nucleotides AGY are predominantly present in the CDRs regions of the variable domain over those encoded by TCN corresponding to a potential hot-spot sequences (Wagner S. D., Milstein C. and Neuberger M. S. 1995. Codon bias targets mutation. Nature, 376, 732). The structural analysis has shown that the CDR loops contribute the most to the antigen binding, especially the CDR3 loops (Giudicelli V., Chaume D. and Lefranc M. P. 2004. IMGT/V-QUEST, an integrated software program for immunoglobulin and T cell receptor V-J and V-D-J rearrangement analysis. Nucleic Acids Res. 32, 435-440). Therefore, the nucleotide sequence of the CDRs of the heavy and light chains of each antibody of the present application is scanned for the presence of the hot-spot sequences and AGY codons. The identified hot-spots of the CDR regions of the light and heavy chain are compared to the germinal sequences of the heavy and light chains using the International ImMunoGen Tics database (IMGT, http://imgt.cines.fr/textes/vquest/) (Davies D. R., Padlan E. A. and Sheriff S. 1990. Antibody-antigen complexes. Annu. Rev. Biochem. 59, 439-473). A sequence, identical to the germ line, suggest that somatic mutation has not occurred; therefore the random mutations are introduced mimicking the somatic events occurring in vivo. In contrast, a different sequence shows that some somatic mutations have already occurred. It will remain to be determined if the in vivo somatic mutation was optimal. The hot-spots that code for buried or conserved amino acids within the CDRs are not mutagenized. These residues are usually critical for the overall structure and are unlikely to interact with the antigen since they are buried. In addition, the sequences can be compared to the predicted locations in the germ line sequences where somatic mutations occurred predominantly (Tomlinson I. M., Cox J. P. L., Gherardi E., Lesk A. M. and Chotia C. 1995. The structural repertoire of the human Vldomain. EMBO J. 14, 4628-4638, Tomlinson I. M., Walter G., Jones P. T., Dear P. N., Sonnhammer E. L. L. and Winter G. 1996. The imprint of somatic hypermutation on the repertoire of human germline V genes. J. Mol. Biol. 256, 813-817). A similar strategy was applied for the affinity maturation of BL22 scFv. A point mutation introduced in the CDR3 of the heavy resulted in 5 to 10 fold increase in binding activity on various CD22-positive cell lines (Salvatore G., Beers R., Margulies I., Kreitman R. J.

and Pastan I. 2002. Improved cytotoxic activity toward cell lines and fresh leukemia cells of a mutant anti-CD22 immunotoxin obtained by antibody phage display. Clinical Cancer research, 8, 995-1002). Also, the mutation of various amino acids in the CDR1 and CDR2 loops also produced mutant with increase affinity ranging from 3 fold to 7 fold (Ho M., Kreitman J., Onda M. and Pastan I. 2005. In vitro antibody evolution targeting germline hot spots to increase activity of an anti-CD22 immunotoxin. J. Biol. Chem., 280, 607-617).

After mutations are introduced, either by random or targeted processes, the antibodies are expressed and assessed for function. For instance, functional screening can be based on binding. Once function is assessed, then DNA sequencing of the chosen antibodies can be carried out using known methods.

In another embodiment, the anchored periplasmic expression (APEx) method described by Harvey, B et al (PNAS 2004 Jun. 22; 101(25): 9193-8) is used for affinity maturation of the binding proteins or immunoconjugates of the present application.

Accordingly, the present application includes binding proteins of the present application that have been affinity maturized to increase the affinity of the binding protein to IkBβ proteins, including IkBβ isoform 1 (IkBβ1), IkBβ isoform 2 (IkBβ2) and/or a cancer-associated variant of IkBβ.

The present application also provides compositions comprising the binding proteins of the present application, preferably antibodies and antibody fragments, with a pharmaceutically acceptable excipient, carrier, buffer or stabilizer.

Further, the present application provides isolated nucleic acid sequences encoding the binding proteins of the present application. The present application also includes variants to these nucleic acid sequences. For example, the variants include nucleotide sequences that hybridize to the nucleic acid sequences encoding the binding proteins of the present application under at least moderately stringent hybridization conditions.

(C) Cancer-Associated Antigen

The inventors have identified the antigen to which the binding proteins of the present application bind (including IkBβ proteins, such as IkBβ isoform 1 (IkBβ1), IkBβ isoform 2 (IkBβ2) and/or cancer-associated variant of IkBβ). The cancer-associated antigen is expressed on the surface of cancer cells and is not significantly expressed on the surface of normal cells. Accordingly, the present application includes an isolated protein that can specifically bind with one of the binding proteins of the present application, and nucleic acid sequences and uses thereof.

The present application includes a novel cancer-associated antigen, namely a cancer-associated variant of IkBβ. In one embodiment, the cancer-associated variant of IkBβ is expressed on the surface of cancer cells and not significantly on non-cancerous cells. In a further embodiment, the cancer-associated variant of IkBβ has the same function as IkBβ, as an inhibitory regulator of NFk-B, but a different localization in the cell (i.e. on the cell membrane). In another embodiment, the cancer-associated variant of IkBβ comprises the amino acid sequence defined by SEQ ID NO:32 and/or 36. In a further embodiment, the cancer-associated variant of IkBβ comprises the amino acid sequence defined by SEQ ID NO:30. In an additional embodiment, cancer-associated variant of IkBβ consists of the amino acid sequence defined by SEQ ID NO:30. In a further embodiment, the cancer-associated variant of IkBβ comprises the sequence of SEQ ID NO:27 in which one or more amino acids selected from positions 26, 27, 31, 34, 39, 106, 111, and 112 is substituted with another amino acid or is chemically modified. In a further embodiment, the substitution or chemical modification results in an increase in the hydrophobicity of the region where the change was made relative to the non-modified protein (i.e. SEQ ID NO:27). In an additional embodiment, the substitution is one or more of the following: P026V, D027L, P031V, P034V, E039W, E106V, E111V and/or K112A. In another embodiment of the present application, the cancer-associated variant of 1KBβ, comprises 1KBβ with one or more transmembrane domains not normally present in 1KBβ. In one embodiment, the transmembrane domain comprises the amino acid sequence of SEQ ID NO: 53 or 54. In one embodiment, the cancer-associated variant of IkBβ is a variant of IkBβ2.

A person skilled in the art will appreciate that the present application includes variants to the amino acid sequences discussed above, including chemical equivalents to the sequences disclosed in the present application. Such equivalents include proteins that perform substantially the same function as the specific proteins disclosed herein in substantially the same way. For example, equivalents include, without limitation, conservative amino acid substitutions.

In one embodiment, the variant amino acid sequences have at least 50%, preferably at least 60%, more preferably at least 70%, most preferably at least 80%, even more preferably at least 90%, and even most preferably at least 95% sequence identity to SEQ ID NOS:30, 32, 36, 53 or 54.

The present application includes the use of the novel cancer-associated antigen of the present application. For example, the use of the novel cancer-associated antigen of the present application to generate binding proteins and immunoconjugates that can be used to treat or prevent cancer or that can be used to detect or monitor cancer in a subject or in the manufacture of a medicament to treat or prevent cancer.

Further, the present application provides isolated nucleic acid sequences that encode the novel cancer-associated antigen of the present application. The present application also includes variants to these nucleic acid sequences. For example, the variants include nucleotide sequences that hybridize to the nucleic acid sequences that encode the novel-cancer associated antigen of the present application under at least moderately stringent hybridization conditions.

(D) Immunoconjugates

The present application also includes an immunoconjugate comprising (1) a binding protein of the present application, preferably an antibody or antibody fragment, that has been attached to (2) an effector molecule. In one embodiment, the binding protein of the present application binds to an antigen or molecule on a cancer cell. In one embodiment, the antigen or molecule comprises an IkBβ protein, such as IkBβ isoform 1 (IkBβ1), IkBβ isoform 2 (IkBβ2) and/or a cancer-associated variant of IkBβ.

In a preferred embodiment the effector molecule is (i) a label, which can generate a detectable signal, directly or indirect, or (ii) a cancer therapeutic agent, which is either cytotoxic, cytostatic or otherwise prevents or reduces the ability of the cancer cells to divide and/or metastasize. Such an immunoconjugate can be generally referred to as "the immunoconjugate of the present application" herein.

In an embodiment of the present application, the effector molecule is a cancer therapeutic agent. The cancer therapeutic agent is preferably a toxin that is either cytotoxic, cytostatic or otherwise prevents or reduces the ability of the cancer cells to divide and/or metastasize. Accordingly, one aspect of the present application is an immunoconjugate comprising (1) a binding protein of the present application, preferably an antibody or antibody fragment, attached to (2) a cancer therapeutic agent, such as a cytotoxin.

In another embodiment, the immunoconjugate is internalized and the cancer therapeutic agent is a cytotoxin that blocks the protein synthesis of the cell, therein leading to cell death. Importantly, since most normal cells do not widely express the antigen present on the cancer cells, they cannot bind and internalize the immunoconjugate, and are protected from the killing effect of the toxin or other cancer therapeutic agents.

A variety of effector molecules may be used in the immunoconjugates of the present application and a number of such effector molecules are intracellularly active molecules. Accordingly, in an embodiment of the present application, the immunoconjugate is internalized by the cancer cell.

In preferred embodiments, the effector molecule is a cancer therapeutic agent, more preferably a cytotoxin that comprises a polypeptide having ribosome-inactivating activity including, without limitation, gelonin, bouganin, saporin, ricin, ricin A chain, bryodin, diphtheria toxin, restrictocin, Pseudomonas exotoxin A and variants thereof. When the protein is a ribosome-inactivating protein, the immunoconjugate must be internalized upon binding to the cancer cell in order for the protein to be cytotoxic to the cells. Accordingly, in an embodiment of the present application, the effector molecule is a cytotoxin and the immunoconjugate is internalized by the cancer cell.

In one embodiment, the toxin is bouganin or Pseudomonas exotoxin A, and variants thereof. In another embodiment, the toxin is modified bouganin or a truncated form of Pseudomonas exotoxin A that lacks the cell binding domain. In a further embodiment, the toxin is a bouganin substantially devoid of T-cell epitopes or a truncated form of Pseudomonas exotoxin A that consists of amino acids 252-608.

In other nonlimiting embodiments, the cancer therapeutic agent comprises an agent that acts to disrupt DNA. Thus, the cancer therapeutic agents may be selected, without limitation, from enediynes (e.g., calicheamicin and esperamicin) and non-enediyne small molecule agents (e.g., bleomycin, methidiumpropyl-EDTA-Fe(II)). Other cancer therapeutic agents useful in accordance with the present application include, without limitation, daunorubicin, doxorubicin, distamycin A, cisplatin, mitomycin C, ecteinascidins, duocarmycin/CC-1065, and bleomycin/pepleomycin.

In other nonlimiting embodiments, the cancer therapeutic agent comprises an agent that acts to disrupt tubulin. Such agents may comprise, without limitation, rhizoxin/maytansine, paclitaxel, vincristine and vinblastine, colchicine, auristatin dolastatin 10 MMAE, and peloruside A.

In other nonlimiting embodiments, the cancer therapeutic portion of an immunoconjugate of the present application may comprise an alkylating agent including, without limitation, Asaley NSC 167780, AZQ NSC 182986, BCNU NSC 409962, Busulfan NSC 750, carboxyphthalatoplatinum NSC 271674, CBDCA NSC 241240, CCNU NSC 79037, CHIP NSC 256927, chlorambucil NSC 3088, chlorozotocin NSC 178248, cis-platinum NSC 119875, clomesone NSC 338947, cyanomorpholinodoxorubicin NSC 357704, cyclodisone NSC 348948, dianhydrogalactitol NSC 132313, fluorodopan NSC 73754, hepsulfam NSC 329680, hycanthone NSC 142982, melphalan NSC 8806, methyl CCNU NSC 95441, mitomycin C NSC 26980, mitozolamide NSC 353451, nitrogen mustard NSC 762, PCNU NSC 95466, piperazine NSC 344007, piperazinedione NSC 135758, pipobromanm NSC 25154, porfiromycin NSC 56410, spirohydantoin mustard NSC 172112, teroxirone NSC 296934, tetraplatin NSC 363812, thiotepa NSC 6396, triethylenemelamine NSC 9706, uracil nitrogen mustard NSC 34462, and Yoshi-864 NSC 102627.

In other nonlimiting embodiments, the cancer therapeutic agent portion of the immunoconjugate of the present application may comprise an antimitotic agent including, without limitation, allocolchicine NSC 406042, Halichondrin B NSC 609395, colchicine NSC 757, colchicine derivative NSC 33410, dolastatin 10 NSC 376128 (NG-auristatin derived), maytansine NSC 153858, rhizoxin NSC 332598, taxol NSC 125973, taxol derivative NSC 608832, thiocolchicine NSC 361792, trityl cysteine NSC 83265, vinblastine sulfate NSC 49842, and vincristine sulfate NSC 67574.

In other nonlimiting embodiments, the cancer therapeutic agent portion of the immunoconjugate of the present application may comprise a topoisomerase I inhibitor including, without limitation, camptothecin NSC 94600, camptothecin, Na salt NSC 100880, aminocamptothecin NSC 603071, camptothecin derivative NSC 95382, camptothecin derivative NSC 107124, camptothecin derivative NSC 643833, camptothecin derivative NSC 629971, camptothecin derivative NSC 295500, camptothecin derivative NSC 249910, camptothecin derivative NSC 606985, camptothecin derivative NSC 374028, camptothecin derivative NSC 176323, camptothecin derivative NSC 295501, camptothecin derivative NSC 606172, camptothecin derivative NSC 606173, camptothecin derivative NSC 610458, camptothecin derivative NSC 618939, camptothecin derivative NSC 610457, camptothecin derivative NSC 610459, camptothecin derivative NSC 606499, camptothecin derivative NSC 610456, camptothecin derivative NSC 364830, camptothecin derivative NSC 606497, and morpholinodoxorubicin NSC 354646.

In other nonlimiting embodiments, cancer therapeutic agent portion of the immunoconjugate of the present application may comprise a topoisomerase II inhibitor including, without limitation, doxorubicin NSC 123127, amonafide NSC 308847, m-AMSA NSC 249992, anthrapyrazole derivative NSC 355644, pyrazoloacridine NSC 366140, bisantrene HCL NSC 337766, daunorubicin NSC 82151, deoxydoxorubicin NSC 267469, mitoxantrone NSC 301739, menogaril NSC 269148, N,N-dibenzyl daunomycin NSC 268242, oxanthrazole NSC 349174, rubidazone NSC 164011, VM-26 NSC 122819, and VP-16 NSC 141540.

In other nonlimiting embodiments, the cancer therapeutic agent portion of the immunoconjugate of the present application may comprise a RNA or DNA antimetabolite including, without limitation, L-alanosine NSC 153353, 5-azacytidine NSC 102816, 5-fluorouracil NSC 19893, acivicin NSC 163501, aminopterin derivative NSC 132483, aminopterin derivative NSC 184692, aminopterin derivative NSC 134033, an antifol NSC 633713, an antifol NSC 623017, Baker's soluble antifol NSC 139105, dichlorallyl lawsone NSC 126771, brequinar NSC 368390, ftorafur (prodrug) NSC 148958,5,6-dihydro-5-azacytidine NSC 264880, methotrexate NSC 740, methotrexate derivative NSC 174121, N-(phosphonoacetyl)-L-aspartate (PALA) NSC 224131, pyrazofurin NSC 143095, trimetrexate NSC 352122, 3-HP NSC 95678, 2'-deoxy-5-fluorouridine NSC 27640,5-HP NSC 107392, alpha-TGDR NSC 71851, aphidicolin glycinate NSC 303812, ara-C NSC 63878,5-aza-2'-deoxycytidine NSC 127716, beta-TGDR NSC 71261, cyclocytidine NSC 145668, guanazole NSC 1895, hydroxyurea NSC 32065, inosine glycodialdehyde NSC 118994, macbecin II NSC 330500, pyrazoloimidazole NSC 51143, thioguanine NSC 752, and thiopurine NSC 755.

In another nonlimiting embodiment, the therapeutic portion of the immunoconjugates may be a nucleic acid. Nucleic acids that may be used include, but are not limited to, antisense RNA, genes or other polynucleotides, nucleic acid analogs such as thioguanine and thiopurine.

The present application further provides immunoconjugates comprising (i) a binding protein of the present application, preferably an antibody or antibody fragment, attached to (2) an effector molecule, wherein the effector molecule is a label, which can generate a detectable signal, indirectly or directly. These immunoconjugates can be used for research or diagnostic applications, such as for the in vivo detection of cancer. The label is preferably capable of producing, either directly or indirectly, a detectable signal. For example, the label may be radio-opaque or a radioisotope, such as $^3$H, $^{14}$C, $^{32}$P, $^{35}$S, $^{123}$I, $^{125}$I, $^{131}$I; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion.

In another embodiment, the immunoconjugate is detectable indirectly. For example, a secondary antibody that is specific for the immunoconjugate and contains a detectable label can be used to detect the immunoconjugate.

The binding protein of the present application, preferably an antibody or antibody fragment, may be "attached to" the effector molecule by any means by which the binding protein can be associated with, or linked to, the effector molecule. For example, the binding protein may be attached to the effector molecule by chemical or recombinant means. Chemical means for preparing fusions or conjugates are known in the art and can be used to prepare the immunoconjugate. The method used to conjugate the binding protein and effector molecule must be capable of joining the binding protein with the effector molecule without interfering with the ability of the binding protein to bind to the antigen on the cancer cell.

The binding protein of the present application may be linked indirectly to the effector molecule. For example, the binding protein may be directly linked to a liposome containing the effector molecule of one of several types. The effector molecule(s) and/or binding protein may also be bound to a solid surface.

In one embodiment, the binding protein, preferably an antibody or antibody fragment, and effector molecule are both proteins and can be conjugated using techniques well known in the art. There are several hundred crosslinkers available that can conjugate two proteins. (See for example "Chemistry of Protein Conjugation and Crosslinking". 1991, Shans Wong, CRC Press, Ann Arbor). The crosslinker is generally chosen based on the reactive functional groups available or inserted on the binding protein, preferably an antibody or antibody fragment, and/or effector molecule. In addition, if there are no reactive groups, a photoactivatable crosslinker can be used. In certain instances, it may be desirable to include a spacer between the binding protein, preferably an antibody or antibody fragment, and effector molecule. Crosslinking agents known to the art include the homobifunctional agents: glutaraldehyde, dimethyladipimidate and Bis(diazobenzidine) and the heterobifunctional agents: m Maleimidobenzoyl-N-Hydroxysuccinimide and Sulfo-m Maleimidobenzoyl-N-Hydroxysuccinimide.

In certain instances, the binding protein of the present application may be engineered with specific residues for chemical attachment of the effector molecule. Specific residues used for chemical attachment of molecule known to the art include lysine and cysteine. The crosslinker is chosen based on the reactive functional groups inserted on the binding protein, and available on the effector molecule.

A binding protein-effector molecule protein fusion may also be prepared using recombinant DNA techniques. In such a case a DNA sequence encoding the binding protein is fused to a DNA sequence encoding the effector molecule, resulting in a chimeric DNA molecule. The chimeric DNA sequence is transfected into a host cell that expresses the fusion protein. The fusion protein can be recovered from the cell culture and purified using techniques known in the art.

Examples of attaching an effector molecule, which is a label, to the binding protein include the methods described in Hunter, et al., Nature 144:945 (1962); David, et al., Biochemistry 13:1014 (1974); Pain, et al., J. Immunol. Meth. 40:219 (1981); Nygren, J. Histochem. and Cytochem. 30:407 (1982); Wensel and Meares, Radioimmunoimaging And Radioimmunotherapy, Elsevier, N.Y. (1983); and Colcher et al., "Use Of Monoclonal Antibodies As Radiopharmaceuticals For The Localization Of Human Carcinoma Xenografts In Athymic Mice", Meth. Enzymol., 121:802-16 (1986).

In one embodiment, the immunoconjugate comprises the amino acid sequence defined by SEQ ID NO:67. The present application also includes variants of this sequence.

The present application also provides for isolated nucleic acid sequences that encode the immunoconjugates of the present application. In one embodiment, the isolated nucleic acid sequence encodes a protein comprising the amino acid sequence defined by SEQ ID NO: 67. In another embodiment, the isolated nucleic acid sequence comprises SEQ ID NO:66.

The present application also includes variants to these nucleic acid sequences. For example, the variants include nucleotide sequences that hybridize to the nucleic acid sequences encoding the immunoconjugates of the present application under at least moderately stringent hybridization conditions.

(E) Preparation of Proteins

A person skilled in the art will appreciate that the proteins of the present application, such as the light and heavy complementarity determining regions, the light and heavy chain variable regions, antibodies and antibody fragments, immunoconjugates and novel cancer-associated antigen of the present application, may be prepared in any of several ways, but is most preferably prepared using recombinant methods.

Accordingly, the nucleic acid molecules of the present application may be incorporated in a known manner into an appropriate expression vector which ensures good expression of the proteins of the present application. Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", which means that the expression vectors contain a nucleic acid molecule of the present application and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The present application therefore contemplates a recombinant expression vector of the present application containing a nucleic acid molecule of the present application, or a fragment thereof, and the necessary regulatory sequences for the transcription and translation of the inserted protein-sequence.

Suitable regulatory sequences may be derived from a variety of sources, including bacterial, fungal, viral, mammalian, or insect genes (For example, see the regulatory sequences described in Goeddel, Gene Expression Technology Methods in Enzymology 185, Academic Press, San Diego, Calif. (1990)). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The recombinant expression vectors of the present application may also contain a selectable marker gene which facilitates the selection of host cells transformed or transfected with a recombinant molecule of the present application. Examples of selectable marker genes are genes encoding a protein such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the present application and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of the target recombinant protein by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMal (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Recombinant expression vectors can be introduced into host cells to produce a transformed host cell. The terms "transformed with", "transfected with", "transformation" and "transfection" are intended to encompass introduction of nucleic acid (e.g. a vector) into a cell by one of many possible techniques known in the art. The term "transformed host cell" as used herein is intended to also include cells capable of glycosylation that have been transformed with a recombinant expression vector of the present application. Prokaryotic cells can be transformed with nucleic acid by, for example, electroporation or calcium-chloride mediated transformation. For example, nucleic acid can be introduced into mammalian cells via conventional techniques such as calcium phosphate or calcium chloride co-precipitation, DEAE-dextran mediated transfection, lipofectin, electroporation or microinjection. Suitable methods for transforming and transfecting host cells can be found in Sambrook et al. (Molecular Cloning: A Laboratory Manual, 3rd Edition, Cold Spring Harbor Laboratory Press, 2001), and other laboratory textbooks.

Suitable host cells include a wide variety of eukaryotic host cells and prokaryotic cells. For example, the proteins of the present application may be expressed in yeast cells or mammalian cells. Other suitable host cells can be found in Goeddel, Gene Expression Technology Methods in Enzymology 185, Academic Press, San Diego, Calif. (1991). In addition, the proteins of the present application may be expressed in prokaryotic cells, such as *Escherichia coli* (Zhang et al., Science 303(5656): 371-3 (2004)). In addition, a *Pseudomonas* based expression system such as *Pseudomonas fluorescens* can be used (US Patent Application Publication No. US 2005/0186666, Schneider, Jane C et al.).

Yeast and fungi host cells suitable for carrying out the present application include, but are not limited to *Saccharomyces cerevisiae*, the genera *Pichia* or *Kluyveromyces* and various species of the genus *Aspergillus*. Examples of vectors for expression in yeast *S. cerevisiae* include pYepSec1 (Baldari. et al., Embo J. 6:229-234 (1987)), pMFa (Kurjan and Herskowitz, Cell 30:933-943 (1982)), pJRY88 (Schultz et al. Gene 54:113-123 (1987)), andpYES2 (Invitrogen Corporation, San Diego, Calif.). Protocols for the transformation of yeast and fungi are well known to those of ordinary skill in the art (see Hinnen et al, Proc. Natl. Acad. Sci. USA 75:1929 (1978); Itoh et al, J. Bacteriology 153:163 (1983), and Cullen et al. (Bio/Technology 5:369 (1987)).

Mammalian cells suitable for carrying out the present application include, among others: COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (Seed, B., Nature 329:840 (1987)) and pMT2PC (Kaufman et al., EMBO J. 6:187-195 (1987)).

Given the teachings provided herein, promoters, terminators, and methods for introducing expression vectors of an appropriate type into plant, avian, and insect cells may also be readily accomplished. For example, within one embodiment, the proteins of the present application may be expressed from plant cells (see Sinkar et al., J. Biosci (Bangalore) 11:47-58 (1987), which reviews the use of *Agrobacterium rhizogenes* vectors; see also Zambryski et al., Genetic Engineering, Principles and Methods, Hollaender and Setlow (eds.), Vol. VI, pp. 253-278, Plenum Press, New York (1984), which describes the use of expression vectors for plant cells, including, among others, PAPS2022, PAPS2023, and PAPS2034).

Insect cells suitable for carrying out the present application include cells and cell lines from *Bombyx, Trichoplusia* or *Spodotera* species. Baculovirus vectors available for expression of proteins in cultured insect cells (SF 9 cells) include the pAc series (Smith et al., Mol. Cell. Biol. 3:2156-2165 (1983)) and the pVL series (Lucklow, V. A., and Summers, M. D., Virology 170:31-39 (1989)).

Alternatively, the proteins of the present application may also be expressed in non-human transgenic animals such as rats, rabbits, sheep and pigs (Hammer et al. Nature 315: 680-683 (1985); Palmiter et al. Science 222:809-814 (1983);

Brinster et al. Proc. Natl. Acad. Sci. USA 82:4438-4442 (1985); Palmiter and Brinster Cell 41:343-345 (1985) and U.S. Pat. No. 4,736,866).

The proteins of the present application may also be prepared by chemical synthesis using techniques well known in the chemistry of proteins such as solid phase synthesis (Merrifield, J. Am. Chem. Assoc. 85:2149-2154 (1964); Frische et al., J. Pept. Sci. 2(4): 212-22 (1996)) or synthesis in homogenous solution (Houbenweyl, Methods of Organic Chemistry, ed. E. Wansch, Vol. 15 I and II, Thieme, Stuttgart (1987)).

N-terminal or C-terminal fusion proteins comprising the proteins of the present application conjugated with other molecules, such as proteins may be prepared by fusing, through recombinant techniques. The resultant fusion proteins contain a protein of the present application fused to the selected protein or marker protein as described herein. The recombinant protein of the present application may also be conjugated to other proteins by known techniques. For example, the proteins may be coupled using heterobifunctional thiol-containing linkers as described in WO 90/10457, N-succinimidyl-3-(2-pyridyldithio-proprionate) or N-succinimidyl-5 thioacetate. Examples of proteins which may be used to prepare fusion proteins or conjugates include cell binding proteins such as immunoglobulins, hormones, growth factors, lectins, insulin, low density lipoprotein, glucagon, endorphins, transferrin, bombesin, asialoglycoprotein glutathione-5-transferase (GST), hemagglutinin (HA), and truncated myc.

Accordingly, the present application provides a recombinant expression vector comprising the nucleic acid sequences that encode the proteins of the present application, such as the light and heavy chain complementarity determining regions, the light and heavy chain variable regions, the binding proteins, such as antibodies and antibody fragments, immunoconjugates of the present application and novel isolated proteins of the present application. Further, the present application provides a host cell comprising the nucleic acid sequences or recombinant expression vectors of the present application.

(F) Therapeutic Methods and Pharmaceutical Compositions of the Binding Proteins and Immunotoxins The inventors have shown that the binding proteins of the present application show specificity for IkBβ proteins, including IkBβ, IkBβ2 and a cancer-associated variant of IkBβ. IkBβ proteins are normally intracellular. However, the inventors have shown that cancer cells express a variant of IkBβ which is detectable on the surface of cancer cells. Thus, the inventors have shown that the binding proteins of the present application show specificity for cancer cells. In addition, the inventors have shown that the binding proteins of the present application are internalized by cancer cells. Thus, the binding proteins of the present application can be used for the targeted delivery of bioactive or medically relevant agents, such as imaging, radioactive or cytotoxic agents.

In one embodiment, the present application provides a method of treating or preventing cancer, comprising administering to a subject having or suspected of having cancer an effective amount of the immunoconjugate of the present application. In another embodiment, the present application provides the use of an effective amount of the immunoconjugate of the present application for the manufacture of a medicament for treating or preventing cancer. Furthermore, the present application provides the use of an effective amount of the immunoconjugate of the present application, further comprising the use of an additional cancer therapeutic agent for the manufacture of a medicament for simultaneous, separate or sequential treatment or prevention of cancer. The present application also provides the use of an effective amount of the immunoconjugate of the present application for treating or preventing cancer. Further, the present application provides the use of an effective amount of the immunoconjugate of the present application, further comprising the use of an additional cancer therapeutic agent for simultaneous, separate or sequential treatment or prevention of cancer.

In one embodiment of the present application, cancer includes, without limitation, stomach cancer, colon cancer, prostate cancer as well as cervical cancer, uterine cancer, ovarian cancer, pancreatic cancer, kidney cancer, liver cancer, head and neck cancer, squamous cell carcinoma, gastrointestinal cancer, breast cancer (such as carcinoma, ductal, lobular, and nipple), lung cancer, non-Hodgkin's lymphoma, multiple myeloma, leukemia (such as acute lymphocytic leukemia, chronic lymphocytic leukemia, acute myelogenous leukemia, and chronic myelogenous leukemia), brain cancer, neuroblastoma, sarcomas, rectum cancer, bladder cancer, pancreatic cancer, endometrial cancer, plasmacytoma, lymphoma, and melanoma. In another embodiment, the cancer is colon cancer, pancreatic cancer, kidney cancer, liver cancer, breast cancer, skin cancer, ovarian cancer, head and neck cancer, prostate cancer or lung cancer. In an additional embodiment, the cancer is colon cancer, pancreatic cancer or kidney cancer.

The ability of the immunoconjugate of the present application to selectively inhibit or destroy cells having cancer may be readily tested in vitro using cancer cell lines. The selective inhibitory effect of the immunoconjugates of the present application may be determined, for example by demonstrating the selective inhibition of cellular proliferation of the cancer cells.

Toxicity may also be measured based on cell viability, for example, the viability of cancer and normal cell cultures exposed to the immunoconjugate may be compared. Cell viability may be assessed by known techniques, such as trypan blue exclusion assays.

In another example, a number of models may be used to test the effectiveness of the immunoconjugates of the present application. Thompson, E. W. et al. (Breast Cancer Res. Treatment 31:357-370 (1994)) has described a model for the determination of invasiveness of human breast cancer cells in vitro by measuring tumor cell-mediated proteolysis of extracellular matrix and tumor cell invasion of reconstituted basement membrane (collagen, laminin, fibronectin, Matrigel or gelatin). Other applicable cancer cell models include cultured ovarian adenocarcinoma cells (Young, T. N. et al. Gynecol. Oncol. 62:89-99 (1996); Moore, D. H. et al. Gynecol. Oncol. 65:78-82 (1997)), human follicular thyroid cancer cells (Demeure, M. J. et al., World J. Surg. 16:770-776 (1992)), human melanoma (A-2058) and fibrosarcoma (HT-1080) cell lines (Mackay, A. R. et al. Lab. Invest. 70:781 783 (1994)), and lung squamous (HS-24) and adenocarcinoma (SB-3) cell lines (Spiess, E. et al. J. Histochem. Cytochem. 42:917-929 (1994)). An in vivo test system involving the implantation of tumors and measurement of tumor growth and metastasis in athymic nude mice has also been described (Thompson, E. W. et al., Breast Cancer Res. Treatment 31:357-370 (1994); Shi, Y. E. et al. Cancer Res. 53:1409-1415 (1993)).

The immunoconjugates of the present application may be formulated into pharmaceutical compositions for administration to subjects in a biologically compatible form suitable for administration in vivo. The substances may be administered to living organisms including humans, and animals. Administration of a therapeutically active amount of the pharmaceutical compositions of the present application is defined as an amount effective, at dosages and for periods of time necessary to achieve the desired result. For example, a therapeutically active amount of a substance may vary according to factors such as the disease state, age, sex, and weight of the individual, and the ability of the recombinant protein of the present application to elicit a desired response in the individual. Dosage regime may be adjusted to provide the optimum therapeutic response. For example, several divided doses may be administered daily or the dose may be proportionally reduced as indicated by the exigencies of the therapeutic situation.

Accordingly, the present application provides a pharmaceutical composition for treating or preventing cancer comprising the immunoconjugates of the present application, and a pharmaceutically acceptable carrier, diluent or excipient. In a preferred embodiment, the effector molecule of the immunoconjugate in the pharmaceutical composition is a cancer therapeutic agent, more preferably a toxin.

The pharmaceutical preparation comprising the immunoconjugate of the present application may be administered systemically. The pharmaceutical preparation may be administered directly to the cancer site. Depending on the route of administration, the immunoconjugate may be coated in a material to protect the compound from the action of enzymes, acids and other natural conditions that may inactivate the compound.

In accordance with one aspect of the present application, the immunoconjugate is delivered to the patient by direct administration. The present application contemplates the pharmaceutical composition being administered in at least an amount sufficient to achieve the endpoint, and if necessary, comprises a pharmaceutically acceptable carrier.

The present application also provides methods for reducing the risk of post-surgical complications comprising administering an effective amount of the immunoconjugate of the present application before, during, or after surgery to treat cancer.

The compositions described herein can be prepared by per se known methods for the preparation of pharmaceutically acceptable compositions that can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, 20th ed. Mack Publishing Company, Easton, Pa, USA, 2000). On this basis, the compositions include, albeit not exclusively, solutions of the substances in association with one or more pharmaceutically acceptable vehicles or diluents, and contained in buffered solutions with a suitable pH and iso-osmotic with the physiological fluids.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (such as Tween), alcohols, polyols, glycerin and vegetable oils, for example. Extemporaneous injection solutions and suspensions may be prepared from sterile powders, granules, tablets, or concentrated solutions or suspensions. Immunoconjugate may be supplied, for example but not by way of limitation, as a lyophilized powder which is reconstituted with sterile water or saline prior to administration to the patient.

Pharmaceutical compositions of the present application may comprise a pharmaceutically acceptable carrier. Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1(2,3-dioleyloxy)propyl)N,N,N-trimethylammonium chloride (DOTMA), diolesylphosphotidyl-ethanolamine (DOPE), and liposomes. Such compositions should contain a therapeutically effective amount of the compound, together with a suitable amount of carrier so as to provide the form for direct administration to the patient.

The composition may be in the form of a pharmaceutically acceptable salt which includes, without limitation, those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

In various embodiments of the present application, the pharmaceutical composition is directly administered systemically or directly to the area of the tumor(s).

The pharmaceutical compositions may be used in methods for treating animals, including mammals, preferably humans, with cancer. The dosage and type of immunoconjugate to be administered will depend on a variety of factors which may be readily monitored in human subjects. Such factors include the etiology and severity (grade and stage) of the cancer.

Clinical outcomes of cancer treatments using the immunoconjugates of the present application are readily discernable by one of skill in the relevant art, such as a physician. For example, standard medical tests to measure clinical markers of cancer may be strong indicators of the treatment's efficacy. Such tests may include, without limitation, physical examination, performance scales, disease markers, 12-lead ECG, tumor measurements, tissue biopsy, cytoscopy, cytology, longest diameter of tumor calculations, radiography, digital imaging of the tumor, vital signs, weight, recordation of adverse events, assessment of infectious episodes, assessment of concomitant medications, pain assessment, blood or serum chemistry, urinalysis, CT scan, and pharmacokinetic analysis. Furthermore, synergistic effects of a combination therapy comprising the immunoconjugate and another cancer therapeutic may be determined by comparative studies with patients undergoing monotherapy.

In the majority of approved cancer therapies, the cancer therapy is used in combination with other cancer therapies. Accordingly, the present application provides a method of preventing or treating cancer using the immunoconjugate of the present application in combination with at least one additional cancer therapy. The other cancer therapy may be administered prior to, overlapping with, concurrently, and/or after administration of the immunoconjugate. When administered concurrently, the immunoconjugate and the other cancer therapeutic may be administered in a single formulation or in separate formulations, and if separately, then optionally, by different modes of administration. The combination of one or more immunoconjugates and one or more other cancer therapies may synergistically act to combat the tumor or cancer. The other cancer therapies include, without limitation, other cancer therapeutic agents including, without limitation, 2,2',2'-trichlorotriethylamine hydrochloride 4,4'-(1,2-Ethanediyl)bis(1-iso¬" butoxycarbonylox¬" dimethyl-2,6-piperazinedione, 5,6-dihydro-5-azacytidine, 5-hydroxy-2- formylpyridine thiosemicarbazone, 6-azauridine, 6-diazo-5-oxo-L-norleucine, abrin, acivicin, aclarubicin, aldesleukin, alemtuzumab, allocolchicine, alpha-fetoprotein, alpha-thiodeoxyguanosine, altretamine, aminocamptothecin, aminoglutethimide, aminopterin, amonafide dihydrochloride, amonafide L-malate, amsacrine, anastrozole, ancitabine hydrochloride, angiogenin, antisense oligonucleotides, angiostatin, anthramycin, anthrapyrazole, aphidicolin glycinate, asparaginase, auristatin E, autologous cells or tissues, azacitidine, azaserine, aziridine, *Bacillus* Calmette-Guerin, *Bacillus* Calmette-Guerin live vaccine, benzotepa, betamethasone, beta-thioguanine deoxyriboside, bevacizumab, biomycin, bicalutamide, bisantrene, bleomycin, boldenone, brequinar, buserelin, busulfan, cactinomycin, calicheamicin, calusterone, capecitabine, carboplatin, carboquone, carboxyphthalatoplatinum, carcinoembryonic antigen peptide 1, carcinoembryonic antigen peptide 1-6D, carmustine, carubicin, carzinophilin A, CC-1065, cetuximab, chlorambucil, chlormadinone acetate, chlorozotocin, chromomycins, cisplatin, cladribine, clomesone, colchicine, colchicine derivative, cortisol, cortisone, cyanomorpholinodoxorubicin, cyclodisone, cyclophosphamide, cytarabine, cytochalasin B, dacarbazine, dactinomycin, dasatinib, daunorubicin, decitabine, demecolcine, denileukin diftitox, deoxydoxorubicin, dexamethasone, dianhydrogalactitol, diaziquone, dichloroallyl lawsone, diphtheria toxin, distamycin A, docetaxel, dolastatin 10, doxifluridine, doxorubicin, droloxifene, dromostanolone propionate, duborimycin, Duocarmycin A, Duocarmycin SA, edatrexate, eflornithine, elliptinium, emetine, emitefur, endostatin, enocitabine, epirubicin, epitiostanol, erlotinib hydrochloride, esperamicin, estramustine phosphate sodium, ethidium bromide, ethoglucid, etoposide, fadrozole, fenretinide, floxuridine, fludarabine, fluorodopan, flutamide, formestane, fosfestrol, fotemustine, gallium nitrate, gefitinib, gemcitabine hydrochloride, gemtuzumab ozogamicin, glucocorticoid, goserelin, gramicidin D, guanazole, halichondrin B, hepsulfam, hexestrol, human chorionic gonadotropin, hycanthone, hydroxyurea, idarubicin, ifosamide, imatinib mesylate, improsulfan, inosine glycodialdehyde, interferons, interferon-alpha, interferon-beta, interferon-gamma, interleukin-12, interleukin-15, interleukin-18, interleukin-1, interleukin-2, interleukin-2, interleukin-6, interleukins, irinotecan, iproplatin, L-alanosine, lapatinib ditosylate, irinotecan hydrochloride, lentinan, letrozole, leucovorin calcium, leuprolide acetate, leuprolide acetate, levamisole, lidocaine, lomustine, lomustine, lonidamine, lucorteum, lymphokines, lymphotoxin, macbecin II, macrophage inflammatory protein, mannomustine, maytansine, mechlorethamine hydrochloride, medroxyprogesterone, megestrol acetate, melengestrol acetate, melphalan, menogaril, mepitiostane, mercaptopurine, mesna, methotrexate, methotrexate derivatives meturedepa, monomethyl auristatin E, miltefosine, mitobronitol, mitoguazone, mitolactol, mitomycin, mitotane, mitoxantrone, mitozolamide, mopidamol, morpholinodoxorubicin, mutated tumor-specific antigens, mycophenolic acid, N-(phosphonoacetyl)-L-aspartate, N,N-dibenzyldaunorubicin, nerve growth factor, nilotinib, nilutamide, nimustine, nitracine, nogalamycin, nonautologous cells or tissues, oblimersen, oestrogen, OGX-011, olivomycins, osteonectin, ONYX-015, oxaliplatin, paclitaxel, paclitaxel derivative, 1-(2-chloroethyl)-3-(2,6-dioxo-3-piperidyl)-1-nitrosourea, pegaspargase, pentostatin, peplomycin, perfosfamide, phenesterin, plicamycin, piperazine derivatives, piperazinedione, pipobroman, piposulfan, pirarubicin, piritrexim, piroxantrone, platelet derived growth factor, plasminogen kringle 5, plicamycin, podophyllotoxin, polyestradiol phosphate, polyglutamate camptothecin porfimer sodium, porfiromycin, prednimustine, prednisone, procabazine, procaine, propagermanium, propranolol, *Pseudomonas* exotoxin, polysaccharide-K, pteropterin, puromycin, pyrazofurin, pyrazoloacridine, pyrazoloimidazole, raltitrexed, ranimustine, razoxane, recombinant human granulocyte-monocyte-colony-stimulating factor, retinoid, rhizoxin, ricin A, rituximab, roquinimex, serine protease inhibitors, sorafenib tosylate, spirogermanium, spiromustine, streptonigrin, streptozocin, sunitinib malate, tamoxifen citrate, tegafur-uracil, temozolomide, teniposide, tenuazonic acid, teroxirone, testolactone, tetracaine, tetraplatin, thalidomide, thiocolchicine, thioguanine, thiopurine, thiotepa, trabectedin, thrombospondin-I derived peptides, tissue plasminogen activator, topotecan, toremifene, trastuzumab, tretinoin, triazinate, triaziquone, triethylenemelamine, trilostane, trimetrexate glucuronate, triptorelin, S-trityl-L-cysteine, trofosfamide, tubercidin, tumor necrosis factor-like cytokines, recombinant tumor necrosis factor family proteins, ubenimex, uracil mustard, uracil, urethan, vandetanib, VEGF antisense oligonucleotide, vinblastine, vinblastine sulfate, vincristine, vincristine sulfate, vindesine, vinorelbine, yoshi-864, zinostatin, zorubicin.

In another embodiment, one or more immunoconjugates of the present application can be administered in combination with one or more of the following cancer therapies or categories of therapeutic agents, including without limitation, radiation, surgery, gene therapy, agents to control of side effects (eg. antihistaminic agents, anti-nausea agents), cancer vaccines, inhibitors of angiogenesis, immune modulators, anti-inflammatories, immunosuppressants, agents that increase expression of antigen, other agents associated with cancer therapy chemotherapeutic agents (i.e. immunotherapeutics, photosensitizers, tk inhibitors, antibiotics, antimetabolites, agents that acts to disrupt DNA. agents that acts to disrupt tubulin, alkylating agents, topoisomerase I inhibitors topoisomerase II inhibitors, cytokines and growth factors, hormonal therapies, vinca alkyloids, plant alkaloids, antimitotic agents).

Indeed, administration of an effective amount of an immunoconjugate to a patient in need of such treatment may result in reduced doses of another cancer therapeutic having clinically significant efficacy. Such efficacy of the reduced dose of the other cancer therapeutic may not be observed absent administration with an immunoconjugate. Accordingly, the present application provides methods for treating a tumor or cancer comprising administering a reduced dose of one or more other cancer therapeutics.

Moreover, combination therapy comprising an immunoconjugate to a patient in need of such treatment may permit relatively short treatment times when compared to the duration or number of cycles of standard treatment regimens. Accordingly, the present application provides methods for treating a tumor or cancer comprising administering one or more other cancer therapeutics for relatively short duration and/or in fewer treatment cycles.

Thus, in accordance with the present application, combination therapies comprising an immunoconjugate and another cancer therapeutic may reduce toxicity (i.e., side effects) of the overall cancer treatment. For example, reduced toxicity, when compared to a monotherapy or another combination therapy, may be observed when delivering a reduced dose of immunoconjugate and/or other cancer therapeutic, and/or when reducing the duration of a cycle (i.e., the period of a single administration or the period of a series of such administrations), and/or when reducing the number of cycles.

Accordingly, the present application provides a pharmaceutical composition comprising an immunoconjugate and one or more additional anticancer therapeutic, optionally in a pharmaceutically acceptable carrier.

The present application also provides a kit comprising an effective amount of an immunoconjugate, optionally, in combination with one or more other cancer therapeutic, together with instructions for the use thereof to treat cancer. The kit can also include ancillary agents. For example, the kits can include instruments for injecting the immunoconjugate into a subject, such as a syringe; vessels for storing or transporting the immunoconjugate; and/or pharmaceutically acceptable excipients, carriers, buffers or stabilizers.

As stated above, combination therapy with an immunoconjugate may sensitize the cancer or tumor to administration of an additional cancer therapeutic. Accordingly, the present application contemplates combination therapies for preventing, treating, and/or preventing recurrence of cancer comprising administering an effective amount of an immunoconjugate prior to, subsequently, or concurrently with a reduced dose of a cancer therapeutic. For example, initial treatment with an immunoconjugate may increase the sensitivity of a cancer or tumor to subsequent challenge with a dose of cancer therapeutic. This dose is near, or below, the low range of standard dosages when the cancer therapeutic is administered alone, or in the absence of an immunoconjugate. When concurrently administered, the immunoconjugate may be administered separately from the cancer therapeutic, and optionally, via a different mode of administration.

In an alternate embodiment, administration of the additional cancer therapeutic may sensitize the cancer or tumor to the immunoconjugate or binding protein. In such an embodiment, the additional cancer therapeutic may be given prior to administration of the immunoconjugate or binding protein.

In one embodiment, the additional cancer therapeutic comprises cisplatin, e.g., PLATINOL or PLATINOL-AQ (Bristol Myers), at a dose ranging from approximately 5 to 10, 11 to 20, 21 to 40, or 41 to 75 mg/m2/cycle.

In another embodiment, the additional cancer therapeutic comprises carboplatin, e.g., PARAPLATIN (Bristol Myers), at a dose ranging from approximately 2 to 3, 4 to 8, 9 to 16, 17 to 35, or 36 to 75 mg/m2/cycle.

In another embodiment, the additional cancer therapeutic comprises cyclophosphamide, e.g., CYTOXAN (Bristol Myers Squibb), at a dose ranging from approximately 0.25 to 0.5, 0.6 to 0.9, 1 to 2, 3 to 5, 6 to 10, 11 to 20, or 21 to 40 mg/kg/cycle.

In another embodiment, the additional cancer therapeutic comprises cytarabine, e.g., CYTOSAR-U (Pharmacia & Upjohn), at a dose ranging from approximately 0.5 to 1, 2 to 4, 5 to 10, 11 to 25, 26 to 50, or 51 to 100 mg/m2/cycle. In another embodiment, the additional cancer therapeutic comprises cytarabine liposome, e.g., DEPOCYT (Chiron Corp.), at a dose ranging from approximately 5 to 50 mg/m2/cycle.

In another embodiment, the additional cancer therapeutic comprises dacarbazine, e.g., DTIC or DTICDOME (Bayer Corp.), at a dose ranging from approximately 15 to 250 mg/m2/cycle or ranging from approximately 0.2 to 2 mg/kg/cycle.

In another embodiment, the additional cancer therapeutic comprises topotecan, e.g., HYCAMTIN (SmithKline Beecham), at a dose ranging from approximately 0.1 to 0.2, 0.3 to 0.4, 0.5 to 0.8, or 0.9 to 1.5 mg/m2/Cycle.

In another embodiment, the additional cancer therapeutic comprises irinotecan, e.g., CAMPTOSAR (Pharmacia & Upjohn), at a dose ranging from approximately 5 to 9, 10 to 25, or 26 to 50 mg/m2/cycle.

In another embodiment, the additional cancer therapeutic comprises fludarabine, e.g., FLUDARA (Berlex Laboratories), at a dose ranging from approximately 2.5 to 5, 6 to 10, 11 to 15, or 16 to 25 mg/m2/cycle.

In another embodiment, the additional cancer therapeutic comprises cytosine arabinoside (Ara-C) at a dose ranging from approximately 200 to 2000 mg/m2/cycle, 300 to 1000 mg/m2/cycle, 400 to 800 mg/m2/cycle, or 500 to 700 mg/m2/cycle.

In another embodiment, the additional cancer therapeutic comprises docetaxel, e.g., TAXOTERE (Rhone Poulenc Rorer) at a dose ranging from approximately 6 to 10, 11 to 30, or 31 to 60 mg/m2/cycle.

In another embodiment, the additional cancer therapeutic comprises paclitaxel, e.g., TAXOL (Bristol Myers Squibb), at a dose ranging from approximately 10 to 20, 21 to 40, 41 to 70, or 71 to 135 mg/kg/cycle.

In another embodiment, the additional cancer therapeutic comprises 5 fluorouracil at a dose ranging from approximately 0.5 to 5 mg/kg/cycle, 1 to 4 mg/kg/cycle, or 2-3 mg/kg/cycle.

In another embodiment, the additional cancer therapeutic comprises doxorubicin, e.g., ADRIAMYCIN (Pharmacia & Upjohn), DOXIL (Alza), RUBEX (Bristol Myers Squibb), at a dose ranging from approximately 2 to 4, 5 to 8, 9 to 15, 16 to 30, or 31 to 60 mg/kg/cycle.

In another embodiment, the additional cancer therapeutic comprises etoposide, e.g., VEPESID (Pharmacia & Upjohn), at a dose ranging from approximately 3.5 to 7, 8 to 15, 16 to 25, or 26 to 50 mg/m2/cycle.

In another embodiment, the additional cancer therapeutic comprises vinblastine, e.g., VELBAN (Eli Lilly), at a dose ranging from approximately 0.3 to 0.5, 0.6 to 0.9, 1 to 2, or 3 to 3.6 mg/m2/cycle.

In another embodiment, the additional cancer therapeutic comprises vincristine, e.g., ONCOVIN (Eli Lilly), at a dose ranging from approximately 0.1, 0.2, 0.3, 0.4, 0.5, 0.6 or 0.7 mg/m2/cycle.

In another embodiment, the additional cancer therapeutic comprises methotrexate at a dose ranging from approximately 0.2 to 0.9, 1 to 5, 6 to 10, or 11 to 20 mg/m2/cycle.

Combination therapy may thus increase the sensitivity of the cancer or tumor to the administered immunoconjugate and/or additional cancer therapeutic. In this manner, shorter treatment cycles may be possible thereby reducing toxic events. The cycle duration may vary according to the specific cancer therapeutic in use. The present application also contemplates continuous or discontinuous administration, or daily doses divided into several partial administrations. An appropriate cycle duration for a specific cancer therapeutic will be appreciated by the skilled artisan, and the present application contemplates the continued assessment of optimal treatment schedules for each cancer therapeutic. Specific guidelines for the skilled artisan are known in the art. See, e.g., Therasse et al., 2000, "New guidelines to evaluate the response to treatment in solid tumors. European Organization for Research and Treatment of Cancer, National Cancer Institute of the United States, National Cancer Institute of Canada," J Natl Cancer Inst. February 2; 92(3):205-16.

It is contemplated that the immunoconjugate may be administered by any suitable method such as injection, oral administration, inhalation, transdermal or intratumorally, whereas any other cancer therapeutic may be delivered to the patient by the same or another mode of administration. Additionally, where multiple cancer therapeutics are intended to be delivered to a patient, the immunoconjugate and one or more of the other cancer therapeutics may be delivered by one method, whereas other cancer therapeutics may be delivered by another mode of administration.

(G) Diagnostic Methods and Agents Using the Binding Proteins and Immunotoxins The binding proteins of the present application bind selectively to the surface of cancer cells, and not significantly to normal cells. Therefore the binding proteins can be used in the diagnosis of cancer.

Accordingly, the present application includes diagnostic methods, agents, and kits that can be used by themselves or prior to, during or subsequent to the therapeutic method of the present application in order to determine whether or not cancer cells are present.

In one embodiment, the present application provides a method of detecting or monitoring cancer in a subject comprising the steps of
(1) contacting a test sample taken from said subject with the binding proteins or immunoconjugates of the present application and that binds specifically to an antigen on the cancer cell to produce a binding protein-antigen complex;
(2) measuring the amount of binding protein-antigen complex in the test sample; and
(3) comparing the amount of binding protein-antigen complex in the test sample to a control.

In one embodiment, the antigen is an IkBβ protein, such as IkBβ1, IkBβ2 and/or a cancer-associated variant of IkBβ.

The present application further includes a kit for diagnosing cancer comprising any one of the binding proteins or immunoconjugates of the present application and instructions for the use thereof to diagnose the cancer. The kit can also include ancillary agents. For example, the kits can include additional reagents, such as agents to detect the binding proteins or immunoconjugates of the present application directly or indirectly; vessels for storing or transporting the binding proteins or immunoconjugates; and/or other buffers or stabilizers.

For use in the diagnostic applications, the binding proteins of the present application, preferably antibodies or antibody fragments, may be labeled with a detectable marker such as a radio-opaque or radioisotope, such as $^3$H, $^{14}$C, $^{32}$P, $^{35}$S, $^{123}$I, $^{125}$I, $^{131}$I; a fluorescent (fluorophore) or chemiluminescent (chromophore) compound, such as fluorescein isothiocyanate, rhodamine or luciferin; an enzyme, such as alkaline phosphatase, betagalactosidase or horseradish peroxidase; an imaging agent; or a metal ion. As described above, methods of attaching a label to a binding protein, such as an antibody or antibody fragment, are known in the art.

Another aspect of the present application is a method of detecting or monitoring cancer in a subject comprising the steps of
(1) measuring the amount of antibodies of the present application in a test sample taken from said subject; and
(2) comparing the amount of antibodies of the present application in the test sample to a control.

In one embodiment, the amount of antibodies of the present application is measured by measuring the amount of antibodies of the present application in the test sample, for example by ELISA. In another embodiment, the amount of antibodies of the present application is measured by measuring the expression levels of nucleic acids encoding the antibodies of the present application in the test sample, for example by RT-PCR.

(H) Pharmaceutical Compositions, Methods and Uses of the Antigen

The inventors have identified an antigen present on the surface of cancer cells and not significantly expressed on the surface of normal cells. Accordingly, this antigen can be used in therapies to treat and prevent cancer. As mentioned above, IkBβ proteins, such as IkBβ1 and IkBβ2, do not normally contain transmembrane domains, and are not normally expressed on the surface of cells. Thus, the antigens of the present application can be used as targets in therapies to treat and prevent cancer. For example, the cancer-associated variant of IkBβ or parts thereof (such as the extracellular domain) can be used to elicit an immune response in vivo. In addition, the present application includes using the antigens of the present application to detect or monitor cancer.

(i) Pharmaceutical Compositions

One embodiment of the present application is a pharmaceutical composition comprising an effective amount of the antigen of the present application in admixture with a suitable diluent or carrier. Another embodiment of the present application is a pharmaceutical composition comprising an effective amount of an isolated nucleic acid encoding the antigen of the present application in admixture with a suitable diluent or carrier. A further aspect of the present application is a pharmaceutical composition comprising an effective amount of a recombinant expression comprising a nucleic acid sequence encoding the antigen of the present application in admixture with a suitable diluent or carrier. In one embodiment, the antigen of the present application is a cancer-associated variant of IkBβ.

For example, the pharmaceutical compositions of the present application can be used to treat or prevent cancer. In addition, the pharmaceutical compositions can be used to elicit an immune response in a subject against cancer cells expressing the antigen of the present application on the surface of the cells.

The pharmaceutical composition can be prepared and administered as discussed above. The pharmaceutical composition can be used in combination with other anticancer therapeutic agents as discussed above.

Immunogenicity can be significantly improved if the immunizing agents (i.e. antigen of the present application or a variant thereof, and/or nucleic acid sequences coding thereof, and/or recombinant expression vectors) and/or composition is, regardless of administration format, co-immunized with an adjuvant. Commonly, adjuvants are used as a 0.05 to 1.0 percent solution in phosphate buffered saline. Adjuvants enhance the immunogenicity of an immunogen but are not necessarily immunogenic in of themselves. Adjuvants may act by retaining the immunogen locally near the site of administration to produce a depot effect facilitating a slow, sustained release of immunogen to cells of the immune system. Adjuvants can also attract cells of the immune system to an immunogen depot and stimulate such cells to elicit immune response. As such, embodiments of this present application encompass pharmaceutical compositions further comprising adjuvants.

Adjuvants have been used for many years to improve the host immune responses to, for example, vaccines. Intrinsic adjuvants (such as lipopolysaccharides) normally are the components of killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established. Notwithstanding, it does have limitations. For example, alum is ineffective for influenza vaccination and inconsistently elicits a cell mediated immune response with other immunogens. The antibodies elicited by alumadj wanted antigens are mainly of the IgG1 isotype in the mouse, which may not be optimal for protection by some vaccinal agents.

A wide range of extrinsic adjuvants can provoke potent immune responses to immunogens. These include saponins complexed to membrane protein antigens (immune stimulating complexes), pluronic polymers with mineral oil, killed mycobacteria and mineral oil, Freund's complete adjuvant, bacterial products such as muramyl dipeptide (MDP) and lipopolysaccharide (LPS), as well as lipid A, and lipo.

In one aspect of this present application, adjuvants useful in any of the embodiments of the present application described herein are as follows. Adjuvants for parenteral immunization include aluminum compounds (such as aluminum hydroxide, aluminum phosphate, and aluminum hydroxy phosphate). The antigen can be precipitated with, or adsorbed onto, the aluminum compound according to standard protocols. Other adjuvants such as RIBI (ImmunoChem, Hamilton, Mont.) can also be used in parenteral administration.

Adjuvants for mucosal immunization include bacterial toxins (e.g., the cholera toxin (CT), the *E. coli* heat-labile toxin (LT), the *Clostridium difficile* toxin A and the pertussis toxin (PT), or combinations, subunits, toxoids, or mutants thereof). For example, a purified preparation of native cholera toxin subunit B (CTB) can be of use. Fragments, homologs, derivatives, and fusion to any of these toxins are also suitable, provided that they retain adjuvant activity. Preferably, a mutant having reduced toxicity is used. Suitable mutants have been described (e.g., in WO 95/17211 (Arg-7-Lys CT mutant), WO 96/6627 (Arg-192-Gly LT mutant), and WO 95/34323 (Arg-9-Lys and Glu-129-Gly PT mutant)). Additional LT mutants that can be used in the methods and compositions of the present application include, for example Ser-63-Lys, Ala-69-Gly, Glu-110-Asp, and Glu-112-Asp mutants. Other adjuvants (such as a bacterial mono-phosphoryl lipid A (MPLA) of various sources (e.g., *E. coli, Salmonella minnesota, Salmonella typhimurium,* or *Shigella flexneri*, saponins, or polylactide glycolide (PLGA) microspheres) can also be used in mucosal administration.

Adjuvants useful for both mucosal and parenteral immunization include polyphosphazene (for example, WO 95/2415), DC-chol (3 b-(N—(N',N'-dimethyl aminomethane)-carbamoyl)cholesterol (for example, U.S. Pat. No. 5,283,185 and WO 96/14831) and QS-21 (for example, WO 88/9336).

A subject may be immunized with a pharmaceutical composition comprising the antigen of the present application, an isolated nucleic acid sequence encoding thereof and/or a recombinant expression vectors by any conventional route as is known to one skilled in the art. This may include, for example, immunization via a mucosal (e.g., ocular, intranasal, oral, gastric, pulmonary, intestinal, rectal, vaginal, or urinary tract) surface, via the parenteral (e.g., subcutaneous, intradermal, intramuscular, intravenous, or intraperitoneal) route or intranodally. Preferred routes depend upon the choice of the immunogen as will be apparent to one skilled in the art. The administration can be achieved in a single dose or repeated at intervals. The appropriate dosage depends on various parameters understood by skilled artisans such as the immunogen itself (i.e. peptide vs. nucleic acid (and more specifically type thereof)), the route of administration and the condition of the animal to be vaccinated (weight, age and the like).

The present application also provides kits comprising an effective amount of the antigen of the present application, optionally, in combination with one or more other cancer therapeutic, together with instructions for the use thereof. The kit can also include ancillary agents. For example, the kits can include instruments for injecting the antigen of the present application into a subject, such as a syringe; vessels for storing or transporting the antigen of the present application; adjuvants; and/or pharmaceutically acceptable excipients, carriers, buffers or stabilizers. In one embodiment, the antigen of the present application is a cancer-associated variant of IkBβ.

(ii) Therapeutic Methods

As mentioned above, the antigen of the present application is present on cancer cells, but not significantly on normal cells. Thus, the antigen of the present application or parts thereof (such as the extracellular domain) can be used in therapeutic methods to prevent or treat cancer. In addition, the antigen of the present application or parts thereof (such as the extracellular domain) can be used to elicit an immune response in a subject, for example in a vaccine.

One embodiment of the present application is the use of the antigen of the present application in the manufacture of a medicament to treat or prevent cancer. Another embodiment of the present application is the use of the antigen of the present application in the manufacture of a medicament to elicit an immune response in a subject.

The present application also includes the use of an isolated nucleic acid sequence encoding the antigen of the present application in the manufacture of a medicament to treat or prevent cancer. In addition, the present application includes the use of an isolated nucleic acid sequence encoding the antigen of the present application in the manufacture of a medicament to elicit an immune response in a subject.

A further embodiment of the present application is the use of the recombinant expression vector comprising an isolated nucleic acid sequence encoding the antigen of the present application in the manufacture of a medicament to treat or prevent cancer. Also, the present application includes the use of the recombinant expression vector comprising an isolated nucleic acid sequence encoding the antigen of the present application in the manufacture of a medicament to elicit an immune response in a subject.

An additional embodiment of the present application is a method of treating or preventing cancer in a subject having or suspected of having cancer comprising administering to said subject an effective amount of the antigen of the present application. In addition, the present application includes a method of treating or preventing cancer in a subject having or suspected of having cancer comprising administering to said subject an effective amount of an isolated nucleic acid sequence encoding the antigen of the present application. Further, the present application includes a method of treating or preventing cancer in a subject having or suspected of having cancer comprising administering to said subject an effective amount of a recombinant expression vector comprising an isolated nucleic acid sequence encoding the antigen of the present application.

Another embodiment of the present application is a method of inducing an immune response in a subject against cancer comprising administering to said subject an effective amount of the antigen of the present application. In addition, the present application includes a method of inducing an immune response in a subject against cancer comprising administering to said subject an effective amount of an isolated nucleic acid sequence encoding the antigen of the present application. Further, the present application includes a method of inducing an immune response in a subject against cancer comprising administering to said subject an effective amount of an recombinant expression vector comprising an isolated nucleic acid sequence encoding the antigen of the present application.

In one embodiment, the antigen of the present application is a cancer-associated variant of IkBβ.

(iii) Diagnostic Methods

The antigen of the present application is expressed on cancer cells and is not significantly expressed on normal cells, thus the detection of the antigen of the present application on the surface of cells can be used as a diagnostic method for cancer. Further, the detection of RNA expression of the cancer-associated variant of IkBβ can be used as a diagnostic method for cancer.

One embodiment of the present application is a method of detecting or monitoring cancer in a subject, comprising detecting the antigen of the present application on a cell in the sample, wherein cancer is indicated, if the antigen of the present application is detected on the cell.

A number of techniques can be used to detect the antigen of the present application on a cell. For example, the binding proteins of the present application can be used in immunoassays to detect cell surface expression of the antigen of the present application. A person skilled in the art will appreciate that a number of techniques can be used to detect and/or quantify cell surface expression of the antigen of the present application, including Western blots, immunoprecipitation followed by SDS-PAGE, immunocytochemistry, FACS, protein arrays, and the like.

Another aspect of the present application is a method of detecting or monitoring cancer in a subject, comprising detecting the expression of a cancer-associated variant of IkBβ by the cell in the sample, wherein cancer is indicated, if expression of the cancer-associated variant of IkBβ is detected. In one example, an RNA expression product encoding the cancer-associated variant of IkBβ is used to detect the expression of the cancer-associated variant of IkBβ in the cell. One skilled in the art will appreciate that the RNA expression product can be detected or quantified by detecting mRNA encoding the cancer-associated variant of IkBβ, or oligonucleotides, cDNA, DNA, RNA, PCR products, synthetic DNA, synthetic RNA, or other combinations of naturally occurring or modified nucleotides which specifically and/or selectively hybridize to the mRNA encoding the cancer-associated variant of IkBβ.

A number of methods can be used to detect and/or quantify RNA expression of the cancer-associated variant of IkBβ in a cell including RT-PCR, nuclease protection assays, such as ribonuclease protection assays and SI nuclease assays, and Northern blots and the like.

Genomic mutations can also be detected following the isolation of the mRNA coding for the antigen of the present application and/or for the cancer-associated variant of IkBβ using methods known to the art.

In one embodiment, the cancer-associated variant of IkBβ3 is a variant of IkBβ2.

(I) Other Methods

IkBβ an inhibitory regulator of NFk-B. As such, IkBβ plays a significant role in the regulation of cell growth, apoptosis, and response to inflammation. IkBβ is not normally found on the surface of cells. Normally, non-phosphorylated IkBβ binds to NFk-B in the cytoplasm of cells and prevents NFk-B from entering the nucleus of the cell. In contrast, the cancer-associated variant of IkBβ has at least one transmembrane domain and is present on the surface of cancer cells. Thus, without being limited to theory, the cancer-associated variant of IkBβ could be disrupting the normal role of IkBβ in cancer cells. Thus, the present application includes a method of treating or preventing cancer in a subject by modulating the activity of the cancer-associated variant of IkBβ in a cancer cell or restoring or replacing the activity of IkBβ in a cancer cell.

In one embodiment of the present application, the method of treating or preventing cancer in a subject comprises preventing or decreasing the expression or function of the cancer-associated variant IkBβ or restoring or replacing the normal function of IkBβ in a cancer cell.

Standard techniques can be used to prevent or decrease the expression of the cancer-associated variant of IkBβ in a cell including using antisense, triple helix, or ribozyme molecules reactive to the transcripts of the cancer-associated variant of IKBβ gene.

For example, standard techniques can be utilized for the production of antisense nucleic acid molecules, i.e., molecules which are complementary to a sense nucleic acid encoding a polypeptide of interest, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire coding strand, or to only a portion thereof, e.g., all or part of the protein coding region (or open reading frame). An antisense nucleic acid molecule can be antisense to all or part of a non-coding region of the coding strand of a nucleotide sequence encoding a polypeptide of interest. The non-coding regions ("5' and 3' untranslated regions") are the 5' and 3' sequences that flank the coding region and are not translated into amino acids.

An antisense oligonucleotide can be, for example, about 5, 10, 15, 20, 25, 30, 35, 40, 45 or 50 nucleotides or more in length. An antisense nucleic acid of the present application can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6- diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Antisense nucleic acid molecules administered to a subject or generated in situ such that they hybridize with or bind to cellular mRNA encoding the polypeptide of interest to thereby inhibit expression, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the present application includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell, e.g., a T cell or brain cell, e.g., by linking the antisense nucleic acid molecules to peptides or antibodies which bind to cell surface receptors or antigens. The antisense nucleic acid molecules can also be delivered to cells using vectors, e.g., gene therapy vectors, described below. To achieve sufficient intracellular concentrations of the antisense molecules, vector constructs in which the antisense nucleic acid molecule is placed under the control of a strong pol II or pol III promoter are preferred.

An antisense nucleic acid molecule of interest can be an a-anomeric nucleic acid molecule. An a-anomeric nucleic acid molecule forms specific double-stranded hybrids with complementary RNA in which, contrary to the usual a-units, the strands run parallel to each other (Gaultier et al., 1987, Nucleic Acids Res. 15:6625-6641). The antisense nucleic acid molecule can also comprise a 2'-o-methylribo-nucleotide (Inoue et al., 1987, Nucleic Acids Res. 15:6131-6148) or a chimeric RNA-DNA analogue (Inoue et al., 1987, FEBS Lett. 215:327-330).

Ribozymes are catalytic RNA molecules with ribonuclease activity that are capable of cleaving a single-stranded nucleic acid, such as an mRNA, to which they have a complementary region, and can also be generated using standard techniques. Thus, ribozymes (e.g., hammerhead ribozymes (described in Haselhoff and Gerlach, 1988, Nature 334:585-591)) can be used to catalytically cleave mRNA transcripts to thereby inhibit translation of the protein encoded by the mRNA. A ribozyme having specificity for a nucleic acid molecule encoding a polypeptide of interest can be designed based upon the nucleotide sequence of a cDNA encoding a cancer-associated variant of IkBβ. For example, a derivative of a Tetrahymena L-19 IVS RNA can be constructed in which the nucleotide sequence of the active site is complementary to the nucleotide sequence to be cleaved in a Cech et al. U.S. Pat. No. 4,987,071; and Cech et al. U.S. Pat. No. 5,116,742. Alternatively, an mRNA encoding a polypeptide of interest can be used to select a catalytic RNA having a specific ribonuclease activity from a pool of RNA molecules. See, e.g., Bartel and Szostak, 1993, Science 261:1411-1418.

Triple helical structures can also be generated using well known techniques. For example, expression of a polypeptide of interest can be inhibited by targeting nucleotide sequences complementary to the regulatory region of the gene encoding the polypeptide (e.g., the promoter and/or enhancer) to form triple helical structures that prevent transcription of the gene in target cells. See generally Helene, 1991, Anticancer Drug Des. 6(6):569-84; Helene, 1992, Ann. N.Y. Acad. Sci. 660: 27-36; and Maher, 1992, Bioassays 14(12):807-15.

In various embodiments, nucleic acid compositions can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al., 1996, Bioorganic & Medicinal Chemistry 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al., 1996, supra; Perry-O'Keefe et al., 1996, Proc. Natl. Acad. Sci. USA 93: 14670-675.

PNAs can, for example, be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup, 1996, supra, and Finn et al, 1996, Nucleic Acids Res. 24(17):3357-63. For example, a DNA chain can be synthesized on a support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al, 1989, Nucleic Acids Res. 17:5973-88). PNA monomers are then coupled in a stepwise manner to produce a chimeric molecule with a 5'PNA segment and a 3' DNA segment (Finn et al, 1996, Nucleic Acids Res. 24(17):3357-63). Alternatively, chimeric molecules can be synthesized with a 5' DNA segment and a 3' PNA segment (Peterser et al, 1975, Bioorganic Med. Chem. Lett. 5:1119-11124).

In other embodiments, the oligonucleotide may include other appended groups such as peptides (e.g., for targeting host cell receptors in vivo), or agents facilitating transport across the cell membrane (see, e.g., Letsinger et al, 1989, Proc. Natl. Acad. Sci. USA 86:6553-6556; Lemaitre et al, 1987, Proc. Natl. Acad. Sci. USA 84:648-652; International Publication No. WO 88/09810) or the blood-brain barrier (see, e.g., International Publication No. WO 89/10134). In addition, oligonucleotides can be modified with hybridization-triggered cleavage agents (see, e.g., Krol et al, 1988, Bio/Techniques 6:958-976) or intercalating agents (see, e.g., Zon, 1988, Pharm. Res. 5:539-549). To this end, the oligonucleotide may be conjugated to another molecule, e.g., a peptide, hybridization triggered cross-linking agent, transport agent, hybridization-triggered cleavage agent, etc.

Another aspect of the present application is a method of treating or preventing cancer in a subject comprising restoring or replacing the expression or function of IkBβ. In one embodiment, this is done in combination with the method of treating or preventing cancer in a subject comprising preventing or decreasing the expression or function of the cancer-associated variant IkBβ.

Another aspect of the present application is a method to identify compounds that are able to modulate the expression or activity of the cancer-associated variant of IkBβ, which can be used to prevent or treat cancer. In one embodiment of the present application, the method for identifying a compound for ability to prevent or treat cancer comprises the steps:

(a) contacting a cell expressing a cancer-associated variant of IkBβ with a test compound; and (b) determining the expression or function of the cancer-associated variant of IkBβ(3; and (c) comparing the expression or function of the cancer-associated variant of IkBβ to a control, wherein a decrease in expression or function of the cancer-associated variant of IkBβ as compared to the control is indicative of a compound useful to prevent or treat cancer.

Another aspect of the present application is the preparation of recombinant form of the antigen of the application and/or of similarly modified other IkB proteins or fragment thereof or of corresponding nucleic acid sequences for the purpose of detecting the presence of transmembrane forms of IkB proteins and/or of the antigen of the present application. The detection can consist of detecting the protein, the gene and/or the mRNA coding for a modified IkB protein or the antigen of the application. The recombinant forms can be used to prepare antibodies or to detect existing antibodies in the circulation of a patient or subject.

The above disclosure generally describes the present application. A more complete understanding can be obtained by reference to the following specific examples. These examples are described solely for the purpose of illustration and are not intended to limit the scope of the present application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present application:

EXAMPLES

Example 1

Generation of VB1-204 Monoclonal Antibody and Sequencing

VB1-204, an IgM MAb, was generated from the lymph nodes of a breast cancer patient.

Messenger RNA was isolated from hybridoma cells and first strand complement DNA (cDNA) was synthesized using the reverse transcriptase enzyme. The cDNA was then used to isolate the heavy and light chain antibody fragments by Polymerase Chain Reaction (PCR). PCR primers of the consensus framework regions of the $V_H$ and lambda were used to amplify the heavy and light chain, respectively.

```
5' V_H Primers
                                         (SEQ ID NO: 12)
1  5' CCA GCC ATG GCG CAG RTG CAG CTG GTG CAR

TCT G (SEQ ID NO: 13)
2  5' CCA GCC ATG GCG SAG GTC CAG CTG GTR CAG

TCT GG (SEQ ID NO: 14)
3  5' CCA GCC ATG GCG CAG RTC ACC TTG AAG GAG

TCT GG (SEQ ID NO: 15)
4  5' CCA GCC ATG GCG SAG GTG CAG CTG GTG GAG

TCT GG (SEQ ID NO: 16)
5  5' CCA GCC ATG GCG GAG GTG CAG CTG GTG GAG

WCY GG (SEQ ID NO: 17)
6  5' CCA GCC ATG GCG CAG GTG CAG CTA CAG CAG

TGG GG (SEQ ID NO: 18)
7  5' CCA GCC ATG GCG CAG STG CAG CTG CAG GAG

TCS GG (SEQ ID 19)
8  5' CCA GCC ATG GCG CAG GAR GTG CAG CTG GTG

CAG TCT GG (SEQ ID NO: 20)
9  5' CCA GCC ATG GCG CAG CAG GTA CAG CTG CAG

CAG TCA GG

3' primer:
                                         (SEQ ID NO: 21)
1  5' CCA GGA GAA AGT GAT GGA GTC GGG AAG GAA

GTC CTG TGC GAG (SEQ ID NO: 22)
2  5' CGA CGG GGA ATT CTC ACA GGA GAC GAG GGG

GAA AAG GGT TGG

Lambda Primers:
5' primers:
                                         (SEQ ID NO: 23)
1  5' ATG GCC TGS WCY CCT CTC YTC CTC AYC (SEQ ID NO: 24)
2  5' ATG GCC TGG GCT CTS YTB YTS YTC ASC (SEQ ID NO: 25)
3  5' ATG GCM TGG AYC SYT CTC YTC CTC GGC 3' primer:
                                         (SEQ ID NO: 26)
1  CAC TAG TGT GGC CTT GTT GGC TTG GAC CTC CTC

AGA GGA GGG
```

Note: In order to isolate the chains, a mixture of 5' primers are used with mixed bases for certain consensus sequences: R=A+G, S=C+G, W=A+T, Y=C+T, D=A+T, H=A+C, K=T+G, B=T+C+G, M=A+C The PCR reaction included a 50 μL reaction volume containing:

| | |
|---|---|
| 10X PCR buffer | 5 μL |
| 2 mM dNTPs | 5 μL |

-continued

| Primer 5' | 20 pmol |
|---|---|
| Primer 3' | 20 pmol |
| Taq DNA Polymerase | 2.5 U |
| DNA template | 50 ng |

The cycling conditions for PCR were: 94° C. for 1 min., 62° C. for 1 min., and 72° C. for 1 min., for a total of 30 cycles followed by a final extension of 10 min. at 72° C. The $V_H$ domain was obtained using two rounds of 30 cycles with the following primers in the first 30 cycles, 5'$V_H$ primers and 3' primer-1. Then 1 μL of the first PCR reaction was re-amplified using 5' $V_H$ primers and 3' primer-2.

Electrophoresis on a 1% agarose gel was used to separate the amplified PCR products. The bands of interest were excised and purified using a Qiaquick gel extraction kit, cloned into the TOPO pCR 2.1 cloning vector and sequenced using the 373 DNA sequencer. The analysis of the sequence indicated that the subclass for the heavy and light chains is VH3 (FIG. 1A) and VL3 (FIG. 1B), respectively. The light chain and heavy chain variable regions are shown in FIG. 1 (SEQ ID NO: 1-4). The CDR sequences for VB1-204 are shown in Table 1 (SEQ ID NO: 5-10).

Example 2

Antibody Profiling by Measuring Tumor Cell Reactivity

VB1-204 was tested by flow cytometry for tumor cell reactivity representing seven different types of epithelial cancers (FIG. 2) and the results are summarized in Table 2. MF value indicates the mean-fold increase in median fluorescence over the control antibody from two separate experiment. A zero value indicates no reactivity relative to the control antibody. The strongest binding was to CF-Pac-1 and MB-231 cell lines followed closely by A-375. Therefore VB1-204 binds to an antigen localized to the membrane of tumor cells.

Example 3

Antibody Profiling by Comparison of Tumor Versus Normal Tissue Microarrays

VB1-204 was tested and compared to an isotype-control (IgM Myeloma) on a low-density (LD) array of critical normal tissues (Table 3A). Membrane staining of the normal critical tissues was considered minimal with some staining of the membrane of lung, colon and liver tissues. Significant staining was found in the cytoplasm of cells from all normal tissues tested, suggesting binding to an intracellular protein present in normal cells.

Reactivity of VB1-204 was then tested in a high density (HD) formalin-fixed tumor tissue microarray (Table 3B). Unlike normal tissues, VB1-204 reactivity was detected on the membrane liver, colon, lung, pancreas and kidney. The frequency of membrane staining per tissue sample was highest on the colon. Membrane staining was detected on liver, colon, kidney, pancreas and lung with varying incidence, intensity and percentage positive cells.

Example 4

Assessment of VB1-204 Internalization by Confocal Microscopy

Figure 3:
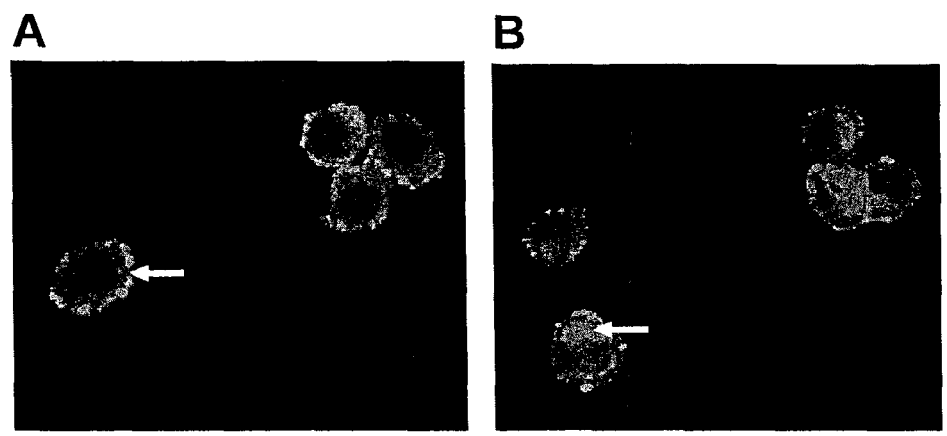
FIG. 3 is an assessment of internalization of VB1-204 by confocal microscopy. A-375 cells were incubated with VB1-204 (100 µg/mL) at 4° C., washed and warmed to 37° C. for 60 min. Cells were fixed, permeabilized and labeled with an anti-human IgM biotinylated antibody followed by an incubation with streptavidin coupled to FITC. A), Fluorescence labeling of A-375 cells after incubation of VB 1-204 at 4° C. for 60 min, displaying circumferential surface distribution of labeling indicated by the white arrow, (60X×3) magnification. B), Following incubation of antibody-bound cells at 37° C. for 60 min, the cells show intracellular staining by the internalized antibody, (60X×3) magnification.

VB1-204 and control antibody (5E9, that is known to be an internalizing antibody into cells) were used to assess VB1-204 for internalization. To determine if the cell-surface bound VB1-204 internalizes, direct visualization of fluorescence distribution and intracellular staining with the aid of laser scanning confocal microscopy was used. A-375 cells were incubated with VB1-204 (100 (μg/mL) or control antibody at 4° C. After washing the cells, half of the sample was warmed at 37° C. for 1 hr, the other half stayed at 4° C. Fixed (with a solution of formaldehyde) and unfixed cells were labeled with fluorescein-labeled second antibody. As seen with the 5E9 positive control antibody, A-375 cells incubated with VB1-204 at 4° C. for 60 min demonstrated circumferential surface distribution of fluorescence label (FIG. 3A). Warming the VB1-204 treated cells to 37° C. revealed a pattern of intracellular staining within 60 minutes, as shown in FIG. 3B, indicating internalization of the VB1-204/antigen complex.

Example 5

Binding Affinity of VB1-204

Flow cytometry was used to assess binding affinity of VB1-204. A range of antibody concentrations were tested against a fixed number of tumor cells (A-375) for 2 hours to obtain a saturation curve. Values and graphical analysis were generated using Sigma Plot (Jandel Scientific, San Rafael, Calif.). The inverse of the determined median fluorescence was plotted as a function of the inverse of antibody concentration to determine $K_D$ by the Lineweaver-Burk method. A straight line was generated and the $K_D$ was calculated from the slope of the curve (FIGS. 4A and 4B). The dissociation constant, $K_D$ value, was determined by the following equation: $1/F=1/Fmax+(K_D/Fmax)$ $(1/IgM)$, where F=background subtracted median fluorescence and Fmax was calculated from the plot. As shown in FIGS. 4A and 4B, the dissociation constant for VB1-204 was calculated to be $5\times10^{-9}$M.

Example 6

Isolation and Identification of Antigen

Tumor cell lines A375 (melanoma), HepG2 (hepatocellular carcinoma), MB 231 (breast carcinoma) CF-PAC-1 and PANC-1 (pancreatic carcinoma) and DU-145 (prostate carcinoma) were used to isolate and identify the membrane associated antigen bound to VB1-204. These cell lines were selected based on the tumor cell profiling by flow cytometery. The cell lines were purchased from ATCC and cultured in accordance with the guidelines of ATCC.
Preliminary Characterization of the Antigen Binding to VB1-204

VB1-204 was used to immunoprecipitate proteins from membrane extracts of tumor cell lines. The purified proteins were then separated on SDS-PAGE gels that were subsequently western blotted using VB1-204. A 65±2 kDa band on was detected on ID-PAGE in addition to a band at ~34 kDa. After reduction of the purified proteins with 2% SDS for up to 60 minutes at 65° C., all the bands collapsed into a single strong band at ~34 kDa seen consistently in all the reactive cell lines. The data from these experiments classified the VB 1-204 antigen as a "blottable" antigen with a N-glycan masked epitope. As can be seen in the FIGS. 5 A and 5B a strong ~34 kDa was observed in all the positive cell lines. The intensity of the band is also reflective of the level of antigen expression in that particular cell line.

Mass Spectral Analysis and Protein Identification.

Figure 6:
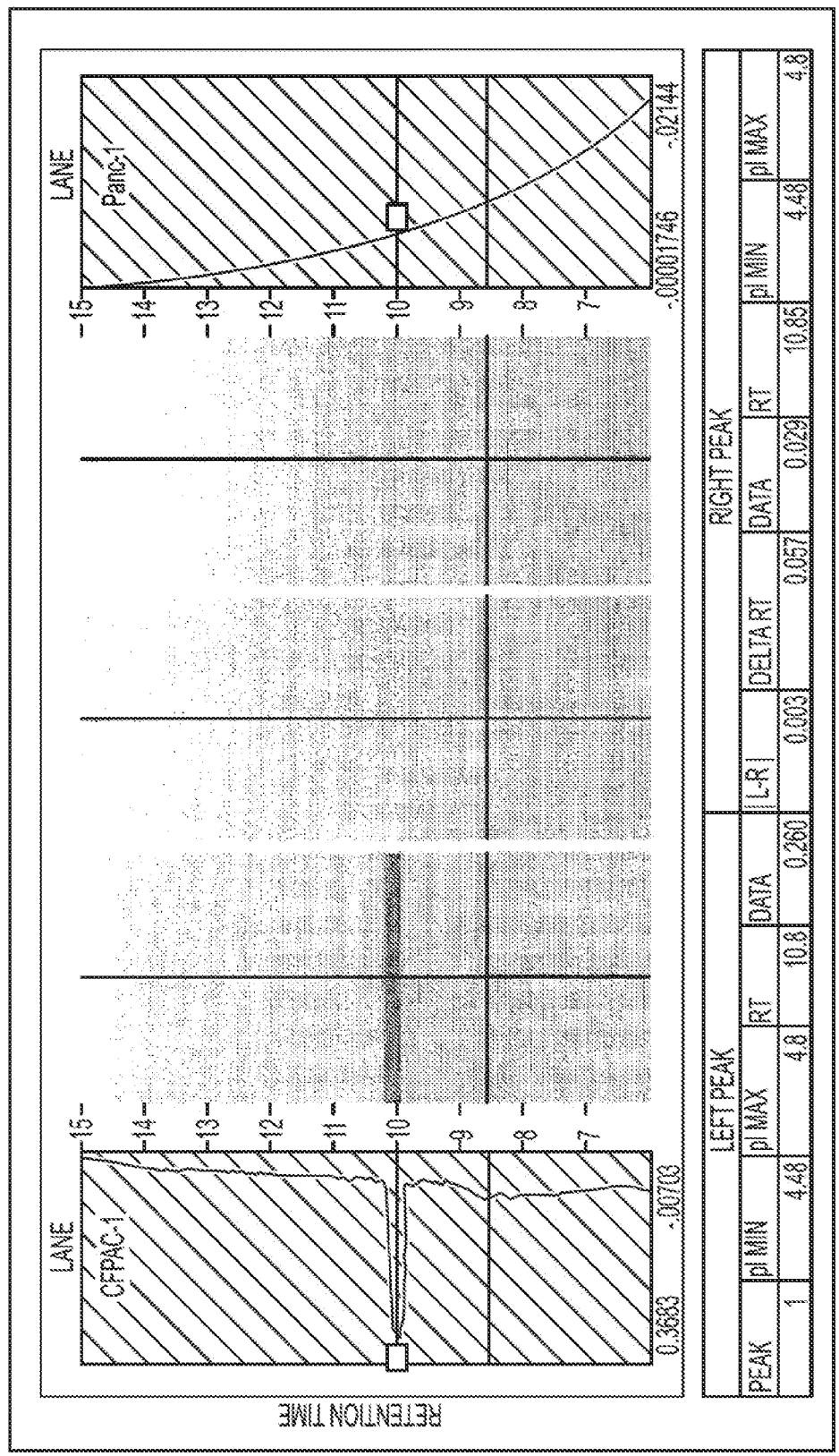
FIG. 6 is an MS analysis of membrane extracts from positive cell line CFPAC-1 compared with negative cell line PANC-1 after immunoprecipitation with VB1-204.

Proteins from the membrane fraction of positive cell line, CFPAC-1 and negative cell line Panc-1 membranes were immunoprecipitated with VB1-204 and separated on the ProteomeLab™ PF-2D system. A single peak eluting at 10.85 minutes was observed in the positive and was absent in the negative cell line as seen in FIG. 6.

Combined results of the MS analysis identified the antigen for VB 1-204 on tumor cell lines CFPAC-1, A375, and MB231 as a variant form of IkBβ2. The peptides initially recovered from these cell lines that were a 100% match to databases sequences are shown mapped to their positions in the protein with the highest probability-based score in FIGS. 7A, 7B and 7C and are included in Table 4 (SEQ ID NO: 31-52). For example, the peptides obtained from the cell line CFPAC-1 are show mapped against the IkBβ2 (SEQ ID NO 27), IkBβ1 (SEQ ID NO 28) and IkBβ2 beta conceptual variant (SEQ ID NO29) which had the highest protein score and represented the most relevant identification. All peptides recovered from all cell lines either obtained in the initial MS analysis, or subsequent fragmentation as well as the peptides that were identified as variant peptides (described below) are combined and mapped to their positions in the variant of IkBβ2 (SEQ ID NO 30) in FIG. 8 and are listed Table 4 (SEQ ID NO: 31-52)

MS Fragmentation of Peptides 1985.978172 and 1070.468308

De novo sequence identification led to the identification of variant peptides in addition to those that mapped 100% to the sequence. A discrete nanospray head installed on a nano-source was used for the purpose. The collision energy was 48V, curtain gas and CAD gas were maintained at 25 and 6, respectively, and the sample allowed to cycle for 1.667 minutes (100 cycles) to obtain stable mass ion fragmentation. MS/MS fragmentation of two of the peptides (1985.978172 and 1070.468308) gave rise to the fragment ions shown in FIGS. 9A and 9B. Peptides, LGVLAAAVGGVGLGAWL (SEQ ID NO:34) from peptide mass 1985.978172 and peptide, ILGVTSTWAL (SEQ ID NO:37), from peptide mass 1070.468308 showed 100% homology to IkBβ2 in the flanking sequences but not with the sequence in the middle, indicating an identification of a novel sequence. The sequences include 8 amino acid changes resulting in two variant regions that have the characteristic hydrophobicity of transmembrane domains. These regions are approximately, LGSLGV-LAAAVGGVGL GAWLGPG (SEQ ID NO 53) and LAAILGVTSTWALYAAGAGLCV (SEQ ID NO: 54). The exact span of transmembrane domains vary slightly depending on the protein structure modeling algorithm used. The hydrophobic variant domains are separated by a wild type region of IkBβ. MS/MS fragmentation of one peptide (1205. 378172 from (402.800000,3+) (SEQ ID NO: 35)) gave rise to the additional fragment ions shown in FIG. 9C that showed 100% homology to IkBβ2.

Example 7

Immunoprecipitation of IkB□2 from Cancer Cell Lines Extracts

Figure 10:
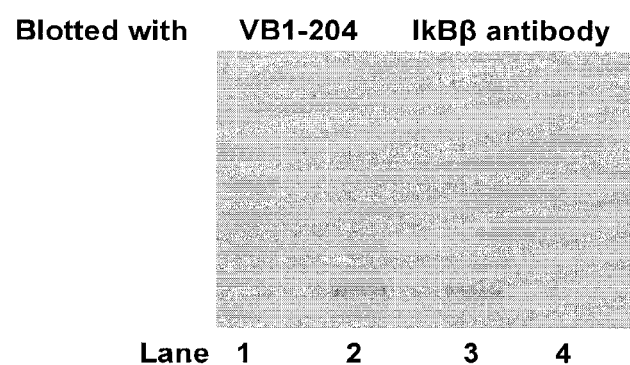
FIG. 10 shows a Western blot of VB1-204 immuno-precipitated proteins from whole cell lysate or from purified membrane fractions of CFPAC-1. The blots is probed with VB1-204 or a commercially available anti-IkBβ antibody.
Figure 12:
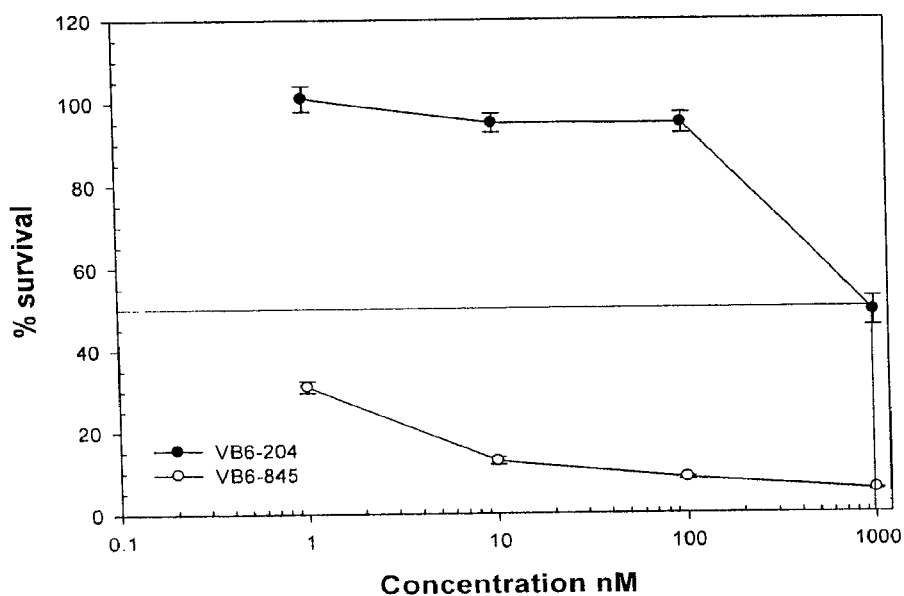
FIG. 12 shows the cytotoxic activity of VB1-204 in CFPAC-1 cells.

VB1-204 was used to immunopreciptate proteins from both purified membrane and whole cells extracts from the tumor cell line CFPAC-1. The purified proteins were then separated on SDS-PAGE gels. The separated proteins were analyzed by Western blot using VB1-204 and with a commercially available antibody that recognizes both IkBβ1 and IkBβ2 isoforms. The commercial antibody was raised against a recombinant peptide sequence covering amino acids 56-145 of kBβ (Abnova, HOOOO4793-M01). This region contains 3 amino acid changes (located at positions 106, 111 and 112) in the cancer-associated variant of IkBβ2 and also contains the putative extracellular portion of the variant (approximately between amino acids 38 and 102). FIG. 10 shows that VB1-204 binds to a protein present in whole cell lysate and in the membrane fraction while the commercial antibody only binds to the a whole cell lysate protein. All bands are of the same MW. The data suggests that VB 1-204 also detects wild-type IkBβ located inside the cell as well as the membrane form, while the commercial antibody only detect the intracellular wild-type and its binding to the cancer associated variant is prevented by the amino acid changes in the immunogenic peptide.

Example 8

Cytotoxicity of Immunotoxin Derived from VB1-204

The variable region of VB1-204 was used to engineer an immunoconjugate for use in the treatment of cancer. A modified form of the plant toxin bouganin was fused to the Fab form of VB1-204.

VB1-204 Engineering

The VB1-204 construct was engineered by creating the EcoRI-PeIB-$V_H$204-ApaI and AflII-PeIB-6×His-$V_L$204-$C_L$-XhoI fragments which were inserted into the EcoRI-ApaI-$C_H$-de-bouganin-AflII-XhoI/pING3302 plasmid. The engineered fragments were cloned directly into the pING3302 Xoma vector under the control of the arabinose-inducible araBAD promoter. Upon induction by L-(+) arabinose, the presence of the PeIB leader sequence, adjacent to the gene of interest resulted in the secretion of the protein into the culture supernatant. A histidine affinity tag, placed at the N-terminal end of the $V_L$-$C_L$ domain permitted purification using a $Ni^{2+}$-chelating capture method.

The EcoRI-PeIB-$V_H$204-ApaI fragment was assembled by the Splice Overlapping Extension Polymerase Chain Reaction method using the PeIB and VB1-204-$V_H$ DNA plasmids as templates and the following primers:

1) 5' PeIB:
(SEQ ID NO: 56)
5 ' GAA TTC CCT GCA GGT CTA TGG AAC GAT AAA TGC 2) 3' PeIB-$V_H$204:
(SEQ ID NO: 57)
5' CGC CAT CGC TGG TTG GGC AGC GAG TAA TAA CAA TCC 3) 5' PeIB-$V_H$204:
(SEQ ID NO :58)
5' GCT GCC AAA CCA GCG ATG GCG GAG GTG CAG CTG GTG GAG TCT GGG 4) 3' $V_H$204-ApaI:
(SEQ ID NO: 59)
5' AC CGA TGG GCC CTT GGT GGA GGC TGA GGA GAC GGT GAC CAG GGT

A two-step Splice Overlapping Extension PCR approach was undertaken using all 4 primers listed above to construct and amplify EcoRI-PeIB-$V_H$204-ApaI. The EcoRI and ApaI restriction sites (bolded) were added to facilitate the cloning of PeIB-$V_H$204 into the EcoRI-ApaI-$C_H$-de-bouganin-AflII-XhoI/3302 vector. The PCR reaction included a 50 µL reaction volume containing:

| | |
|---|---|
| 10X PCR buffer | 5 μL |
| 2 mM dNTPs | 5 μL |
| 50 mM MgCl$_2$ | 2 μL |
| Primer 5' | 20 pmol |
| Primer 3' | 20 pmol |
| Taq DNA Polymerase | 2.5 U |
| DNA template | 50 ng |

The cycling conditions for PCR were: 94° C. for 1 min., 62° C. for 1 min., and 72° C. for 1.5 min., for a total of 20 cycles followed by a final extension of 10 min. at 72° C.

Step 1

The first PCR reaction involved primers 1 and 2 and the PeIB template. This yielded a fragment (131 bp) with at the 5' end the PeIB region with a EcoRI restriction site, and at the 3' end the PeIB leader signal.

In a separate PCR reaction, primers 3 and 4 with 204 V$_H$ template were used to generate the V$_H$204 fragment (438 bp) flanked at the 5' end by the PeIB leader signal and the start of the V$_H$ domain and a domain with ApaI site.

Step 2

In the next PCR reaction, primers 1 and 4 were used with 1 μL from each PCR product to produce EcoRI-PeIB-V$_H$204-ApaI fragment (548 bp).

The AflII-PeIB-6×His-V$_L$204-C$_L$-XhoI fragment was assembled by the Splice Overlapping Extension Polymerase Chain Reaction method using VB1-204 light chain DNA plasmid as template and the following primers:

```
1) 5' De-boug-AflII:
                              (SEQ ID NO: 60)
5' ATC CTT AAG TTT AAA AGC TCC AAA TAG TGA TCT AGA
GTC GAC 2) 3' PeIB-6xHis:
                              (SEQ ID NO: 61)
5' GTG ATG GTG ATG GTG ATG CGC CAT CGC TGG 3) 5' 6xHis-V_L-204:
                              (SEQ ID NO: 62)
5' ATG GCG CAT CAC CAT CAC CAT CAC TCC TAT GAG CTG
ACT CAG CCA CCC 4) 3' V_L-C_L:
                              (SEQ ID NO: 63)
5' GAC CGA GGG GGC AGC TTG GGC TGA CCT AGG ACG GGT
CAG CTT GGT CCC 5) 5' Lambda constant:
                              (SEQ ID NO: 64)
5' CAG CCC AAG GCT GCC CCC TCG GTC ACT CTG TTC 6) 3' End-XhoI lambda constant:
                              (SEQ ID NO: 65)
5' CTC GAG TCA CTA TGA ACA TTCT GT AGG GGC CAC TGT
```

A two-step Splice Overlapping Extension PCR approach was undertaken using all 6 primers listed above to construct and amplify AflII-PeIB-6×His-V$_L$204-C$_L$XhoI. The AF1II and XhoI restriction sites (bolded) were added to facilitate the cloning of AflII-PeIB-6×His-V$_L$204-C$_L$-XhoI into the EcoRI-ApaI-C$_H$de-bouganin-AflII-XhoI/3302 vector.

Step 1

In the first PCR reaction, primers 1 and 2 were used to amply the PeIB fragment (195 bp) flanked at the 5' end with the AflII restriction site and at the 3' end with the 6×His tag.

In the second PCR reaction, primers 3 and 4 along with the VB1-204 light chain template were used to amplify 6×His-V$_L$204 fragment (379 bp) flanked at the 5' end with the 6×His and at the 3' end the first 21 nucleotides of the C$_L$ domain.

The third PCR reaction was performed with primers 5 and 6 along with C$_L$ template and yielded the lambda constant light chain (327 bp) containing at the 3' end the XhoI restriction site.

Step 2

In the next PCR reaction, primers 1 and 6 were used with 1 (xL from each PCR product to produce AflII-PeIB-6×His-V$_L$204-C$_L$XhoI fragment (833 bp).

Once the sequences were verified, the PeIB-V$_H$204 fragment was digested with the EcoRI and ApaI restriction enzymes and ligated into the EcoRI-ApaI-C$_H$-de-bouganin-AflII-XhoI/3302 vector pre-digested with same enzymes. 10F competent cells were transformed with the ligation reaction and plated onto LB-agar plates supplemented with tetracycline. The presence of the insert was confirmed by restriction mapping of the plasmid PeIB-V$_H$204-C$_H$-de-bouganin-AflII-XhoI/3302. The AflII-PeIB-6×His-V$_L$204-C$_L$XhoI fragment was then digested with the AflII and XhoI restriction enzymes and ligated into PeIB-V$_H$204-C$_H$de-bouganin-AflII-XhoI/3302 vector pre-digested with same enzymes to engineer VB1-204. Once the presence of the correct insert was confirmed by sequencing, the construct was transformed into E. coli E104 cells for expression. VB1-204 protein from the fermentation of 6 L TB was purified and tested. The nucleotide (SEQ ID NO:36) and amino acid sequences (SEQ ID NO:37) for the VB1-204 immunoconjugate are shown in FIG. 11.

Cytotoxicity of VB1-204 Proteins

The cytotoxicity of VB1-204 is measured by an MTS assay. Briefly, antigen-positive and antigen-negative cells were seeded at 1000 cells per well and incubated at 37° C. for 3 hours. Subsequently, varying concentrations of VB1-204 and de-bouganin are added to the cells and after 5 days, the cell viability determined. After 5 days incubation, the calculated IC$_{50}$ of VB1-204 is determined on the antigen positive cell lines due to significant cell death. In contrast, no IC$_{50}$ is determined with the antigen negative cell lines due to cells maintained viability.

Example 9

Cancer Stem Cell Assay

The binding of VB1-204 in conjunction with aldefluor (ALDH1) staining was used to assess cancer stem cell reactivity. In general, tumor cells with high ALDH staining represent the cancer stem cell fraction which is capable of self-renewal and of generating tumors in xenograft implants. High ALDH1 activity is believed to impart resistance to certain chemotherapeutics leading to the outgrowth of new tumors and the subsequent relapse in patents (Wicha M S, Liu S and Dontu G. 2006, Cancer Res. 66, 1883-1890; Ginestier C, Hur M H, Charafe-Jauffret E et al. 2007, Cell Stem Cell, 1, 555-567). Two color flow cytometry was used to measure VB1-204 binding to the ALDH 1-positive cells of the cervix cell line C33A and prostate cell line DU-145. VB1-204 binding to the ALDH1-positive C33A and DU-145 subpopulation highlights its potential utility against cancer stem cells.

Experimental design: Briefly, 2×10⁵ cells were incubated with the aldefluor reagent for 30 minutes at 37° C. Then, cells were washed and incubated at 4° C. in presence of 25 µg/mL of VB1-204 for 2 hours. VB1-204 bound to cells was detected using a biotinylated goat anti-human H&L followed by streptavidin Cy5. IgM Melanoma, a human IgM anti-Id was used as a negative control. As well, the specificity of the aldefluor, staining was demonstrated in presence of DEAB, an inhibitor of the reaction.

Figure 13:
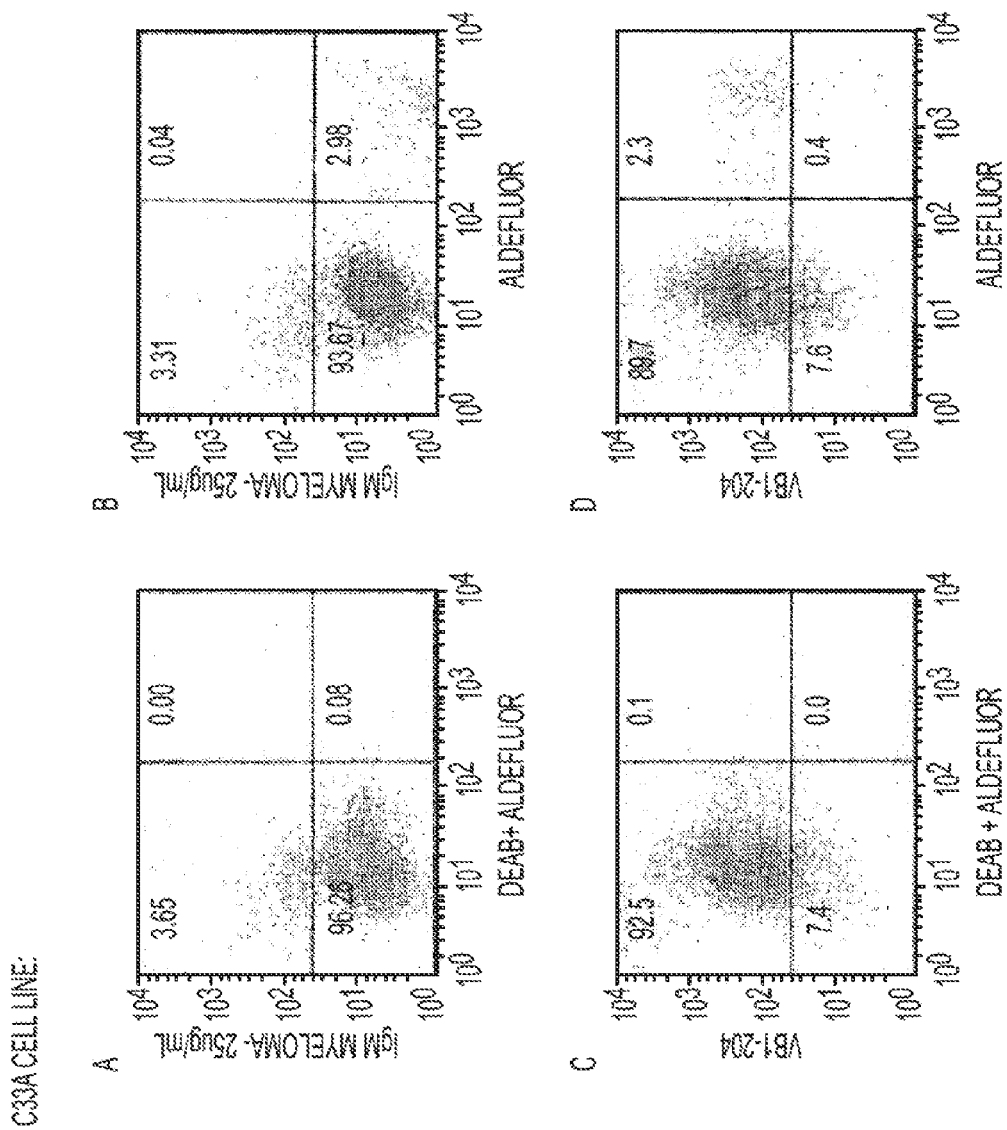
FIG. 13 shows the flow cytometry results with C33A cells showing the distribution of aldefluor reactivity in the presence (panels A and C) or absence of the inhibitor DEAB (panels B and D), and the specific VB1-204 binding (panels C and D) to those same cells.
Figure 14:
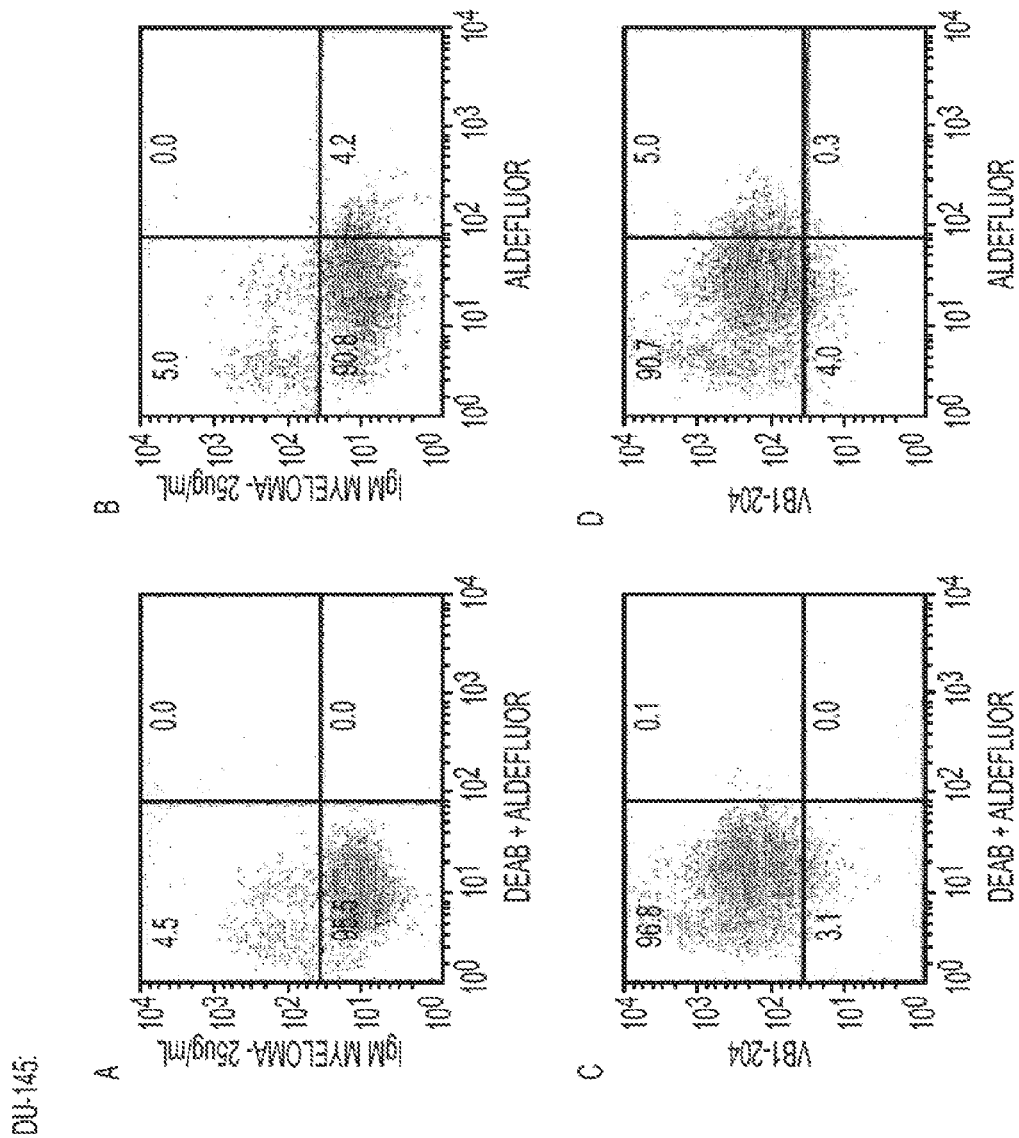
FIG. 14 shows the flow cytometry results with DU-145 cells showing the distribution of aldefluor reactivity in the presence (panels A and C) or absence of the inhibitor DEAB (panels B and D), and the specific VB1-204 binding (panels C and D) to those same cells.

Result: The results are shown in FIGS. 13 and 14. The analysis of the data showed that the 2.98% and 4.2% of the C33A and DU-145 cells are positive for the cancer stem cell marker aldefluor. (Lower right quadrant of FIGS. 13B and 14B). VB1-204 binds the majority of C33A (92.5%) & DU-145 (96.8%) cells as shown by a shifting of the cell profile to the upper left quadrant of FIGS. 13C and 14C. FIGS. 13D and 14D showed the ALDH1-positive cells of C33A (2.3%) and DU-145 (5.0%) also shifted to the upper right quadrant in presence of VB1-204. This data suggest that VB1-204 binds the cancer stem cell fraction of C33A & DU-145 and that the antigen recognized by VB1-204 is present of the cancer stem cell fraction.

While the present application has been described with reference to what are presently considered to be the preferred examples, it is to be understood that the present application is not limited to the disclosed examples. To the contrary, the present application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

CDR Sequences of VB1-204
VB1-204 CDR Sequences

|  | V_L Chain |  | V_H Chain |  |
|---|---|---|---|---|
| CDR1 | SGDKLGDKYAC | SEQ ID NO: 8 | SYAMH | SEQ ID NO: 5 |
| CDR2 | QDSKRPS | SEQ ID NO: 9 | VISYDGSNKYYADSVKG | SEQ ID NO: 6 |
| CDR3 | QAWDSSTW | SEQ ID NO: 10 | AHSRLLWFGELLPSAFDY | SEQ ID NO: 7 |

TABLE 2

Antibody Profiling of Tumor Cell Reactivity By Flow

| Cell Type | Cancer Type | MF |
|---|---|---|
| CFPac-1 | pancreas | 57.73 |
| MB-231 | breast | 54.21 |
| A-375 | skin | 45.74 |
| Hep-G2 | liver | 29.42 |
| DU-145 | prostate | 22.86 |
| SK-BR-3 | breast | 22.08 |
| MB-435S | breast | 16.68 |
| A-549 | lung | 16.26 |
| SK-OV-3 | ovary | 13.34 |
| Panc-1 | pancreas | 12.75 |

TABLE 3A

LD Array of Critical Normal Tissue for VBl-204

| Tissue | Membrane Staining | Score Range* | Cytoplasmic Staining | Score Range* |
|---|---|---|---|---|
| Brain | None (0/4) | 0 | 4/4 | 2-3+ (60-80%) |
| Colon | 1/5 | 1+ (10%) | 5/5 | 1-3+ (20-50%) |
| Heart | None (0/5) | 0 | 5/5 | 2+ (60-80%) |
| Kidney | None (0/5) | 0 | 5/5 | 2-3+ (50-70%) |
| Liver | 3/5 | 1+ (10%) | 5/5 | 1-3+ (10-70%) |
| Lung | 5/5 | 1+ (20%) | 5/5 | 1-2+ (10-40%) |
| Pancreas | None (0/5) | 0 | 5/5 | 1-3+ (10-70%) |
| Stomach | None (0/4) | 0 | 4/4 | 2-3+ (20-80%) |

Scoring was evaluated on a 0-3+ scale, with 0 = no staining and trace being less than 1+ but greater than 0. Grades 1+ to 3+ represent increased intensity of staining, with 3+ being strong.

TABLE 3B

High Density Tumor Tissue MicroArray stains with VBl-204

| Tissue | Membrane Staining | Score Range |
|---|---|---|
| Liver | 1/9 | 1-2+ (50%) |
| Colon | 4/8 | 1+ (10%) |
| Lung | 2/9 | 1+ (10%) |
| Pancreas | 1/6 | 1+ (40%) |
| Kidney | 1/8 | 1+ (10%) |
| Breast | 0/9 | 0 |
| Skin | 0/9 | 0 |
| Ovary | 0/9 | 0 |
| Head and Neck** | 0/8 | 0 |
| Prostate | 0/9 | 0 |

Scoring was evaluated on a 0-3+ scale, with 0 = no staining and trace being less than 1+ but greater than 0. Grades 1+ to 3+ represent increased intensity of staining, with 3+ being strong, dark brown staining.

Head & neck cancers included carcinomas of the trachea, larynx, tonsil, throat, soft palate, tongue, mouth and lips.

Values in parentheses indicate the highest percentage of cells stained in the scored range.

TABLE 4

List of peptides along with the respective calculated masses obtained corresponding to IKKβ2 (TRIP-9) and variant

| Location | Mr (Expected) | Sequence | SEQ ID NO: |
|---|---|---|---|
| 1-9 | 849.0740 | MAGVACLGK | SEQ ID NO: 31 |
| 13-42 | 2868.412 | ADEWCDTGLGSLGVLAAAVGGVGLGAWLGP | SEQ ID NO: 32 |
| 15-48 | 3293.654 | EWCDTGLGSLGVLAAAVGGVGLGAWLGPGLSWAP | SEQ ID NO: 33 |
| 24-40 | 1985.978 | LGVLAAAVGGVGLGAWL | SEQ ID NO: 34 |
| 77-86 | 1203.5811 | FLLGFSAGTEY | SEQ ID NO: 35 |
| 93-154 | 6545.565 | LGQTALHLAAILGVTSTWALYAAGAGLCVAERRGHT | SEQ ID NO: 36 |
| 103-113 | 1070.468 | ALHLACRVGAHACARALLQPRPRRPILGVTSTWAL | SEQ ID NO: 37 |
| 113-154 | 1293.403 | LYAAGAGLCVAER | SEQ ID NO: 38 |
| 137-144 | 783.9040 | VGAHACAR | SEQ ID NO: 39 |
| 145-152 | 950.1520 | ALLQPRPR | SEQ ID NO: 40 |
| 156-168 | 1432.5100 | EAPDTYLAQGPDR | SEQ ID NO: 41 |
| 169-187 | 2113.2650 | PDTNHTPVALYPDSDLEK | SEQ ID NO: 42 |
| 188-197 | 1309.2620 | EEEESEEDWK | SEQ ID NO: 43 |
| 198-218 | 2398.7040 | LQLEAENYEGHTPLHVAVIHK | SEQ ID NO: 44 |
| 219-204 | 748.0327 | DVEMVR | SEQ ID NO: 45 |
| 228-242 | 1544.6560 | DAGADLDKPEPTCGR | SEQ ID NO: 46 |
| 243-262 | 2158.5260 | SPLHLAVEAQAADVLELLLR | SEQ ID NO: 47 |
| 263-270 | 726.7900 | AGANPAAR | SEQ ID NO: 48 |
| 276-291 | 1707.0670 | TPLGSAMLRPNPILAR | SEQ ID NO: 49 |
| 295-307 | 1365.3760 | AHGAPEPEGEDEK | SEQ ID NO: 50 |
| 308-329 | 2172.0890 | SGPCSSSSDSDGGDEGVSQEER | SEQ ID NO: 51 |
| 330-338 | 716.7050 | QGSPAGGSG | SEQ ID NO: 52 |

The invention claimed is:

1. A recombinant antibody comprising a light chain variable region comprising the amino acid sequence of SEQ ID NO: 4 and a heavy chain variable region comprising the amino acid sequence of SEQ ID NO: 2.

2. The recombinant antibody of claim 1 wherein the antibody is an antibody fragment selected from the group consisting of Fab, Fab', F(ab')$_2$, scFv, dsFv, ds-scFv, dimers, minibodies, diabodies, bispecific antibody fragments, and multimers thereof.

3. A recombinant antibody comprising:
light chain complementarity determining regions comprising the amino acid sequences defined by SEQ ID NOS: 8, 9 and 10 and
heavy chain complementarity determining regions comprising the amino acid sequences defined by SEQ ID NOS: 5, 6 and 7.

4. The recombinant antibody according to claim 3, wherein the antibody binds to the extracellular domain of IkBβ protein.

5. The recombinant antibody of claim 3, wherein the antibody is an antibody fragment.

6. The recombinant antibody of claim 5, wherein the antibody fragment is selected from the group consisting of Fab, Fab', F(ab')$_2$, scFv, dsFv, ds-scFv, dimers, minibodies, diabodies, bispecific antibody fragments, and multimers thereof.

7. A composition comprising the recombinant antibody according to claim 3 and a pharmaceutically acceptable excipient, carrier, buffer or stabilizer.

8. A kit for diagnosing cancer comprising a recombinant antibody of claim 3 that binds to an antigen on the cancer cell and instructions for the use thereof.

9. A diagnostic agent comprising a recombinant antibody according to claim 3 attached to a label that produces a detectable signal, directly or indirectly.

10. The diagnostic agent of claim 9, wherein the label is a radioisotope, a fluorescent compound, a chemiluminescent compound, an enzyme, an imaging agent or a metal ion.

11. A kit comprising the diagnostic agent of claim 9 and instructions for the use thereof.

12. An immunoconjugate comprising an antibody attached to a cancer therapeutic, wherein the antibody comprises light chain complementarity determining regions having the amino acid sequences defined by SEQ ID NOS: 8, 9 and 10, and heavy chain complementarity determining regions having the amino acid sequences defined by SEQ ID NOS: 5, 6 and 7.

13. The immunoconjugate of claim 12, wherein the antibody binds to an antigen on a cancer cell.

14. The immunoconjugate of claim 12, wherein the cancer therapeutic is cytotoxic, cytostatic or otherwise prevents or reduces the ability of the cancer cells to divide or metastasize.

15. The immunoconjugate of claim 12, wherein the cancer therapeutic is a cytotoxin.

16. The immunoconjugate of claim 15, wherein the cytotoxin is a ribosome-inactivating polypeptide.

17. The immunoconjugate according to claim 15, wherein the cytotoxin is selected from the group consisting of gelonin, bouganin, saporin, ricin, ricin A chain, bryodin, diphtheria, restrictocin, *Pseudomonas* exotoxin A and combinations thereof.

18. The immunoconjugate of claim 15, wherein the cytotoxin is selected from modified bouganin and functional variant thereof.

19. The immunoconjugate of claim 15, wherein the cytotoxin is selected from a truncated form of *Pseudomonas* exotoxin A that consists of amino acids 252-608 and a functional variant thereof.

20. The immunoconjugate according to claim 12 wherein the immunoconjugate is internalized by the cancer cell.

21. The immunoconjugate according to claim 12, comprising a first polypeptide having the amino acid sequence from amino acid 23 to amino acid 514 of SEQ ID NO: 67, and a second polypeptide having the amino acid sequence from amino acid 537 to amino acid 754 of SEQ ID NO: 67, and wherein the first polypeptide and the second polypeptide are linked by a di-sulfide bond.

22. A composition comprising the immunoconjugate according to claim 12 with a pharmaceutically acceptable excipient, carrier, buffer or stabilizer.

23. A kit for treating or preventing cancer comprising an effective amount of the immunoconjugate of claim 12, and directions for the use thereof to treat or prevent the cancer.

24. A immunoconjugate comprising an antibody attached to a cancer therapeutic, wherein the antibody comprises a light chain variable region comprising the amino acid sequence of SEQ ID NO: 4, and a heavy chain variable region comprising the amino acid sequence of SEQ ID NO: 2.

25. The immunoconjugate of claim 24, wherein the cancer therapeutic is a cytotoxin.

26. The immunoconjugate of claim 25, wherein the cytotoxin is selected from the group consisting of gelonin, bouganin, saporin, ricin, ricin A chain, bryodin, diphtheria, restrictocin, *Pseudomonas* exotoxin A and combinations thereof.

27. The immunoconjugate of claim 25, wherein the cytotoxin is modified bouganin.

28. The immunoconjugate of claim 25, wherein the cytotoxin is a truncated form of *Pseudomonas* exotoxin A that consists of amino acids 252-608.

29. A method of detecting or monitoring cancer in a subject comprising the steps of:
  (1) contacting a test sample taken from said subject with the recombinant antibody of claim 3 to produce a antibody-antigen complex;
  (2) measuring the amount of antibody-antigen complex in the test sample; and
  (3) comparing the amount of antibody-antigen complex in the test sample to a control.

* * * * *